United States Patent
Garner

(10) Patent No.: US 12,431,220 B2
(45) Date of Patent: Sep. 30, 2025

(54) METHODS AND SYSTEMS FOR MICROSATELLITE ANALYSIS

(71) Applicant: ORBIT GENOMICS, INC., Boulder, CO (US)

(72) Inventor: Harold Garner, Blacksburg, VA (US)

(73) Assignee: ORBIT GENOMICS, INC., Boulder, CO (US)

( * ) Notice: Subject to any disclaimer, the term of this patent is extended or adjusted under 35 U.S.C. 154(b) by 221 days.

(21) Appl. No.: 17/508,322

(22) Filed: Oct. 22, 2021

(65) Prior Publication Data

US 2022/0189583 A1 Jun. 16, 2022

Related U.S. Application Data

(63) Continuation of application No. PCT/US2020/029145, filed on Apr. 21, 2020.

(60) Provisional application No. 62/837,109, filed on Apr. 22, 2019.

(51) Int. Cl.
G16H 50/20 (2018.01)
G16B 20/00 (2019.01)
G16B 40/20 (2019.01)

(52) U.S. Cl.
CPC ............ G16B 40/20 (2019.02); G16B 20/00 (2019.02); G16H 50/20 (2018.01)

(58) Field of Classification Search
None
See application file for complete search history.

(56) References Cited

U.S. PATENT DOCUMENTS

| | | | |
|---|---|---|---|
| 2007/0269804 A1* | 11/2007 | Liew | G16B 40/00 702/19 |
| 2010/0070191 A1* | 3/2010 | Gold | G01N 33/57423 436/64 |
| 2010/0240540 A1 | 9/2010 | Yeatman et al. | |
| 2012/0040861 A1* | 2/2012 | Williams | G16B 20/20 901/41 |
| 2014/0235456 A1 | 8/2014 | Garner, Jr. et al. | |
| 2015/0065357 A1 | 3/2015 | Fox | |
| 2015/0337388 A1 | 11/2015 | Garner, Jr. et al. | |

(Continued)

FOREIGN PATENT DOCUMENTS

| WO | WO-2017176834 A2 | 10/2017 |
| WO | WO-2019067092 A1 | 4/2019 |

(Continued)

OTHER PUBLICATIONS

"Receiver-Operating Characteristic Analysis for Evaluating Diagnostic Tests and Predictive Models"; Zou et al.; 2007; DOI: 10.1161/CirculationAHA.105.594929 (Year: 2007).*

(Continued)

*Primary Examiner* — John A Pauls
(74) *Attorney, Agent, or Firm* — Wilson Sonsini Goodrich & Rosati.

(57) ABSTRACT

The present disclosure provides methods and systems for classifying microsatellite and minor alleles in a sample. Also, the present disclosure provides methods and systems for generating classifiers for conditions based on microsatellite loci and for performing pan-cancer assays. The methods and systems can involve next-generation sequencing of nucleic acid samples from subjects and genotyping microsatellite loci in the samples.

20 Claims, 38 Drawing Sheets

(56) References Cited

U.S. PATENT DOCUMENTS

| | | | |
|---|---|---|---|
| 2016/0040254 | A1 | 2/2016 | Garner et al. |
| 2017/0004417 | A1 | 1/2017 | Bruillard et al. |
| 2017/0372229 | A1* | 12/2017 | Ura .................. G06N 20/00 |
| 2019/0087239 | A1* | 3/2019 | Adibowo ............. G06N 20/20 |
| 2020/0025767 | A1* | 1/2020 | Gaul ............... G01N 33/57449 |
| 2020/0118644 | A1* | 4/2020 | Khan .................. G16B 50/10 |

FOREIGN PATENT DOCUMENTS

| | | |
|---|---|---|
| WO | WO-2019079166 A1 | 4/2019 |
| WO | WO-2020219463 A1 | 10/2020 |

OTHER PUBLICATIONS

"Classification and Characterization of microsatellite instability across 18 cancer types"; Hause et al.; Oct. 3, 2017 (Year: 2017).*

"Microsatellite markers: what they mean and why they are so useful"; Viera et al.; May 13, 2016 (Year: 2016).*

"A direct characterization of human mutation based on microsatellites"; Sun et al.; Aug. 23, 2012; (Year: 2012).*

Adhyam et al., A review on the clinical utility of PSA in cancer prostate. Indian J Surg Oncol. 3(2):120-129 (2012).

Anandakrishnan et al., Estimating the number of genetic mutations (hits) required for carcinogenesis based on the distribution of somatic mutations. PLoS Comput Biol. 15(3):e1006881, pp. 1-19 (2019).

Anderson-Cook, Practical genetic algorithms: Taylor & Francis; 2005.

Bacolla et al., Non-B DNA conformations as determinants of mutagenesis and human disease. Mol Carcinog. 48(4):273-285 (2009).

Balog et al., Parallel assessment of CpG methylation by two-color hybridization with oligonucleotide arrays. Anal Biochem. 309(2):301-310 (2002).

Baudrin et al., Molecular and Computational Methods for the Detection of Microsatellite Instability in Cancer. 8:621, pp. 1-11 (2018).

Bavarva et al., Nicotine and oxidative stress induced exomic variations are concordant and overrepresented in cancer-associated genes. Oncotarget. 5(13):4788-4798 (2014).

Bavarva et al., The dynamic exome: acquired variants as individuals age. Aging (Albany NY). 6(6):511-21 (2014).

Belosludtsev et al., Organism identification using a genome sequence-independent universal microarray probe set. Biotechniques. 37(4):654-658 (2004).

Borstnik et al., Tandem repeats in protein coding regions of primate genes. Genome Res. 12(6):909-915 (2002).

Brinkmann et al., Mutation rate in human microsatellites: influence of the structure and length of the tandem repeat. Am J Hum Genet. 62(6):1408-1415 (1998).

Cerami et al., The cBio cancer genomics portal: an open platform for exploring multidimensional cancer genomics data. Cancer Discov. 2(5):401-404 (2012).

Cordaux et al., The impact of retrotransposons on human genome evolution. Nat Rev Genet. 10(10):691-703 (2009).

Dash et al., Differentiating between cancer and normal tissue samples using multi-hit combinations of genetic mutations. Sci Rep. 9(1):1005, pp. 1-13 (2014).

Devlin-Durante et al., How old are you? Genet age estimates in a clonal animal. Mol Ecol. 25(22):5628-5646 (2016).

Dupont et al., Power and sample size calculations. A review and computer program. Control Clin Trials. 11(2):116-128 (1990).

Dupont et al., PS power and sample size program available for free on the Internet. Control Clin Trials. 18(3):274, 1pg. (1997).

Ellegren, Microsatellites: simple sequences with complex evolution. Nat Rev Genet. 5(6):435-445 (2004).

Fisher, The statistical utilization of multiple measurements. Ann Eugenic. 8:376-386 (1938).

Fondon et al., Computerized polymorphic marker identification: experimental validation and a predicted human polymorphism catalog. Proc Natl Acad Sci USA. 95(13):7514-7519 (1998).

Fondon et al., Detection of length-dependent effects of tandem repeat alleles by 3-D geometric decomposition of craniofacial variation. Dev Genes Evol. 217(1):79-85 (2007).

Fondon et al., Molecular origins of rapid and continuous morphological evolution. Proc Natl Acad Sci USA. 101(52):18058-18063 (2004).

Fonville et al., Genomic leftovers: identifying novel microsatellites, over-represented motifs and functional elements in the human genome. Sci Rep. 6:27722, pp. 1-7 (2016).

Fonville et al., Population analysis of microsatellite genotypes reveals a signature associated with ovarian cancer. Oncotarget. 6(13):11407-11420 (2015).

Forgacs et al., Searching for microsatellite mutations in coding regions in lung, breast, ovarian and colorectal cancers. Oncogene. 20(8):1005-1009 (2001).

Galindo et al., A long AAAG repeat allele in the 5' UTR of the ERR-γ gene is correlated with breast cancer predisposition and drives promoter activity in MCF-7 breast cancer cells. Breast Cancer Res Treat. 130(1):41-48 (2011).

Galindo et al., Global microsatellite content distinguishes humans, primates, animals, and plants. Mol Biol Evol. 26(12):2809-2819 (2009).

Galindo et al., Sporadic breast cancer patients' germline DNA exhibit an AT-rich microsatellite signature. Genes Chromosomes Cancer. 50(4):275-283 (2011).

Gao et al., Integrative analysis of complex cancer genomics and clinical profiles using the cBioPortal. Sci Signal. 6(269):pl1, pp. 1-20 (2013).

Garner et al., The evolution of custom microarray manufacture. IEEE Eng Med Biol Mag. 21(4):123-125 (2002).

Garner et al., What do the changes in the aging genome mean for pharmacogenomics? Pharmacogenomics. 15(14):1725-1728 (2014).

Giannakis et al., RNF43 is frequently mutated in colorectal and endometrial cancers. Nat Genet. 46(12):1264-1266 (2014).

Gu et al., BCL6B suppresses proliferation and migration of colorectal carcinoma cells through inhibition of the PI3K/AKT signaling pathway. Int J Mol Med. 41(5):2660-2668 (2018).

Guerreiro et al., Targeting the PI3K p110alpha isoform inhibits medulloblastoma proliferation, chemoresistance, and migration. Clin Cancer Res. 14(21):6761-6769 (2008).

Gymrek et al., Abundant contribution of short tandem repeats to gene expression variation in humans. Nat Genet. 48(1):22-29 (2016).

Haberman et al., Trinucleotide repeats are prevalent among cancer-related genes. Trends Genet. 24(1):14-18 (2008).

Hannan, Tandem repeat polymorphisms: Mediators of genetic plasticity, modulators of biological diversity and dynamic sources of disease susceptibility. Adv Exp Med Biol. Ch. 1, 769:1-9 (2012).

Hannan, Tandem repeats mediating genetic plasticity in health and disease. Nat Rev Genet. 19(5):286-298 (2018).

Highnam et al., Accurate human microsatellite genotypes from high-throughput resequencing data using informed error profiles. Nucleic Acids Res. 41(1):e32, pp. 1-7 (2013).

Hu et al., Epigenetic silencing BCL6B induced colorectal cancer proliferation and metastasis by inhibiting P53 signaling. Am J Cancer Res. 5(2):651-662 (2015).

Jemal et al., Lung cancer screening with low-dose computed tomography in the United States—2010 to 2015. JAMA Oncol. 3(9):1278-1281 (2017).

Jones et al., Dissecting the genomic complexity underlying medulloblastoma. Nature. 488(7409):100-105 (2012).

Kang et al., Genomic signatures of speciation in sympatric and allopatric Hawaiian picture-winged *Drosophila*. Genome Biol Evol. 8(5):1482-1488 (2016).

Karunasena et al., Cut from the same cloth: Shared microsatellite variants among cancers link to ectodermal tissues-neural tube and crest cells. 6(26):22038-22047 (2015).

Karunasena et al., Somatic intronic microsatellite loci differentiate glioblastoma from lower-grade gliomas. Oncotarget. 5(15):6003-6014 (2014).

(56) References Cited

OTHER PUBLICATIONS

Kashi et al., Simple sequence repeats as advantageous mutators in evolution. Trends Genet. 22(5):253-259 (2006).

Kautto et al., Performance evaluation for rapid detection of pan-cancer microsatellite instability with MANTIS. Oncotarget. 8(5):7452-7463 (2017).

Kim et al., Divergence of *Drosophila melanogaster* repeatomes in response to a sharp microclimate contrast in Evolution Canyon, Israel. Proc Natl Acad Sci USA. 111(29):10630-10635 (2014).

Kinney et al., CAGm: a Repository of Germline Microsatellite Variations in the 1000 Genomes Project. Nucleic Acids Res. 47(D1):D39-D45 (2019).

Kinney et al., Whole-exome sequencing reveals microsatellite DNA markers for response to dofetilide initiation in patients with persistent atrial fibrillation: A pilot study. Clin Cardiol. 41(6):849-854 (2018).

Kinney et al., ZDHHC3 as a risk and mortality marker for breast cancer in African American women. Cancer Inform. 16:1-6 (2017).

Kramer et al., Causal analysis approaches in ingenuity pathway analysis. Bioinformatics. 30(4):523-530 (2014).

Laidlaw et al., Elevated basal slippage mutation rates among the Canidae. J Hered. 98(5):452-460 (2007).

Langmead et al., Fast gapped-read alignment with Bowtie 2. Nat Methods. 9(4):357-359 (2012).

Li et al., Epigenetic silencing of BCL6B inactivates p53 signaling and causes human hepatocellular carcinoma cell resist to 5-FU. Oncotarget. 6(13):11547-11560 (2015).

Li et al., Genetic variants and risk of lung cancer in never smokers: a genome-wide association study. Lancet Oncol. 11(4):321-330 (2010).

Li et al., Microsatellites: genomic distribution, putative functions and mutational mechanisms: a review. Mol Ecol. 11(12):2453-2465 (2002).

Li et al., Microsatellites within genes: structure, function, and evolution. Mol Biol Evol. 21(6):991-1007 (2004).

Lian et al., Evidence for the regulation of alternative splicing via complementary DNA sequence repeats. Bioinformatics. 21(8):1358-1364 (2005).

Luebke et al., Prioritized selection of oligodeoxyribonucleotide probes for efficient hybridization to RNA transcripts. Nucleic Acids Res. 31(2):750-758 (2003).

Maruvka et al., Analysis of somatic microsatellite indels identifies driver events in human tumors. Nat Biotechnol. 35(10):951-959 (2017).

McIver et al., Evaluation of microsatellite variation in the 1000 Genomes Project pilot studies is indicative of the quality and utility of the raw data and alignments. Genomics. 97(4):193-199 (2011).

McIver et al., Microsatellite genotyping reveals a signature in breast cancer exomes. Breast Cancer Res Treat. 145(3):791-798 (2014).

McIver et al., Population-scale analysis of human microsatellites reveals novel sources of exonic variation. Gene. 516(2):328-334 (2013).

Mehta et al., A network algorithm for performing Fisher's exact test in r x c contingency tables. J Am Stat Assoc. 78(382):427-434 (1983).

Michalak et al., Nucleolar dominance and maternal control of 45S rDNA expression. Proc Biol Sci. 282(1820):20152201 (2015).

Moyer et al., Screening for gestational diabetes mellitus: U.S. Preventive Services Task Force recommendation statement. Ann Intern Med. 160(6):414-420 (2014).

Nithianantharajah et al., Dynamic mutations as digital genetic modulators of brain development, function and dysfunction. Bioessays. 29(6):525-535 (2007).

Northcott et al., The whole-genome landscape of medulloblastoma subtypes. Nature. 547(7663):311-317 (2017).

Orr et al., Trinucleotide repeat disorders. Annu Rev Neurosci. 30:575-621 (2007).

Ostrowski et al., Using linked markers to estimate the genetic age of a volunteer population: a theoretical and empirical approach. Heredity (Edinb). 105(4):358-369 (2010).

Parsons et al., The genetic landscape of the childhood cancer medulloblastoma. Science. 331(6016):435-439 (2011).

Patidar et al., The Kub5-Hera/RPRD1B interactome: a novel role in preserving genetic stability by regulating DNA mismatch repair. Nucleic Acids Res. 44(4):1718-1731 (2016).

PCT/US2020/029145 International Search Report and Written Opinion dated Jul. 23, 2020.

Pearson et al., Repeat instability: mechanisms of dynamic mutations. Nat Rev Genet. 6(10):729-742 (2005).

Pugh et al., Medulloblastoma exome sequencing uncovers subtype-specific somatic mutations. Nature. 488(7409):106-110 (2012).

Riley et al., Embryonic nervous system genes predominate in searches for dinucleotide simple sequence repeats flanked by conserved sequences. Gene. 429(1-2):74-79 (2009).

Rivera et al., Lung cancer in never smokers. Adv Exp Med Biol. 893:43-57 (2016).

Robinson et al., Novel mutations target distinct subgroups of medulloblastoma. Nature. 488(7409):43-48 (2012).

Sawaya et al., Promoter microsatellites as modulators of human gene expression. Tandem Repeat Polymorphisms (Ed. Hannan). Ch. 4:41-54 (2012).

Slager et al., Mutations in RAI1 associated with Smith-Magenis syndrome. Nat Genet. 33(4):466-468 (2003).

Sun et al., A direct characterization of human mutation based on microsatellites. Nat Genet. 44(10):1161-1165 (2012).

Szklarczyk et al., STRING v10: protein-protein interaction networks, integrated over the tree of life. Nucleic Acids Res. 43(Database issue):D447-D452 (2015).

Tae et al., Improved variation calling via an iterative backbone remapping and local assembly method for bacterial genomes. Genomics. 100(5):271-276 (2012).

Tae et al., Revised genome sequence of Brucella suis 1330. J Bacteriol. 193(22):6410 (2011).

Tae et al., ReviSTER: an automated pipeline to revise misaligned reads to simple tandem repeats. Bioinformatics. 29(14):1734-1741 (2013).

Tae, Hongseok et al. Discretized Gaussian mixture for genotyping of microsatellite loci containing homopolymer runs. Bioinformatics (Oxford, England) vol. 30,5 (2014): 652-9. doi:10.1093/bioinformatics/btt595.

Taylor et al., Molecular subgroups of medulloblastoma: the current consensus. Acta Neuropathol. 123(4):465-472 (2012).

Thompson et al., Genomics identifies medulloblastoma subgroups that are enriched for specific genetic alterations. J Clin Oncol. 24(12):1924-1931 (2006).

U.S. Appl. No. 17/508,322 Non-final Office Action dated Nov. 6, 2023.

Vaksman et al., Exome-wide somatic microsatellite variation is altered in cells with DNA repair deficiencies. PLoS One. 9(11):e110263, pp. 1-14 (2014).

Vaksman et al.; Somatic microsatellite variability as a predictive marker for colorectal cancer and liver cancer progression. Oncotarget. 6(8):5760-5771 (2015).

Velmurugan et al., Dysfunctional DNA repair pathway via defective FANCD2 gene engenders multifarious exomic and transcriptomic effects in Fanconi anemia. Mol Genet Genomic Med. 6(6):1199-1208 (2018).

Velmurugan et al., High-depth, high-accuracy microsatellite genotyping enables precision lung cancer risk classification. Oncogene. 36(46):6383-6390 (2017).

Vinces et al., Unstable tandem repeats in promoters confer transcriptional evolvability. Science. 324(5931):1213-1216 (2009).

Wagner et al., Role of c-Abl kinase in DNA mismatch repair-dependent G2 cell cycle checkpoint arrest responses. J Biol Chem. 283(31):21382-21393 (2008).

Wandstrat et al., Association of extensive polymorphisms in the SLAM/CD2 gene cluster with murine lupus. Immunity. 21(6):769-780 (2004).

Wang et al., BCL6B expression in hepatocellular carcinoma and its efficacy in the inhibition of liver damage and fibrogenesis. Oncotarget. 6(24):20252-20265 (2015).

(56) References Cited

OTHER PUBLICATIONS

Wang et al., MSIpred: a python package for tumor microsatellite instability classification from tumor mutation annotation data using a support vector machine. Sci Rep. 8(1):17546, pp. 1-10 (2018).

Waszak et al., Spectrum and prevalence of genetic predisposition in medulloblastoma: a retrospective genetic study and prospective validation in a clinical trial cohort. Lancet Oncol. 19(6):785-798 (2018).

Wistuba et al., High resolution chromosome 3p allelotyping of human lung cancer and preneoplastic/preinvasive bronchial epithelium reveals multiple, discontinuous sites of 3p allele loss and three regions of frequent breakpoints. Cancer Res. 60(7):1949-1960 (2000).

Wren et al., Repeat polymorphisms within gene regions: phenotypic and evolutionary implications. Am J Hum Genet. 67(2):345-356 (2000).

Xu et al., Epigenetic inactivation of BCL6B, a novel functional tumour suppressor for gastric cancer, is associated with poor survival. 61(7):977-985 (2012).

Yang et al., Promoter hypermethylation of BCL6B gene is a potential plasma DNA biomarker for gastric cancer. Biomarkers 18(8):721-725 (2013).

\* cited by examiner

Fig. 17

| micro | chrom | start_pos | stop_pos | micro_unit | gene | feature |
|---|---|---|---|---|---|---|
| 129444 | >chr15 | 40734618 | 40734634 | Ax17 | - | - |
| 242677 | >chr1 | 1.54E+08 | 153770152 | GTx9 | INTS3 | intron |
| 124267 | >chr14 | 1.01E+08 | 101032212 | Tx24 | - | - |
| 55977 | >chr11 | 1.28E+08 | 128480513 | Ax12 | ETS1 | intron |
| 26882 | >chr10 | 1.18E+08 | 118007182 | Ax16 | RAB11FIP2 | exon,utr3 |
| 384178 | >chr3 | 1.91E+08 | 198862374 | AGx6 | GMNC | intron |
| 576220 | >chr9 | 99968416 | 99968429 | Tx14 | STX17 | intron |
| 328178 | >chr2 | 1.58E+08 | 158179117 | Tx11 | CCDC148 | nc_intron,intron |
| 9032 | >chr10 | 36522760 | 36522794 | GTx17.5 | - | - |
| 383947 | >chr3 | 1.9E+08 | 189907252 | Tx16 | - | - |
| 504566 | >chr7 | 37033493 | 37033506 | Ax14 | ELMO1 | intron |
| 170676 | >chr17 | 37224967 | 37224990 | TAx12 | ACACA | intron |
| 41907 | >chr11 | 62357225 | 62357267 | TTTTGx8.6 | ASRGL1 | intron |
| 180899 | >chr17 | 78051481 | 78051498 | Ax18 | TNRC6C | intron |
| 83881 | >chr12 | 1.22E+08 | 122238807 | ACx18.5 | VPS33A | intron |
| 322730 | >chr2 | 1.32E+08 | 132270849 | AGx8.5 | - | - |
| 501508 | >chr7 | 21765611 | 21765659 | CAx24.5 | DNAH11 | intron |
| 199833 | >chr19 | 45296611 | 45296650 | ACx20 | PLIN5 | - |
| 212148 | >chr19 | 49808545 | 49808562 | CCCCTGx3 | FUZ | nc_intron,intron |
| 396349 | >chr4 | 48653808 | 48653855 | AGCx16 | FRYL | utr5,intron |
| 483292 | >chr6 | 1.07E+08 | 106519008 | CAx16.5 | CRYBG1 | intron |
| 368122 | >chr3 | 70126256 | 70126270 | Tx15 | - | - |
| 68647 | >chr12 | 56109125 | 56109141 | Ax17 | PA2G4 | intron |

Fig. 19

| micro | chrom | start_pos | stop_pos | micro_unit | gene | feature |
|---|---|---|---|---|---|---|
| 157476 | >chr16 | 70032140 | 70032150 | Ax11 | PDXDC2P-NPIPB14P | nc_intron |
| 248188 | >chr1 | 1.79E+08 | 179348815 | TGx27.5 | SOAT1 | nc_intron,intron |
| 528184 | >chr7 | 1.48E+08 | 148217121 | Tx13 | CNTNAP2 | intron |
| 373633 | >chr3 | 1.41E+08 | 140959557 | Ax15 | SLC25A36 | intron |
| 209997 | >chr19 | 42527505 | 42527548 | GTx22 | LIPE-AS1 | nc_intron,intron |
| 319376 | >chr2 | 1.16E+08 | 116039886 | TGCx18 | - | - |
| 124723 | >chr14 | 1.03E+08 | 102875540 | Tx12 | TRAF3 | intron |
| 134687 | >chr15 | 64395361 | 64395385 | TGx12.5 | TRIP4 | utr5,nc_intron,intron |
| 385680 | >chr3 | 1.98E+08 | 197782065 | Tx22 | FYTTD1 | nc_exon,exon,utr3 |
| 6445 | >chr10 | 26223687 | 26223728 | GTx21 | GAD2 | intron |
| 97083 | >chr13 | 69975811 | 69975834 | CAx12 | KLHL1 | intron |
| 135927 | >chr15 | 69761404 | 69761452 | CATCx12.3 | - | - |
| 373981 | >chr3 | 1.42E+08 | 142499308 | Tx13 | ATR | intron |
| 518259 | >chr7 | 1.02E+08 | 101739890 | GAGx8 | - | - |
| 367289 | >chr3 | 1.09E+08 | 108905373 | Ax17 | GUCA1C | intron |
| 416763 | >chr4 | 1.52E+08 | 151662771 | Tx16 | FAM160A1 | exon,utr3 |
| 270222 | >chr20 | 33623955 | 33623983 | Ax29 | CBFA2T2 | intron |
| 258030 | >chr1 | 2.26E+08 | 225874184 | ACx8 | TMEM63A | intron |
| 139193 | >chr15 | 85123338 | 85123386 | ACx24.5 | PDE8A | intron |
| 168902 | >chr17 | 29293671 | 29293686 | ACx8 | NUFIP2 | intron |
| 185622 | >chr18 | 14837170 | 14837179 | Tx10 | ANKRD30B | intron |
| 386610 | >chr4 | 4299777 | 4299811 | GTx17.5 | ZBTB49 | utr5,nc_intron,intron |

Fig. 19 (cont.)

| micro | chrom | start_pos | stop_pos | micro_unit | gene | feature |
|---|---|---|---|---|---|---|
| 216664 | chr1 | 10297149 | 10297165 | Tx17 | KIF1B | intron |
| 252634 | chr1 | 2E+08 | 200343433 | Ax15 | LINC00862 | nc_intron |
| 177366 | chr17 | 64504983 | 64504996 | TCx7 | DDX5 | intron |
| 340380 | chr2 | 2.18E+08 | 217848192 | GCTx9.7 | TNS1 | cds |
| 472386 | chr6 | 49470141 | 49470153 | Tx13 | CENPQ | utr5,intron |
| 216250 | chr1 | 89446030 | 89446056 | CTTx9 | CA6 | intron |
| 400945 | chr4 | 71755149 | 71755177 | TATTx7.3 | GC | intron |
| 402100 | chr4 | 77773174 | 77773189 | Ax16 | CNOT6L | intron |
| 266313 | chr20 | 13715178 | 13715191 | Ax14 | ESF1 | intron |
| 407194 | chr4 | 1.03E+08 | 102949116 | ACx7.5 | SLC9B1 | nc_intron,intron |
| 385364 | chr3 | 1.96E+08 | 196361954 | Ax16 | UBXN7 | intron |
| 583803 | chr9 | 1.33E+08 | 132897631 | Ax18 | TSC1 | intron |
| 311251 | chr2 | 73673778 | 73673809 | TCx16 | ALMS1P1 | nc_intron |
| 158733 | chr16 | 75234097 | 75234113 | ACx8.5 | BCAR1 | intron |
| 442521 | chr5 | 91149985 | 91150025 | TTCTTx6.8 | ADGRV1 | nc_intron,intron |
| 219207 | chr1 | 20817282 | 20817299 | AAAAATx3 | EIF4G3 | intron |
| 59461 | chr12 | 96955856 | 96958494 | TGAx13 | CLEC2D | nc_exon,exon,utr3 |
| 23937 | chr10 | 1.04E+08 | 104037301 | Tx14 | COL17A1 | intron |
| 310093 | chr2 | 68217012 | 68217040 | ACx14.5 | PPP3R1 | intron |
| 356800 | chr3 | 54386695 | 54386712 | Tx18 | CACNA2D3 | intron |
| 270504 | chr20 | 34759030 | 34759042 | Tx13 | NCOA6 | intron |
| 377790 | chr3 | 1.61E+08 | 161221988 | Tx30 | NMD3 | utr5,intron |
| 386985 | chr4 | 6084968 | 6084994 | Ax27 | JAKMIP1 | intron |

Fig. 19 (cont.)

| micro | chrom | start_pos | stop_pos | micro_unit | gene | feature |
|---|---|---|---|---|---|---|
| 523569 | >chr7 | 1.28E+08 | 127594060 | TGx8 | FSCN3 | intron |
| 41994 | >chr11 | 62751951 | 62751962 | Ax12 | ZBTB3 | exon,utr3 |
| 219249 | >chr1 | 20981241 | 20981265 | Ax25 | EIF4G3 | intron |
| 140708 | >chr15 | 91749825 | 91749843 | GGTGGAx3.2 | - | - |
| 294364 | >chr22 | 50215636 | 50215648 | Gx13 | SELENOO | intron |
| 190482 | >chr18 | 42923771 | 42923785 | Ax15 | RIT2 | intron |
| 157082 | >chr16 | 68291763 | 68291800 | GTx19 | SLC7A6 | intron |
| 396133 | >chr4 | 47590977 | 47590987 | Gx11 | ATP10D | intron |
| 165557 | >chr17 | 13014291 | 13014313 | Ax23 | ELAC2 | intron |
| 348123 | >chr2 | 2.17E+08 | 216610286 | TTTTCx7.8 | - | - |
| 150981 | >chr16 | 31191378 | 31191394 | Tx17 | FUS | nc_intron,intron |
| 618786 | >chrX | 1.54E+08 | 154092169 | Ax13 | MECP2 | utr5,intron |
| 262754 | >chr1 | 2.47E+08 | 246805448 | AGCx6.3 | SMYD3 | intron |
| 340745 | >chr2 | 2.19E+08 | 219333140 | TAx20.5 | RESP18 | intron |
| 85798 | >chr12 | 1.3E+08 | 130273531 | TCCx6.7 | - | - |
| 209731 | >chr19 | 41577081 | 41577100 | ACx10 | CEACAM21 | utr5,intron |
| 215045 | >chr1 | 3836469 | 3836492 | Tx24 | CEP104 | intron |
| 403599 | >chr4 | 84773036 | 84773048 | Tx13 | WDFY3 | intron |
| 512875 | >chr7 | 77259940 | 77259997 | GTx29 | CCDC146 | intron |
| 456380 | >chr5 | 1.6E+08 | 160412553 | Ax30 | SLU7 | intron |
| 438303 | >chr5 | 69400209 | 69400231 | TTTAx5.8 | RAD17 | intron |
| 409129 | >chr4 | 1.13E+08 | 112653334 | Tx12 | LARP7 | nc_intron,intron |
| 396864 | >chr4 | 52062187 | 52062204 | Tx18 | SPATA18 | utr5,nc_intron,intron |

Fig. 19 (cont.)

| micro | chrom | start_pos | stop_pos | micro_unit | gene | feature |
|---|---|---|---|---|---|---|
| 283838 | >chr21 | 36719947 | 36719957 | Ax11 | SIM2 | intron |
| 244144 | >chr1 | 1.6E+08 | 160195663 | Cx11 | CASQ1 | intron |
| 242626 | >chr1 | 1.54E+08 | 153645049 | Tx15 | CHTOP | intron |
| 440059 | >chr5 | 79088359 | 79088398 | TGx20 | BHMT2 | intron |
| 12155 | >chr10 | 50124870 | 50124881 | ATx6 | WASHC2A | intron |
| 181539 | >chr17 | 80822939 | 80822950 | GTx6 | RPTOR | cds |
| 166663 | >chr17 | 17793780 | 17793820 | CAGx13.7 | RAI1 | utr5,exon |
| 309695 | >chr2 | 66435744 | 66435767 | Tx24 | MEIS1 | exon,utr3 |
| 198725 | >chr19 | 1257518 | 1257538 | TCCx7 | MIDN | intron |
| 115277 | >chr14 | 61528974 | 61529006 | GTx16.5 | PRKCH | intron |
| 131436 | >chr15 | 49795631 | 49795651 | AGTTCCx3.5 | - | - |
| 37477 | >chr11 | 36403464 | 36403479 | Tx16 | PRR5L | intron |
| 185861 | >chr18 | 21540014 | 21540032 | ATx9.5 | ESCO1 | intron |
| 330298 | >chr2 | 1.69E+08 | 169270891 | ACx10.5 | LRP2 | intron |
| 355198 | >chr3 | 47320036 | 47320052 | Tx17 | KLHL18 | intron |
| 143916 | >chr16 | 4407278 | 4407290 | Ax13 | CORO7 | utr5,nc_intron,intron |
| 41811 | >chr11 | 61958128 | 61958142 | TCCx5 | BEST1 | nc_intron,intron |
| 264470 | >chr20 | 5106079 | 5106120 | ACx21 | TMEM230 | intron |
| 347719 | >chr3 | 9909355 | 9909374 | ACx10 | IL17RE | nc_intron,intron |
| 246991 | >chr1 | 1.74E+08 | 173850298 | Ax15 | DARS2 | intron |
| 119697 | >chr14 | 80905756 | 80905768 | Ax13 | CEP128 | intron |
| 396101 | >chr4 | 47425481 | 47425519 | GATAx9.8 | GABRB1 | intron |
| 423800 | >chr4 | 1.85E+08 | 185176122 | Tx13 | CFAP97 | intron |

Fig. 19 (cont.)

| micro | chrom | start_pos | stop_pos | micro_unit | gene | feature |
|---|---|---|---|---|---|---|
| 92018 | >chr13 | 44943352 | 44943377 | ACx13 | NUFIP1 | intron |
| 270042 | >chr20 | 33015600 | 33015613 | Ax14 | BPIFB2 | intron |
| 268951 | >chr20 | 30215031 | 30215040 | Ax10 | - | - |
| 385947 | >chr4 | 952475 | 952518 | TGx22 | TMEM175 | intron |
| 435551 | >chr5 | 56652761 | 56652784 | AAAACx4.8 | SLC38A9 | nc_intron,intron |
| 6672 | >chr10 | 27145290 | 27145311 | Ax22 | YME1L1 | intron |
| 23047 | >chr10 | 1.01E+08 | 100505339 | ACx20 | SEC31B | intron |
| 51380 | >chr11 | 1.07E+08 | 107439056 | Ax21 | CWF19L2 | intron |
| 44676 | >chr11 | 739644766 | 739644813 | TGx24 | DNAJB13 | intron |
| 164048 | >chr17 | 7024701 | 7024730 | CAGx10 | BCL6B | cds |
| 427023 | >chr5 | 109815587 | 109981607 | ACx10.5 | CTNND2 | nc_intron,intron |
| 417356 | >chr4 | 1.54E+08 | 154374025 | Ax23 | DCHS2 | intron |
| 540000 | >chr8 | 429061146 | 429061155 | Cx10 | HOOK3 | intron |
| 71909 | >chr12 | 71626210 | 71626237 | ACx14 | ZFC3H1 | intron |
| 370822 | >chr3 | 1.27E+08 | 126505664 | AGGGx6.8 | UROC1 | intron |
| 425033 | >chr5 | 1278442 | 1278456 | CAx7.5 | TERT | intron |
| 59409 | >chr12 | 9420667 | 9420698 | AAGGx8 | DDX12P | nc_intron |
| 282901 | >chr21 | 32755128 | 32755143 | Ax16 | PAXBP1 | nc_intron,intron |
| 21620 | >chr10 | 93790080 | 93790094 | Tx15 | LGI1 | nc_intron,intron |
| 437293 | >chr5 | 64507682 | 64507694 | Ax13 | RGS7BP | intron |
| 356898 | >chr3 | 54879328 | 54879341 | Tx14 | CACNA2D3 | nc_intron,intron |
| 235266 | >chr1 | 93129559 | 93129578 | Tx20 | MTF2 | intron |

Fig. 19 (cont.)

| micro | chrom | start_pos | stop_pos | micro_unit | gene | feature |
|---|---|---|---|---|---|---|
| 484351 | >chr6 | 1.11E+08 | 111008035 | Tx17 | RPF2 | intron |
| 297340 | >chr2 | 9518260 | 9518281 | Ax22 | ADAM17 | intron |
| 566833 | >chr9 | 306890088 | 30689105 | Ax18 | - | - |

Fig. 19 (cont.)

| micro | chrom | start_pos | stop_pos | micro_unit | gene | feature |
|---|---|---|---|---|---|---|
| 340123 | >chr2 | 2.17E+08 | 2.17E+08 | TTTTCx7.8 | - | - |
| 158733 | >chr16 | 75234097 | 75234113 | ACx8.5 | BCAR1 | intron |
| 437293 | >chr5 | 64507682 | 64507694 | Ax13 | RGS7BP | intron |
| 23937 | >chr10 | 1.04E+08 | 1.04E+08 | Tx14 | COL17A1 | intron |
| 416763 | >chr4 | 1.52E+08 | 1.52E+08 | Tx16 | FAM160A1 | exon,utr3 |
| 164048 | >chr17 | 7024701 | 7024730 | CAGx10 | BCL6B | cds |
| 216250 | >chr1 | 89466030 | 89466056 | CTTx9 | CA6 | intron |
| 119697 | >chr14 | 80905756 | 80905768 | Ax13 | CEP128 | intron |
| 9032 | >chr10 | 36522760 | 36522794 | GTx17.5 | - | - |
| 310093 | >chr2 | 68217012 | 68217040 | ACx14.5 | PPP3R1 | intron |
| 190482 | >chr18 | 42923771 | 42923785 | Ax15 | RIT2 | intron |
| 383947 | >chr3 | 1.9E+08 | 1.9E+08 | Tx16 | - | - |
| 440059 | >chr5 | 79088359 | 79088398 | TGx20 | BHMT2 | intron |
| 242677 | >chr1 | 1.54E+08 | 1.54E+08 | GTx9 | INTS3 | intron |
| 442521 | >chr5 | 91149985 | 91150025 | TTCTTTx6.8 | ADGRV1 | nc_intron,intron |
| 215045 | >chr1 | 3836469 | 3836492 | Tx24 | CEP104 | intron |
| 177366 | >chr17 | 64504983 | 64504996 | TCx7 | DDX5 | intron |
| 483292 | >chr6 | 1.07E+08 | 1.07E+08 | CAx16.5 | CRYBG1 | intron |
| 181539 | >chr17 | 80822939 | 80822950 | GTx6 | RPTOR | intron |
| 6672 | >chr10 | 271145290 | 271145311 | Ax22 | YME1L1 | intron |
| 472386 | >chr6 | 49470141 | 49470153 | Tx13 | CENPQ | utr5,intron |
| 6445 | >chr10 | 26223687 | 26223728 | GTx21 | GAD2 | intron |
| 242626 | >chr1 | 1.54E+08 | 1.54E+08 | Tx15 | CHTOP | intron |

Fig. 20

| micro | chrom | start_pos | stop_pos | micro_unit | gene | feature |
|---|---|---|---|---|---|---|
| 92018 | >chr13 | 44943352 | 44943377 | ACx13 | NUFIP1 | intron |
| 425033 | >chr5 | 1278442 | 1278456 | CAx7.5 | TERT | intron |
| 264470 | >chr20 | 5106079 | 5106120 | ACx21 | TMEM230 | intron |
| 270842 | >chr20 | 33015600 | 33015613 | Ax14 | BPIFB2 | intron |
| 386985 | >chr4 | 60844968 | 60844994 | Ax27 | JAKMIP1 | intron |
| 134687 | >chr15 | 64395361 | 64395385 | TGx12.5 | TRIP4 | utr5,nc_intron,intron |
| 294364 | >chr22 | 50215636 | 50215648 | Gx13 | SELENOO | intron |
| 409129 | >chr4 | 1.13E+08 | 1.13E+08 | Tx12 | LARP7 | nc_intron,intron |
| 396864 | >chr4 | 52062187 | 52062204 | Tx18 | SPATA18 | utr5,nc_intron,intron |
| 402100 | >chr4 | 77773174 | 77773189 | Ax16 | CNOT6L | intron |
| 139193 | >chr15 | 85123338 | 85123386 | ACx24.5 | PDE8A | intron |
| 143916 | >chr16 | 4407278 | 4407290 | Ax13 | CORO7 | utr5,nc_intron,intron |
| 407194 | >chr4 | 1.03E+08 | 1.03E+08 | ACx7.5 | SLC9B1 | nc_intron,intron |
| 185861 | >chr18 | 21540014 | 21540032 | ATx9.5 | ESCO1 | intron |
| 166663 | >chr17 | 17793780 | 17793820 | CAGx13.7 | RAI1 | cds |
| 268951 | >chr20 | 30215031 | 30215040 | Ax10 | - | - |
| 270222 | >chr20 | 33623955 | 33623983 | Ax29 | CBFA2T2 | intron |
| 504566 | >chr7 | 37033493 | 37033506 | Ax14 | ELMO1 | intron |
| 400945 | >chr4 | 71755149 | 71755177 | TATTx7.3 | GC | intron |
| 140708 | >chr15 | 91749825 | 91749843 | GGTGGAx3.2 | - | - |

Fig. 20 (cont.)

| ID | Top Networks | Score |
|---|---|---|
| 1 | Cell Cycle, DNA Replication, Recombination, and Repair, Cellular Growth and Proliferation | 25 |
| 2 | Cancer, Endocrine System Disorders, Organismal Injury and Abnormalities | 21 |
| 3 | Cellular Development, Cell Death and Survival, Cancer | 19 |
| 4 | Cell Death and Survival, Cancer, Organismal Injury and Abnormalities | 15 |
| 5 | Cancer, Cell Death and Survival, Cellular Development | 2 |

| ID | Diseases and Disorders | p-value | #Molecules |
|---|---|---|---|
| 1 | Cancer | 4.97E-02 - 8.44E-08 | 113 |
| 2 | Dermatological Diseases and Conditions | 4.67E-02 - 8.44E-08 | 78 |
| 3 | Organismal Injury and Abnormalities | 4.97E-02 - 8.44E-08 | 114 |
| 4 | Neurological Disease | 4.83E-02 - 1.02E-06 | 29 |
| 5 | Developmental Disorder | 4.67E-02 - 7.14E-05 | 19 |

| ID | Molecular and Cellular Functions | p-value | #Molecules |
|---|---|---|---|
| 1 | Cell Cycle | 4.67E-02 - 2.09E-04 | 14 |
| 2 | Cell Morphology | 4.67E-02 - 3.47E-04 | 12 |
| 3 | DNA Replication, Recombination, and Repair | 4.67E-02 - 5.19E-04 | 9 |
| 4 | Cellular Assembly and Organization | 4.67E-02 - 7.80E-04 | 19 |
| 5 | Cellular Function and Maintenance | 4.67E-02 - 1.49E-03 | 17 |

| ID | Top Canonical Pathways | p-value |
|---|---|---|
| 1 | Autophagy | 4.09E-03 |
| 2 | DNA damage-induced 14-3-3 Signaling | 5.63E-03 |
| 3 | mTOR Signaling | 6.52E-03 |
| 4 | Asparagine Degradation | 1.19E-02 |
| 5 | Glutamate Dependent Acid Resistance | 1.19E-02 |

Fig. 21

| cBioportal Medulloblastoma Study | % of cases Mutations |
|---|---|
| MBL (Sick kids 2016) | 39.1% of 46 tumors |
| MBL (PCGP) | 16.2% of 37 tumors |
| MB(Broad) | 6.5% of 92 tumors |
| MB(ICGC) | 6.4% of 125 tumors |
| NB(Cologne 2015) | 7% of 56 tumors |
| NB(AMC) | 2% of 87 tumors |

Fig. 22

| Gene A | Gene B | p-Value | Log Odds Ratio | Association |
|---|---|---|---|---|
| ELAC2 | ADAM17 | <0.001 | >3 | Co-occurrence |
| ELAC2 | ACACA | <0.001 | >3 | Co-occurrence |
| ADAM17 | ACACA | <0.001 | >3 | Co-occurrence |
| ADGRV1 | CTNND2 | <0.001 | >3 | Co-occurrence |
| MIDN | BEST1 | 0.022 | >3 | Co-occurrence |
| CCDC146 | COL17A1 | 0.022 | >3 | Co-occurrence |
| CCDC146 | KLHL1 | 0.022 | >3 | Co-occurrence |
| CCDC146 | ESCO1 | 0.022 | >3 | Co-occurrence |
| CCDC146 | FRYL | 0.022 | >3 | Co-occurrence |
| CCDC146 | TERT | 0.022 | >3 | Co-occurrence |
| CCDC146 | TNS1 | 0.022 | >3 | Co-occurrence |
| CCDC146 | LRP2 | 0.022 | >3 | Co-occurrence |
| CCDC146 | ANKRD30B | 0.022 | >3 | Co-occurrence |
| COL17A1 | KLHL1 | 0.022 | >3 | Co-occurrence |
| COL17A1 | ESCO1 | 0.022 | >3 | Co-occurrence |
| COL17A1 | FRYL | 0.022 | >3 | Co-occurrence |
| COL17A1 | TERT | 0.022 | >3 | Co-occurrence |
| COL17A1 | TNS1 | 0.022 | >3 | Co-occurrence |
| COL17A1 | LRP2 | 0.022 | >3 | Co-occurrence |
| COL17A1 | ANKRD30B | 0.022 | >3 | Co-occurrence |

Fig. 23

| Gene A | Gene B | p-Value | Log Odds Ratio | Association |
|---|---|---|---|---|
| KLHL1 | ESCO1 | 0.022 | >3 | Co-occurrence |
| KLHL1 | FRYL | 0.022 | >3 | Co-occurrence |
| KLHL1 | TERT | 0.022 | >3 | Co-occurrence |
| KLHL1 | TNS1 | 0.022 | >3 | Co-occurrence |
| KLHL1 | LRP2 | 0.022 | >3 | Co-occurrence |
| KLHL1 | ANKRD30B | 0.022 | >3 | Co-occurrence |
| ESCO1 | FRYL | 0.022 | >3 | Co-occurrence |
| ESCO1 | TERT | 0.022 | >3 | Co-occurrence |
| ESCO1 | TNS1 | 0.022 | >3 | Co-occurrence |
| ESCO1 | LRP2 | 0.022 | >3 | Co-occurrence |
| ESCO1 | ANKRD30B | 0.022 | >3 | Co-occurrence |
| TNRC6C | EIF4G3 | 0.022 | >3 | Co-occurrence |
| RAI1 | TMEM175 | 0.022 | >3 | Co-occurrence |
| RAI1 | HOOK3 | 0.022 | >3 | Co-occurrence |
| RAI1 | GABRB1 | 0.022 | >3 | Co-occurrence |
| RAI1 | ASRGL1 | 0.022 | >3 | Co-occurrence |
| RAI1 | CFAP97 | 0.022 | >3 | Co-occurrence |
| FRYL | TERT | 0.022 | >3 | Co-occurrence |
| FRYL | TNS1 | 0.022 | >3 | Co-occurrence |

Fig. 23 (cont.)

| Gene A | Gene B | p-Value | Log Odds Ratio | Association |
|---|---|---|---|---|
| FRYL | LRP2 | 0.022 | >3 | Co-occurrence |
| FRYL | ANKRD30B | 0.022 | >3 | Co-occurrence |
| TMEM175 | HOOK3 | 0.022 | >3 | Co-occurrence |

Fig. 23 (cont.)

METHODS AND SYSTEMS FOR MICROSATELLITE ANALYSIS

CROSS-REFERENCE

This application claims the benefit of U.S. Provisional Patent Application No. 62/837,109, filed Apr. 22, 2019, and PCT/US2020/029145, filed Apr. 21, 2020, which are incorporated by reference herein in its entirety.

BACKGROUND

Microsatellites (MSs) and their alteration and instability can be a genetic driving force behind numerous complex multigenic health states, including cancer, neurological diseases, or cardiovascular diseases. Presently, predicting, detecting, diagnosing, and characterizing these health states through microsatellites can involve matching the patient's microsatellite profile to databases of microsatellites associated with these health states. Such approach can be applicable only at later stages of the progression of the health state, which can lead to unreliability and difficulty in detection, prognosis, diagnosis, selection of treatment and treatment outcome. Therefore, there remains a need for improved methods of predicting, detecting, and characterizing these health states at both early and late stages through the analysis of microsatellite loci.

SUMMARY

In an aspect, the present disclosure provides a computer-implemented method for constructing an optimized classifier for a condition, the method comprising ranking subsets of the plurality of microsatellites as classifiers for the condition in a plurality of optimization cycles, wherein the subsets of the plurality of microsatellites comprise microsatellites in an initial population of microsatellites correlated with the condition, thereby identifying an optimized subset of the subsets of the plurality of microsatellites as the optimized classifier for the condition. In some aspects, the computer-implemented method further comprises comparing microsatellites in a first set of samples from subjects with the condition and microsatellites in a second set of samples from subjects without the condition, thereby identifying the initial population of microsatellites.

The ranking can comprise comparing microsatellites in a first set of samples from subjects with the condition and microsatellites in a second set of samples from subjects without the condition, thereby identifying the initial population of microsatellites. The computer-implemented method can comprise an initialization, wherein the initialization comprises randomly choosing a population of initial subsets of microsatellites from the initial population of microsatellites for use in ranking in an optimization cycle of the plurality of optimization cycles. A population of at least about 100 subsets of the initial population of microsatellites can be used in the plurality of optimization cycles. A minimum number of microsatellites in a subset of the subsets of microsatellites can be 8. A maximum number of microsatellites in a subset of the subsets of microsatellites can be 64. In some cases, duplicate microsatellites are not allowed in a subset of the subsets of microsatellites. The ranking can comprise performing a receiver operating characteristic (ROC) analysis using (i) the subsets of microsatellites, (ii) microsatellites in samples from subjects with the condition, and (iii) microsatellites in samples from subjects without the condition. The ranking in an optimization cycle of the plurality of optimization cycles can comprise determining a sum of sensitivity and specificity of microsatellites in each subset of the subsets as the classifier for the condition. An optimization cycle of the plurality of optimization cycles can comprise adding 10 new subsets of the initial population of microsatellites to subsets from a previous optimization cycle of the plurality of optimization cycles. Seven of the 10 new subsets can be generated by randomly splitting and recombining 2 randomly chosen subsets from the previous optimization cycle, and 3 of the 10 new subsets can be generated by randomly selecting microsatellites from the initial population of microsatellites. The method can further comprise discarding 10 subsets of the subsets in the optimization cycle based at least in part on having a lowest ranking in the optimization cycle. In some cases, the condition can be a presence or absence of a health state in a subject. The condition can be an increased or decreased likelihood of developing a health state in a subject. The condition can be an increased or decreased likelihood of a subject benefitting from a treatment of a health state. In some cases, the condition can be an increased or decreased likelihood of a subject having an increased risk for adverse effects from a treatment of a health state. The condition can be responsiveness of a subject to a treatment for a health state. In some cases, the condition can be prognosis of a health state in a subject. In some cases, the health state can be cancer. The cancer can be lung cancer. In other cases, the health state can be a neurological disease or a cardiovascular disease.

In another aspect, the present disclosure provides a computer-implemented method comprising determining a value of a classifier for a condition from a sample from a subject using a plurality of parameters, wherein each parameter of the plurality of parameters is a statistical measure of a correlation of each of a plurality of microsatellites from samples from subjects with the condition and/or samples from subjects without the condition.

The plurality of weights can comprise a plurality of optimal weights. In some aspects, the computer-implemented method can comprise determining the plurality of optimal weights. Determining the plurality of optimal weights can comprise applying a standard regression analysis to the plurality of weights. Determining the plurality of optimal weights can comprise use of a genetic algorithm. Determining the classifier can comprise using minor allele frequency data. The plurality of microsatellites can comprise at least 10 microsatellites. In some instance, each of the plurality of microsatellites is correlated with presence of the condition. The value of the classifier can further comprises comparing the classifier to a threshold. In some aspects, the condition can be a presence or absence of a health state in a subject, an increased or decreased likelihood of developing a health state in a subject, an increased or decreased likelihood of a subject benefitting from a treatment of a health state, an increased or decreased likelihood of a subject having an increased risk for adverse effects from a treatment of a health state, responsiveness of a subject to a treatment for a health state, or a combination thereof. In some cases, the health state is cancer, cardiovascular disease or a neurological disease. When the health state is cancer, the cancer can be lung cancer.

In another aspect, the present disclosure provides a computer-implemented method of determining a genomic age for a subject, the method comprising: determining a microsatellite minor allele characteristic in a first sample from a subject; processing the microsatellite minor allele characteristic with a reference; and determining the genomic age for the subject based on the processing.

In some cases, the processing comprises comparing the microsatellite minor allele characteristic to the reference. The minor allele characteristic can be a number of minor alleles at a genetic locus. The number of minor alleles can be supported by at least three next-generation sequencing sequence reads. The minor allele characteristic can be a total number of reads of minor alleles normalized to a total number of reads of primary alleles at a genetic locus. The method can further comprise performing next-generation sequencing of the first sample from the subject to generate sequence reads of microsatellites of the subject. The first sample can comprise blood, saliva, or tumor. The method can further comprise, after determining a first genomic age, determining a minor allele characteristic in a second sample from the subject. The method can comprise assessing the minor allele characteristic in the first sample from the subject and the minor allele characteristic in the second sample from the subject, and determining a rate of genomic aging of the subject based on the assessing.

In another aspect, the present disclosure provides a computer-implemented method, comprising: determining a plurality of classifiers for a sample from a subject using microsatellites in the sample from the subject; processing the plurality of classifiers with a plurality of reference classifiers for a plurality of conditions; and based on the processing, determining at least one condition, for the subject, from among the plurality of conditions.

The processing can comprise comparing the plurality of classifiers to the plurality of reference classifiers for the plurality of conditions. In some cases, the at least one condition of the plurality of conditions comprises a presence or absence of at least one health state from among a plurality of health states of the subject. In some cases, the at least one condition of the plurality of conditions comprises an increased or decreased likelihood of developing at least one health state from among a plurality of health states of the subject. The at least one condition of the plurality of the conditions can comprise an increased or decreased likelihood of the subject benefitting from a treatment of at least one health state from among a plurality of health states of the subject. The at least one condition of the plurality of the conditions can comprise an increased or decreased likelihood of the subject having an increased risk for adverse effects from a treatment of at least one health state from among a plurality of health states of the subject. The at least one condition of the plurality of the conditions can comprise responsiveness of the subject to a treatment for at least one health state from among a plurality of health states of the subject. The plurality of health states can comprise a plurality of cancers, where the plurality of cancers comprises ovarian cancer, breast cancer, low grade glioma, glioblastoma, lung cancer, prostate cancer, or melanoma. In some cases, the plurality of health states can comprise a plurality of neurological diseases or a plurality of cardiovascular diseases.

In an aspect, the present disclosure provides a non-transitory computer-readable medium comprising executable instructions that, when executed by one or more processors, cause the one or more processors to perform a method for constructing an optimized classifier for a condition, the method comprising ranking subsets of the plurality of microsatellites as classifiers for the condition in a plurality of optimization cycles, wherein the subsets of the plurality of microsatellites comprise microsatellites in an initial population of microsatellites correlated with the condition, thereby identifying an optimized subset of the subsets of the plurality of microsatellites as the optimized classifier for the condition. The computer-implemented method can further comprise comparing microsatellites from a first set of samples from subjects with the condition and microsatellites from a second set of samples from subjects without the condition, thereby identifying the initial population of microsatellites.

The ranking can comprise comparing microsatellites in a first set of samples from subjects with the condition and microsatellites in a second set of samples from subjects without the condition, thereby identifying the initial population of microsatellites. The computer-implemented method can comprise an initialization, wherein the initialization comprises randomly choosing a population of initial subsets of microsatellites from the initial population of microsatellites for use in ranking in an optimization cycle of the plurality of optimization cycles. A population of at least about 100 subsets of the initial population of microsatellites can be used in the plurality of optimization cycles. A minimum number of microsatellites in a subset of the subsets of microsatellites can be 8. A maximum number of microsatellites in a subset of the subsets of microsatellites can be 64. In some embodiments, duplicate microsatellites are not allowed in a subset of the subsets of microsatellites. The ranking can comprise performing a receiver operating characteristic (ROC) analysis using (i) the subsets of microsatellites, (ii) microsatellites in samples from subjects with the condition, and (iii) microsatellites in samples from subjects without the condition. The ranking in an optimization cycle of the plurality of optimization cycles can comprise determining a sum of sensitivity and specificity of microsatellites in each subset of the subsets as the classifier for the condition. An optimization cycle of the plurality of optimization cycles can comprise adding 10 new subsets of the initial population of microsatellites to subsets from a previous optimization cycle of the plurality of optimization cycles. Seven of the 10 new subsets can be generated by randomly splitting and recombining 2 randomly chosen subsets from the previous optimization cycle, and 3 of the 10 new subsets can be generated by randomly selecting microsatellites from the initial population of microsatellites. The method can further comprise discarding 10 subsets of the subsets in the optimization cycle based at least in part on having a lowest ranking in the optimization cycle. The condition can be a presence or absence of a health state in a subject. The condition can be an increased or decreased likelihood of developing a health state in a subject. The condition can be an increased or decreased likelihood of a subject benefitting from a treatment of a health state. The condition can be an increased or decreased likelihood of a subject having an increased risk for adverse effects from a treatment of a health state. The condition can be responsiveness of a subject to a treatment for a health state. The condition can be prognosis of a health state in a subject. The health state can be cancer. The cancer can be lung cancer. The health state can be a neurological disease or a cardiovascular disease.

In another aspect, the present disclosure provides a non-transitory computer-readable medium comprising executable instructions that, when executed by one or more processors, cause the one or more processors to perform a method comprising determining a value of a classifier for a condition from a sample from a subject using a plurality of parameters, wherein each parameter of the plurality of parameters is a statistical measure of a correlation of each of a plurality of microsatellites from samples from subjects with the condition and/or samples from subjects without the condition.

The plurality of weights can comprise a plurality of optimal weights. The computer-implemented method can comprise determining the plurality of optimal weights. The determining the plurality of optimal weights can comprise applying a standard regression analysis to the plurality of weights. The determining the plurality of optimal weights can comprise use of a genetic algorithm. The determining the classifier can comprise using minor allele frequency data. The plurality of microsatellites can comprise at least 10 microsatellites. Each of the plurality of microsatellites can be correlated with presence of the condition. The value of the classifier can further comprise comparing the classifier to a threshold. The condition can be a presence or absence of a health state in a subject, an increased or decreased likelihood of developing a health state in a subject, an increased or decreased likelihood of a subject benefitting from a treatment of a health state, an increased or decreased likelihood of a subject having an increased risk for adverse effects from a treatment of a health state, responsiveness of a subject to a treatment for a health state, or a combination thereof. The health state can be cancer, cardiovascular disease, or a neurological disease. The cancer can be lung cancer.

In another aspect, the present disclosure provides a non-transitory computer-readable medium comprising executable instructions that, when executed by one or more processors, cause the one or more processors to perform a method of determining a genomic age for a subject, the method comprising: determining a microsatellite minor allele characteristic in a first sample from a subject; processing the microsatellite minor allele characteristic with a reference; and determining the genomic age for the subject based on the processing.

The processing can comprise comparing the microsatellite minor allele characteristic to the reference. The minor allele characteristic can be a number of minor alleles at a genetic locus. The number of minor alleles can be supported by at least three next-generation sequencing sequence reads. The minor allele characteristic can be a total number of reads of minor alleles normalized to a total number of reads of primary alleles at a genetic locus. The method can further comprise performing next-generation sequencing of the first sample from the subject to generate sequence reads of microsatellites of the subject. The first sample can comprise blood, saliva, or tumor. The method can further comprise, after determining a first genomic age, determining a minor allele characteristic in a second sample from the subject. The method can comprise assessing the minor allele characteristic in the first sample from the subject and the minor allele characteristic in the second sample from the subject, and determining a rate of genomic aging of the subject based on the assessing.

In another aspect, the present disclosure provides a non-transitory computer-readable medium comprising executable instructions that, when executed by one or more processors, cause the one or more processors to perform a method, the method comprising: determining a plurality of classifiers for a sample from a subject using microsatellites in the sample from the subject; processing the plurality of classifiers with a plurality of reference classifiers for a plurality of conditions; and based on the processing, determining at least one condition, for the subject, from among the plurality of conditions.

The processing can comprise comparing the plurality of classifiers to the plurality of reference classifiers for the plurality of conditions. The at least one condition of the plurality of conditions can comprise a presence or absence of at least one health state from among a plurality of health states of the subject. The at least one condition of the plurality of conditions can comprise an increased or decreased likelihood of developing at least one health state from among a plurality of health states of the subject. The at least one condition of the plurality of the conditions can comprise an increased or decreased likelihood of the subject benefitting from a treatment of at least one health state from among a plurality of health states of the subject. The at least one condition of the plurality of the conditions can comprise an increased or decreased likelihood of the subject having an increased risk for adverse effects from a treatment of at least one health state from among a plurality of health states of the subject. The at least one condition of the plurality of the conditions can comprise responsiveness of the subject to a treatment for at least one health state from among a plurality of health states of the subject. The plurality of health states can comprise a plurality of cancers, where the plurality of cancers can comprise ovarian cancer, breast cancer, low grade glioma, glioblastoma, lung cancer, prostate cancer, or melanoma. The plurality of health states can comprise a plurality of neurological diseases or a plurality of cardiovascular diseases.

Another aspect of the present disclosure provides a non-transitory computer-readable medium comprising machine-executable code that, upon execution by one or more computer processors, implements any of the methods above or elsewhere herein.

Another aspect of the present disclosure provides a system comprising one or more computer processors and computer memory coupled thereto. The computer memory comprises machine-executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7A illustrates a distribution of metric scores in a training cohort. FIG. 7C illustrates a distribution of metric scores in a validation cohort. ROC analysis was performed on training (120 MB subjects and the 425 control subjects) (FIG. 7B) and validation (102 MB subjects and 428 control subjects) cohorts (FIG. 7D).

FIG. 17 illustrates an example of an output of reporting the results of the microsatellite analysis by the computer-implemented methods to assess a subject's risk of developing cancer.

FIG. 19 illustrates a list of the 139 informative germline MSs associated with MB.

FIG. 20 illustrates a list of the 43 microsatellite loci in the MB signature set.

FIG. 21 illustrates Ingenuity Pathway analysis of informative MB MS loci.

FIG. 22 illustrates mutations in informative MB MS loci associated genes in cBioportal MB cohorts.

FIG. 23 illustrates an analysis of cBioportal MB cancer studies, which revealed that mutations in 135 gene pairs tend to significantly co-occur within MB cancer risk classifiers.

DETAILED DESCRIPTION

I. Overview

Figure 1:
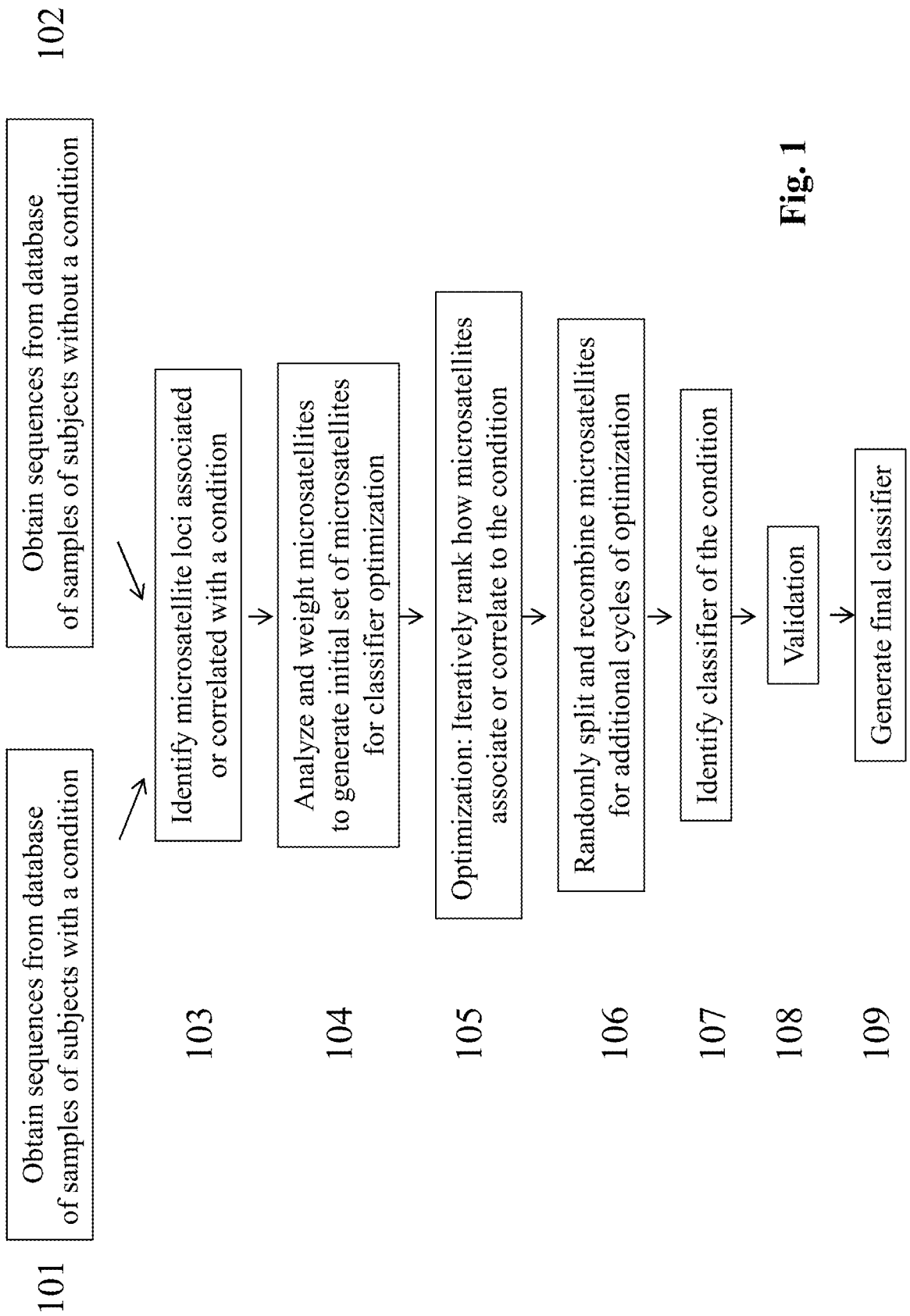
FIG. 1 illustrates an example of a work flow of computer-implemented methods for generating a microsatellite classifier.

The present disclosure provides computer-implemented methods of generating a classifier for a condition using, e.g., microsatellites. FIG. 1 illustrates an example of a work flow of how computer-implemented methods are performed to generate the classifier. Deoxyribonucleic acid (DNA) sequences are obtained from databases of sequence information from samples of subjects with a condition (101) and sequence information from reference subjects without the condition (102). Microsatellite loci from 101 and 102 are identified (genotyped) and compared to each other to reveal a population of microsatellites (103) that is only associated or correlated with the condition. The population of microsatellite loci are then further analyzed and weighted to arrive at an initial set of microsatellite loci (104) for optimization of a classifier (105). The optimization iteratively ranks how the microsatellites associate or correlate to the condition. The optimization can be repeated with additional sets of microsatellites for additional cycles of optimization. In some cases, the sets of microsatellites are randomly split and recombined to yield a new initial set of microsatellites (106) for the additional cycles of optimization. Upon completion of the optimization, the computer-implemented methods identify the sets of microsatellites (107) that can be most informative for generating the classifier. An additional validation or optimization step (108) can be taken by analyzing additional samples (e.g., from databases) of subjects with known presence or absence of the condition. After 108, the computer-implemented methods can be used to generate a final classifier (109).

In an aspect, the present disclosure provides improved computer-implemented methods for identifying a set of microsatellites as a marker (classifier) for a condition. The methods can further comprise comparing microsatellite loci from a first set of samples from subjects with the condition and microsatellite loci from a second set of samples from subjects without the condition, thereby identifying an initial population of microsatellite loci (informative loci).

In some cases, the informative loci can be directly used as classifiers. In some cases, the classifiers comprising the informative loci can be indicative of a presence or absence of the condition in the subject. In some cases, the classifiers comprising informative loci can indicate an increased or decreased likelihood of development of the condition in the subject. In some instances, the classifiers comprising informative loci can indicate that an increased or decreased likelihood of a subject benefitting from a treatment, or an increased or decreased likelihood of a subject having an increased risk for adverse effects as a result of a treatment. In some cases, the classifiers comprising informative loci can indicate responsiveness to a treatment for the condition of the subject. In some instances, the classifiers of informative loci can indicate prognosis of the condition in the subject.

In some aspects, the initial population of microsatellite loci (informative loci) is for use in genetic algorithm as performed by the computer-implemented methods. The methods can comprise iteratively ranking subsets of the initial population of microsatellites by comparing subsets of microsatellites in samples from subjects with the condition and microsatellites from samples from subjects without the condition. The methods can comprise an initialization in which initial subsets of the subsets are chosen at random from the initial population of microsatellite loci. In some instances, about 100 subsets of the initial population of microsatellite loci are used throughout the genetic algorithm (optimization cycles), where a minimum number of microsatellites in a subset of the subsets is 8 and a maximum number of microsatellites in a subset of the subsets is 64. In some instances, the iteratively ranking comprises a plurality of optimization cycles, where the plurality of optimization cycles comprises adding 10 new subsets of the initial population of microsatellites to subsets from a previous cycle of optimization. 7 of the 10 new subsets can be generated by randomly splitting and recombining 2 randomly chosen subsets from the previous cycle of optimization, and 3 of the 10 new subsets are generated by randomly selecting microsatellites from the initial population of microsatellites. In some cases, the methods comprise ranking subsets in the optimization cycle, wherein 10 of the subsets with a lowest ranking in the optimization cycle are discarded, thus maintaining the 100 subsets of population of microsatellites throughout the cycles of optimization. The genetic algorithm can comprise performing the iteratively ranking of all combination of microsatellites to identify the most informative microsatellite loci. The genetic algorithm can improve sensitivity and specificity by removing less informative microsatellite loci, and selecting or weighting for more informative microsatellite loci. In some cases, the condition identified by the microsatellite loci as optimized by the cycles can be indicative of a presence or absence of a health state in the subject, an increased or decreased likelihood of development of a health state in the subject, an increased or decreased likelihood of a subject benefitting from a treatment for a health state, an increased or decreased likelihood of a subject having an increased risk for adverse effects as a result of a treatment for a health state, subject's responsiveness to a treatment for a health state, prognosis of a health state of a subject, or a combination thereof.

In another aspect, the present disclosure provides improved computer-implemented methods comprising determining a classifier for a condition from a sample from a subject using a plurality of parameters, wherein each parameter of the plurality of parameters is a statistical measure of a correlation of each of a plurality of microsatellites from samples from subjects with a condition and/or samples from subjects without a condition. In some cases, the plurality of parameters comprises optimal weights, such as those determined by standard regression analysis and use of a genetic algorithm. In some cases, the classifier is determined by using minor allele frequency data. In some cases, the condition can indicate a presence or absence of a health state in a subject, an increased or decreased likelihood of development of a health state in a subject, an increased or decreased likelihood of a subject benefitting from a treatment for a health state, an increased or decreased likelihood of a subject having an increased risk for adverse effects as a result of a treatment for a health state, subject's responsiveness to a treatment for a health state, prognosis of a health state of a subject, or a combination thereof. In some cases, the health state is cancer, neurological disease, or cardiovascular disease.

In another aspect, the present disclosure provides methods of using a computer system for determining a minor allele characteristic in a first sample from a subject, comparing the minor allele characteristic to a reference, and determining a genomic age for the subject based on the comparing. The minor allele characteristic can be a number of minor alleles at a locus, where the number of alleles is supported by at least one, at least two, at least three, or more than three next-generation sequencing sequence reads. In some cases, the minor allele characteristic is a total number of reads of minor alleles normalized to a total number of reads of primary alleles at a locus. The minor allele characteristic from a first sample from a subject can be compared to a second minor allele characteristic in a second sample from the same subject to determine a rate of genomic aging.

The present disclosure provides a pan-condition assay based on classifiers generated using microsatellite loci and, optionally, minor allele information. In some cases, the pan-condition assay is a pan-cancer assay.

The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. About can mean +/−10%, +/−5%, +/−2%, or +/−1% of a value. As used in the specification and claims, the singular form "a", "an", and "the" include plural references unless the context clearly dictates otherwise. For example, the term "a nucleic acid" includes a plurality of nucleic acids, including mixtures thereof.

II. Methods of Determining Microsatellite Classifiers of a Condition

The present disclosure provides methods, e.g., computer-implemented methods (see e.g., FIG. 2), and systems for identifying microsatellite classifiers for a condition. The condition can be a presence or absence of a health state in the subject, an increased or decreased likelihood of development of a health state in the subject, an increased or decreased likelihood of a subject benefitting from a treatment for a health state, an increased or decreased likelihood of a subject having an increased risk for adverse effects as a result of a treatment for a health state, subject's responsiveness to a treatment for a health state, prognosis of a health state of a subject, or a combination thereof. The methods can comprise identifying microsatellite loci (genotyping) in samples from subjects with a condition and without a condition. The methods can comprise identifying statistically informative microsatellite loci for a condition. The methods can comprise using the statistically informative microsatellite loci to develop a classification signature for a condition. The classification signature can be validated and used to test samples from subjects.

A. Genotyping Microsatellite Loci

The methods of identifying a microsatellite classifier can comprise genotyping microsatellite loci in samples from subject with a condition and without a condition. In some cases, the genotyping comprises analyzing sequence information in a database. In some cases, the genotyping comprises obtaining samples and analyzing nucleic acid molecules in the samples, e.g., by next-generation sequencing.

1. Databases of Sequence Information

In some cases, the methods of identifying (e.g., genotyping) microsatellite loci can comprise analyzing sequence information from one or more databases. The one or more databases can comprise sequence information (e.g., sequence reads) of nucleic acid samples from subjects with a condition, e.g., subjects with cancer or from cancer cell lines. The one or more databases can comprise reference sequences (e.g., a human genome or a portion thereof). The one or more databases can comprise sequences of variance or polymorphisms of a population or populations of subjects.

The one or more databases can comprise sequence information generated by high throughput or next-generation sequencing. The one or more databases can comprise sequence data (e.g., sequence read data) generated by whole exome sequencing (WES), whole genome sequencing (WGS), or a combination thereof, of samples from subjects. In certain instances, the one or more databases comprise sequence information (e.g., sequence read information) generated from targeted sequencing. The targeted sequencing can comprise enrichment of target sequences from a sample from a subject.

The database can comprise sequence information from The Cancer Genome Atlas (TCGA), e.g., exome data, e.g., lung cancer exome data. The database can be from the 1000 Genomes Project.

2. Samples

A sample can be a biological sample obtained or derived from one or more subjects. A sample can be processed or fractioned to produce other samples, e.g., other biological samples. A sample as described in the instant disclosure can include any material from which nucleic acid molecules can be obtained.

The sample can be obtained from a subject with a condition. The sample can be obtained from a subject with a symptom of a condition. The sample can be obtained from a subject with a condition, but the subject does not have a symptom of the condition. The sample can be obtained from a subject without a condition. The sample can be obtained from a subject with a cancer, from a subject that is suspected of having a cancer, or from a subject that does not have or is not suspected of having the cancer.

The samples can be obtained or derived from a human subject. The samples can be stored in a variety of storage conditions before processing, such as different temperatures (e.g., at room temperature, under refrigeration or freezer conditions, at 25° C., at 4° C., at −18° C., −20° C., or at −80° C.) or different suspensions (e.g., EDTA collection tubes, or cell-free DNA or RNA collection tubes).

The sample can be taken before and/or after treatment of a subject with the cancer. Samples can be obtained from a subject during a treatment or a treatment regime. Multiple samples can be obtained from a subject to monitor the effects of the treatment over time. The sample can be taken from a subject known or suspected of having a cancer for which a definitive positive or negative diagnosis is not available via clinical tests. The sample can be taken from a subject suspected of having a cancer. The sample can be taken from a subject experiencing unexplained symptoms, such as fatigue, nausea, weight loss, aches and pains, weakness, or bleeding. The sample can be taken from a subject having explained symptoms. The sample can be taken from a subject at risk of developing a cancer due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

A sample can be a biological sample from a subject. The sample can be whole blood, peripheral blood, plasma, serum, saliva, mucus, urine, semen, lymph, amniotic fluid, fecal extract, cheek swab, cells or other bodily fluid or tissue, including tissue obtained through surgical biopsy or surgical resection. In some cases, a sample can be a primary subject (e.g., patient) derived cell line or an archived subject (e.g., patient) sample, e.g., a preserved sample, e.g., a formalin fixed paraffin embedded (FFPE) sample, or fresh frozen sample. The sample, e.g., a biological sample, can be obtained or derived from a subject using an ethylenediaminetetraacetic acid (EDTA) collection tube, a DNA or RNA collection tube, or a cell-free DNA or cell-free RNA collection tube. The sample, e.g., biological sample, can be derived from a whole blood sample by fractionation. The sample, e.g., biological sample, or derivative thereof can comprise cells. The sample, e.g., biological sample, can be a blood sample or a derivative thereof (e.g., blood collected from a collection tube or blood drops).

The sample can contain one or more analytes capable of being assayed. The sample can comprise one or more nucleic acid molecules. The one or more nucleic acid molecules (or any nucleic acid molecule disclosed herein, including primers and probes) can be a polymeric form a nucleotides of any length, e.g., either deoxyribonucleotides (dNTPs) or ribonucleotides (rNTPs), or analogs thereof. The analogs can include non-naturally occurring bases, nucleotides that engage in linkages with other nucleotides other than the naturally occurring phosphodiester bond or which include bases attached through linkages other than phosphodiester bonds. Nucleotide analogs include, e.g., phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. The nucleic acid molecules can be deoxyribonucleic acid (DNA). The DNA can be genomic DNA, viral DNA, mitochondrial DNA, plasmid DNA, amplified DNA, circular DNA, circulating DNA, cell-free DNA, or exosomal DNA. In some instances, the DNA is single-stranded DNA (ssDNA), double-stranded DNA, denatured double-stranded DNA, synthetic DNA, and combinations thereof. The circular DNA can be cleaved or fragmented. The DNA can comprise a coding or non-coding region of a gene or gene fragment of interest, loci (locus) defined from linkage analysis, exon, or intron. The DNA can be complementary DNA (cDNA). The nucleic acid molecule can be a recombinant nucleic acid, branched nucleic acid, plasmid, vector, or isolated DNA. A nucleic acid molecule can comprise one or more modified nucleotides, e.g., methylated nucleotides or nucleotide analogs. Modifications to the nucleotide structure can be made before or after assembly of the nucleic acid molecule. A sequence of a nucleotides of a nucleic acid molecule can be interrupted by non-nucleotide components. A nucleic acid molecule can be further modified after polymerization, such as by conjugation or binding with a reporter agent.

The nucleic acid molecule can comprise a locus, genetic locus, or genomic region, which can be identified by its location in a genome or chromosome. In some examples, a locus can be referred to by a gene name and encompass coding and non-coding regions associated with that physical region of nucleic acid. A gene can comprise coding regions (exons), non-coding regions (introns), transcriptional control or other regulatory regions, and promoters. In another example, the genomic region can incorporate an intron or exon or an intron/exon boundary within a named gene.

In some instances, the nucleic acid molecules comprise ribonucleic acid (RNA). The RNA can be fragmented RNA. The RNA can be degraded RNA. The RNA can be microRNA or portion thereof. The RNA can be an RNA molecule or a fragmented RNA molecule (RNA fragments) selected from: a microRNA (miRNA), a pre-miRNA, a pri-miRNA, a messenger RNA (mRNA), a pre-mRNA, a short interfering RNA (siRNA), short-hairpin RNA (shRNA), a viral RNA, a viroid RNA, a virusoid RNA, circular RNA (circRNA), a ribosomal RNA (rRNA), a transfer RNA (tRNA), a pre-tRNA, a long non-coding RNA (lncRNA), a small nuclear RNA (snRNA), a circulating RNA, a cell-free RNA, an exosomal RNA, a vector-expressed RNA, an RNA transcript, a synthetic RNA, ribozyme, cell-free RNA, and combinations thereof.

In some cases, the sample comprises cell-free nucleic acid molecules. Cell-free nucleic acid molecules can include, for example, all non-encapsulated nucleic acid molecules sourced from a bodily fluid from a subject. A cell-free nucleic acid (cfNA) molecule can be a nucleic acid (e.g., cell-free RNA (cfRNA) molecule or cell-free DNA (cfDNA) molecule in a biological sample that is not contained in a cell. A cfDNA molecule can circulate freely in in a bodily fluid, such as in the bloodstream. The cell-free DNA molecule can be circulating tumor DNA, e.g., cfDNA originating from a tumor.

A sample can be a cell-free sample. A cell-free sample can be a biological sample that is substantially devoid of intact cells. The cell-free sample can be a biological sample that is itself substantially devoid of cells or can be derived from a sample from which cells have been removed. Examples of cell-free samples include those derived from blood, such as serum or plasma; urine; or samples derived from other sources, such as semen, sputum, feces, ductal exudate, lymph, or recovered lavage.

The sample can comprise germline nucleic acid molecules (e.g., nucleic acid from a non-diseased cell or tissue, e.g., tumor). The sample can comprise nucleic acid molecules from a tumor. In some cases, the sample can comprise germline nucleic acid molecules (e.g., from a non-diseased tissue) and nucleic acid molecules from a diseased tissue (e.g., a tumor).

The sample can comprise a target nucleic acid molecule. A target nucleic acid molecule can be a nucleic acid molecule having a nucleotide sequence whose presence, amount, and/or sequence, or changes in one or more of these, are desired to be determined.

Nucleic acid molecules (e.g., RNA or DNA) can be extracted from a sample, e.g., using Qiagen QIAmp DNA Blood Mini Kit, FastDNA Kit protocol from MP Biomedicals, or a cell-free biological DNA isolation kit protocol from Norgen Biotek. The extraction method can extract all RNA or DNA molecules from a sample. The extract method can selectively extract a portion of RNA or DNA molecules from a sample. Extracted RNA molecules from a sample can be converted to DNA molecules by reverse transcription (RT). Reverse transcription can be the generation of deoxyribonucleic acid (DNA) from a ribonucleic acid (RNA) template via the action of a reverse transcriptase.

The quality of the extracted nucleic acid can be analyzed, e.g., using BIOANALYZER or NANODROP systems.

A subject can be a person or individual. A subject can be a patient. The subject can be a person that has or is suspected of having cancer. The subject can display a symptom indicative of a health or physiological state or condition. The subject can be asymptomatic with respect to a health or physiological state or condition. A subject as described herein can include a mammal, including any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, e.g., rats, mice and guinea pigs, and the like. In one aspect, the mammal is a human.

Processing the sample obtained from the subject can comprise subjecting the sample to conditions that are sufficient to isolate, enrich, or extract a plurality of nucleic acid molecules, and assaying the plurality of nucleic acid molecules to generate the dataset.

A sample of the subject can be analyzed to genotype one or more microsatellites. Microsatellites, microsatellite loci, or microsatellite regions as described herein can refer to tandem repeats of from 1 to 6 nucleotides in a nucleotide sequence. In some cases, microsatellites comprise tandem repeats of more than 6 nucleotides. The one or more microsatellites can be found upstream of an exon, downstream of an exon, in an exon, in an intergenic sequence, in an intron, in a region spanning an exon and an intron, in a 3' untranslated region (UTR), in a 5' UTR, or any other region in a genome. In some instances, the pattern of the microsatellite of the sample is different from the pattern of the microsatellite in a reference. The difference of the pattern of a microsatellite can include single nucleotide polymorphisms (SNPs), percentage of SNPs, indels (insertion, deletion, ratio of insertion and deletion, and the combination thereof), or ratio of indels to SNPs. In some instances, the pattern of a difference in a microsatellite includes haplotyping, e.g., percentages of homozygosity, heterozygosity, or minor alleles at given loci. In the cases where the pattern of difference in a microsatellite are located in exonic regions, the difference can comprise non-synonymous SNPs, synonymous SNPs, frameshift indels, non-frameshift indels, stopgain, and stoploss. Samples can be matched, e.g., for age, gender, or ethnicity (e.g., Caucasians, African-Americans, Hispanic-Americans). In some cases, samples are not matched. In some cases, samples can be accompanied by additional clinical metadata, including for example health status, cancer, heart, or neurological status, therapy status or response, or disease stage. The clinical metadata can be correlated with microsatellites to determine whether the microsatellites are informative with respect to the clinical metadata.

The identities (e.g., genotypes) of one or more microsatellites can be obtained through any available methods or techniques, including next-generation sequencing, high-throughput sequencing, sequencing-by-synthesis, pyrosequencing, classic Sanger sequencing methods, sequencing-by-ligation, sequencing by synthesis, sequencing-by-hybridization, RNA-Seq (Illumina), ILLUMINA sequencing (using reversibly terminating nucleotides), paired-end sequencing, Digital Gene Expression (Helicos), single molecule sequencing, e.g., single molecule sequencing by synthesis (SMSS) (Helicos), Ion Torrent (semiconductor) Sequencing (Life Technologies/Thermo-Fisher), massively-parallel sequencing, clonal single molecule Array (Solexa), nanopore sequencing, Pacific Biosciences SMRT sequencing, shotgun sequencing, Maxim-Gilbert sequencing, primer walking, and any other sequencing methods.

The next-generation sequencing can comprise sample multiplexing. The sample multiplexing can be at least, or at most, or about 12 samples, 24 samples, 48 samples, 96 samples, 192 samples, 384 samples, 768 samples, or 1536 samples. The sequencing depth can from about 1× to about 10×, about 10× to about 100×, about 100× to about 500×, or about 500× to about 1000×.

The sequencing depth can be at least, at most, or about 1×, 5×, 10×, 50×, 100×, 200×, 250×, 300×, 400×, or 500×. Base calling consensus accuracy can be at least 95%, 96%, 97%, 98%, 99%, or more than about 99%. Quality score can be at least Q10 (e.g., less than 1:10 error rate, inferred base call accuracy of more than 90%), more than Q20 (e.g., less than 1:100 error rate, inferred base call accuracy of more than 99%), more than Q30 (e.g., less than 1:1000 error rate, inferred base call accuracy of more than 99.9%), more than Q40 (e.g., less than 1:10,000 error rate, inferred base call accuracy of more than 99.99%), or more than Q50 (e.g., less than 1:100,000 error rate, inferred base call accuracy of more than 99.999%). Assembly methods can yield at least 95%, 96%, 97%, 98%, or 99% accuracy for calling microsatellite genotypes in next-generation sequencing data sets.

After subjecting the nucleic acid molecules to sequencing, suitable bioinformatics processes can be performed on the sequence reads. For example, the sequence reads can be aligned to one or more reference genomes (e.g., a genome of one or more species such as a human genome). The aligned sequence reads can be quantified at one or more loci (e.g., one or more microsatellite loci).

In some aspects, identifying (e.g., genotyping) one or more microsatellites comprises amplifying the nucleotide sequence of one or more microsatellite loci, e.g., by performing polymerase chain reaction (PCR), e.g., using primers, e.g., specific primers, flanking the one or more microsatellite loci, and, e.g., evaluating the amplified fragment, e.g., by capillary electrophoresis or sequencing. The PCR can be quantitative PCR (qPCR), digital PCR, or reverse transcriptase PCR. The amplifying or amplification can increase the size or quantity of a nucleic acid molecule. The nucleic acid molecule that is amplified can be single-stranded or double-stranded. Amplification can include generating one or more copies or amplified product of the nucleic acid molecule. Amplification can be performed, for example, by extension (e.g., primer extension) or ligation. Amplification can include performing a primer extension reaction to generate a strand complementary to a single-stranded nucleic acid molecule, and in some cases generate one or more copies of the strand and/or the single-stranded nucleic acid molecule.

The amplification of nucleic acid molecules, e.g., nucleic acid molecules comprising the one or more microsatellite loci can be performed with any nucleic acid amplification method, e.g., loop mediated isothermal amplification (LAMP), nucleic acid sequence based amplification (NASBA), self-sustained sequence replication (3SR), rolling circle amplification (RCA), recombinase polymerase amplification (RPA), multiple displacement amplification (MDA), helicase-dependent amplification (HDA), strand displacement amplification (SDA), nicking enzyme amplification reaction (NEAR), exponential amplification reaction (EXPAR), polymerase spiral reaction (PSR), isothermal multiple displacement amplification (IMDA), ramification amplification method (RAM), single primer isothermal amplification (SPIA), signal-mediated amplification of RNA technology (SMART), beacon assisted detection amplification (BADAMP), hinge-initiated primer-dependent amplification of nucleic acids (HIP), smart amplification process (SmartAmp), hybridization chain reaction (HCR), a type of toehold-mediated strand displacement (TMSD), ligase chain reaction, digital PCR (dPCR), droplet digital PCR (ddPCR), or transcription-mediated amplification. The amplification can involve multiplex amplification, e.g., using AMPLISEQ. In some cases, RNA is converted into cDNA by reverse transcription before amplification. Assay readouts can comprise quantitative PCR (qPCR) values, digital PCR (dPCR) values, digital droplet PCR (ddPCR) values, fluorescence values, etc., or normalized values thereof. Other assays that can be used in the methods provided herein include immunoassays, electrochemical assays, surface-enhanced Raman spectroscopy (SERS), quantum dot (QD)-based assays, molecular inversion probes, CRISPR/Cas-based detection (e.g., CRISPR-typing PCR (ctPCR), specific high-sensitivity enzymatic reporter un-locking (SHERLOCK), DNA endonuclease targeted CRISPR trans reporter (DETECTR), CRISPR-mediated analog multi-event recording apparatus (CAMERA)), and laser transmission spectroscopy (LTS).

Multiplex amplification can comprise amplifying about 10 to about 50 targets, about 50 to about 100 targets, about 100 to about 500 targets, or about 500 to about 1000 targets. Adaptors can be added (e.g., ligated) to nucleic acid molecules to facilitate amplification and/or sequencing, e.g., on an ILLUMINA sequencing platform, e.g., universal adaptors. Universal primers can bind to the universal adaptors for amplification Multiple samples can be analyzed, and each multiplexed sample can be barcoded. RNA or DNA molecules isolated or extracted from a sample can be tagged, e.g., with identifiable tags, to allow for multiplexing of a plurality of samples. Any number of RNA or DNA samples can be multiplexed. For example a multiplexed reaction can contain RNA or DNA from at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more than 100 initial samples. For example, a plurality of samples can be tagged with sample barcodes such that each DNA molecule can be traced back to the sample (and the subject) from which the DNA molecule originated. Such tags can be attached to RNA or DNA molecules by ligation or by PCR amplification with primers.

In some cases, bait sets (e.g., hybridization probes, e.g., SURESELECT or SEQCAP) are used to acquire targets, e.g., target nucleic acid molecules. The targets can comprise RNA and/or DNA. The hybridization probes can be at least 15, 25, 50, 75, 100, 120, or 150 bases in length. The hybridization probes can be 15 to 50 bases, 50 to 100 bases, or 100 to 150 bases in length. The probes can be nucleic acid molecules (e.g., RNA or DNA) having sequence complementarity with nucleic acid sequences (e.g., RNA or DNA) of the one or more loci (e.g., one or more microsatellites). The assaying of the sample using probes that are selective for the one or more loci (e.g., one or more microsatellites) can comprise use of array hybridization (e.g., microarray-based), polymerase chain reaction (PCR), or nucleic acid sequencing (e.g., RNA sequencing or DNA sequencing).

In some aspects, analyzing nucleic acid molecules comprises performing next-generation sequencing. In some cases, sequencing of the microsatellite can be performed directly, e.g., without performing an amplification. Next-generation sequencing methods can encompass whole genome, whole exome, and partial genome or exome. Next-generation sequencing methods can be used on targeted sequences, enriched sequences, or a combination thereof.

In some instances, an enrichment is performed with enrichment kits prior to the sequencing and downstream analysis. In some cases, an enrichment is performed with enrichment kits to enrich for the microsatellite loci that are subjected to validation of the genetic algorithm. Using enrichment kits can increase the number of callable allelotypes or genotypes in a read, and can increase the ability to analyze a larger percentage of informative loci for a given sample. Enrichment kits can comprise an enrichment array or probes that hybridize to target sequence of a microsatellite and flanking sequences on either or both sides of the microsatellite. In some cases, the use of enrichment increases the number of callable genotypes by at least 5%, 10%, 20%, 30%, 40%, 50%, 60%, 70%, 80%, 90%, 100%, or more, as compared to the number of callable genotypes obtainable without use the enrichment kits. In some instances, the use of the enrichment kit increases the number of callable genotypes by a factor of at least 2, 3, 4, 5, 6, 7, 8, 9, 10 or more, as compared to the number of callable genotypes without using the enrichment kits. In some aspects, the enrichments kits disclosed herein comprise the compositions that can be used to perform the methods described herein.

3. Algorithms for Genotyping

Microsatellites can be genotyped using an algorithm. The algorithm can use, e.g., a Bayesian model selection guided by an empirically derived error model, or a Discretized Gaussian Mixture (e.g., GenoTan). The algorithm can be, e.g., Repeatseq. A dynamic programming based approach or heuristic method can be used to genotype microsatellites. Other tools for microsatellite genotyping include PHOBOS, MISA, Tandem Repeats Finder, FullSSR, or bMSISEA.

B. Identifying Informative Microsatellite

Identifying informative microsatellites can comprise identifying a first set of microsatellite loci from samples of subjects with a condition and a second set of microsatellite loci from samples of subjects without the condition. In some cases, the second set of microsatellite loci can be obtained from databases of reference sequences.

1. Statistics

A difference between the first set and second set of microsatellite loci can be detected and compared statistically with one or more statistical tests, such as t-test, Z-test, ANOVA, regression analysis, Mann-Whitney-Wilcoxon, Chi-squared test, correlation, Fisher's exact test, Bonferroni correction, and Benjamini-Hochberg test. In some cases, statistical differences are quantified using a generalized Fisher's exact test. In some cases, a Benjamini-Hochberg multiple testing correction is applied to control false discovery rate.

2. Microsatellite Filtering

The microsatellites can be filtered to control for any number of factors, e.g., age, ethnicity, gender, sequencing protocol (e.g., WSG, WES, or targeted sequencing), if e.g., the samples from subjects with a condition and samples from subjects without a condition are not matched for the factor. Microsatellites with potential bias can be excluded from subsequent analysis. Additional filters for filtering microsatellites can include length of the microsatellite repeat motif, the total length of the microsatellite (e.g., number of copies of the motif), the sequence of the motif (for example, using only those with high GC content), and on the purity of the microsatellite, e.g., if it has any bases that can interrupt a perfect set of copies of the motif. In some instances, the microsatellites can be filtered by their positions in the genome, e.g., exome, intron, intergenic regions, or untranslated regions. Filtering can include filtering by genes or functional elements that are in proximity to the microsatellites.

3. Scoring Samples

Statistical tests can yield a receiver operating characteristic (ROC) curve, where the area under the ROC curve is referred to as the area under the curve (AUC). The AUC can be determined to assess the accuracy of the comparison of the sets of microsatellite loci. A greater AUC can be indicative of higher accuracy of the association or correlation of the condition to the difference between the first set and second set of microsatellite loci. ROC curves can determine the rates of sensitively (e.g., true positives) and specificity (e.g., true negatives) for the association or correlation of the condition to the difference between the first set and second set of microsatellite loci. Sensitivity, also referred to as true positive rate, recall, or probability of detection, can measure the proportion of actual positives that are correctly identified as to the presence or absence of a condition. Sensitivity can quantify the avoidance of false negatives by calculating the number of true positives divided by the sum of number of true positives and number of false negatives. Specificity, also referred to as true negative rate, can measure the proportion of actual negatives that are correctly identified as to the presence or absence of a condition. Specificity can quantify the avoidance of false positives by calculating the number of true negatives divided by the sum of number of true negatives and number of false positives.

In some instances, the statistically significant association or correlation of the condition to the first set of microsatellite loci that are different from the second set of microsatellite loci has a statistical accuracy of at least 70%, 80%, 85%, 90%, 91%, 92%, 93%, 94%, 95%, 96%, 97%, 98%, or 99%. In some cases, the statistically significant association or correlation of the condition to the first set of microsatellite loci that are different from the second set of microsatellite loci has a statistical specificity of at least 0.70, 0.80, 0.85, 0.90, 0.91, 0.92, 0.93, 0.94, 0.95, 0.96, 0.97, 0.98, or 0.99 and a statistical sensitivity of at least 0.70, 0.80, 0.85, 0.90, 0.91, 0.92, 0.93, 0.94, 0.95, 0.96, 0.97, 0.98, or 0.99.

In some instances, identifying informative microsatellite comprises identifying a first set of microsatellite loci from a database comprising nucleic acid sequences obtained from subjects with a condition such as sequences of a type of cancer from The Cancer Genome Atlas Program (TCGA), and a second set of microsatellite loci from a reference database (e.g., hg19 or the 1000 Genome Project). A type of cancer, such as breast cancer, can be a subtype based on e.g., stage, morphology, histology, gene expression, receptor profile, mutation profile, aggressiveness, prognosis, malignant characteristics, etc. A type or cancer and subtype or cancer can be applied at a finer level, e.g., to differentiate one histological type of cancer or subtype of cancer e.g., defined according to mutation profile or gene expression. A cancer stage can refer to classification of cancer types based on histological and pathological characteristics relating to disease progression. In some instances, the sets of microsatellite loci are obtained from a database comprising nucleic acid sequences comprising nucleotide variants or polymorphisms. In some cases, the first set of microsatellite loci is obtained from samples with the condition and compared to a second set of microsatellite loci obtained from a database.

4. Conditions

In some cases, the condition associated or correlated to the difference of the sets of microsatellite loci can indicate a presence or absence of a health state in the subject, an increased or decreased likelihood of development of a health state in the subject, an increased or decreased likelihood of a subject benefitting from a treatment for a health state, an increased or decreased likelihood of a subject having an increased risk for adverse effects as a result of a treatment for a health state, subject's responsiveness to a treatment for a health state, prognosis of a health state of a subject, or a combination thereof. In some cases, the health state is cancer. In some cases, the cancer is solid or hematologic malignant. In certain cases, the cancer is metastatic, relapsed, or refractory. A cancer that can be associated or correlated with the different of the sets of the microsatellite loci includes acute myeloid leukemia (LAML or AML), acute lymphoblastic leukemia (ALL), adrenocortical carcinoma (ACC), bladder urothelial cancer (BLCA), brain stem glioma, brain lower grade glioma (LGG), brain tumor, breast cancer (BRCA), bronchial tumors, Burkitt lymphoma, cancer of unknown primary site, carcinoid tumor, carcinoma of unknown primary site, central nervous system atypical teratoid/rhabdoid tumor, central nervous system embryonal tumors, cervical squamous cell carcinoma, endocervical adenocarcinoma (CESC) cancer, childhood cancers, cholangiocarcinoma (CHOL), chordoma, chronic lymphocytic leukemia, chronic myelogenous leukemia, chronic myeloproliferative disorders, colon (adenocarcinoma) cancer (COAD), colorectal cancer, craniopharyngioma, cutaneous T-cell lymphoma, endocrine pancreas islet cell tumors, endometrial cancer, ependymoblastoma, ependymoma, esophageal cancer (ESCA), esthesioneuroblastoma, Ewing sarcoma, extracranial germ cell tumor, extragonadal germ cell tumor, extrahepatic bile duct cancer, gallbladder cancer, gastric (stomach) cancer, gastrointestinal carcinoid tumor, gastrointestinal stromal cell tumor, gastrointestinal stromal tumor (GIST), gestational trophoblastic tumor, glioblstoma multiforme glioma GBM), hairy cell leukemia, head and neck cancer (HNSD), heart cancer, Hodgkin lymphoma, hypopharyngeal cancer, intraocular melanoma, islet cell tumors, Kaposi sarcoma, kidney cancer, Langerhans cell histiocytosis, laryngeal cancer, lip cancer, liver cancer, Lymphoid Neoplasm Diffuse Large B-cell Lymphoma [DLBCL], malignant fibrous histiocytoma bone cancer, medulloblastoma, medullo epithelioma, melanoma, Merkel cell carcinoma, Merkel cell skin carcinoma, mesothelioma (MESO), metastatic squamous neck cancer with occult primary, mouth cancer, multiple endocrine neoplasia syndromes, multiple myeloma, multiple myeloma/plasma cell neoplasm, mycosis fungoides, myelodysplastic syndromes, myeloproliferative neoplasms, nasal cavity cancer, nasopharyngeal cancer, neuroblastoma, Non-Hodgkin lymphoma, nonmelanoma skin cancer, non-small cell lung cancer, oral cancer, oral cavity cancer, oropharyngeal cancer, osteosarcoma, other brain and spinal cord tumors, ovarian cancer, ovarian epithelial cancer, ovarian germ cell tumor, ovarian low malignant potential tumor, pancreatic cancer, papillomatosis, paranasal sinus cancer, parathyroid cancer, pelvic cancer, penile cancer, pharyngeal cancer, pheochromocytoma and paraganglioma (PCPG), pineal parenchymal tumors of intermediate differentiation, pineoblastoma, pituitary tumor, plasma cell neoplasm/multiple myeloma, pleuropulmonary blastoma, primary central nervous system (CNS) lymphoma, primary hepatocellular liver cancer, prostate cancer such as prostate adenocarcinoma (PRAD), rectal cancer, renal cancer, renal cell (kidney) cancer, renal cell cancer, respiratory tract cancer, retinoblastoma, rhabdomyosarcoma, salivary gland cancer, sarcoma (SARC), Sezary syndrome, skin cutaneous melanoma (SKCM), small cell lung cancer, small intestine cancer, soft tissue sarcoma, squamous cell carcinoma, squamous neck cancer, stomach (gastric) cancer, supratentorial primitive neuroectodermal tumors, T-cell lymphoma, testicular cancer testicular germ cell tumors (TGCT), throat cancer, thymic carcinoma, thymoma (THYM), thyroid cancer (THCA), transitional cell cancer, transitional cell cancer of the renal pelvis and ureter, trophoblastic tumor, ureter cancer, urethral cancer, uterine cancer, uterine cancer, uveal melanoma (UVM), vaginal cancer, vulvar cancer, Waldenstrom macroglobulinemia, or Wilm's tumor. In some aspects, the cancer type comprises acute lymphoblastic leukemia, acute myeloid leukemia, bladder cancer, breast cancer, brain cancer, cervical cancer, cholangiocarcinoma, colon cancer, colorectal cancer, endometrial cancer, esophageal cancer, gastrointestinal cancer, glioma, glioblastoma, head and neck cancer, kidney cancer, liver cancer, lung cancer, lymphoid neoplasia, melanoma, a myeloid neoplasia, ovarian cancer, pancreatic cancer, pheochromocytoma and paraganglioma, prostate cancer, rectal cancer, squamous cell carcinoma, testicular cancer, stomach cancer, or thyroid cancer.

In some cases, the health state is lung cancer or a subtype of lung cancer. A lung cancer that can be associated or correlated with the different of the sets of the microsatellite loci includes non-small cell lung cancer (NSCLC) (e.g., lung adenocarcinoma (LUAD), lung squamous cell carcinoma (LUSC), and large cell carcinoma), small cell lung cancer (SCLC), and lung carcinoid tumor.

In some cases, the health state is a neurological disease. Examples of neurological diseases that can be associated or correlated to the difference of the sets of microsatellite loci include myotonic dystrophy, fragile X-associated tremor/ataxia syndrome, spinocerebellar ataxias, Kennedy's disease, Huntington's disease, spinal-bulbar muscular atrophy, progressive myoclonus epilepsy 1 (Unverricht-Lundborg Disease), fragile X syndrome, fragile X E syndrome, dentatorubral-pallidoluysian atrophy, friedreich ataxia, oculopharyngeal muscular Dystrophy, fragile X-associated primary ovarian insufficiency, Huntington's Disease-Like 2, C9ORF72-Associated Frontotemporal Dementia, and amyotrophic lateral sclerosis. The health state can be autism.

In some cases, the health state is an inflammatory bowel disease (IBD), which can include gastrointestinal disorders of the gastrointestinal tract. Non-limiting examples of IBD include Crohn's disease (CD), ulcerative colitis (UC), indeterminate colitis (IC), microscopic colitis, diversion colitis, Behcet's disease, and other inconclusive forms of IBD. In some instances, IBD comprises fibrosis, fibrostenosis, stricturing and/or penetrating disease, obstructive disease, or a disease that is refractory (e.g., mrUC, refractory CD), perianal CD, or other complicated forms of IBD.

In some instances, the health state is a cardiovascular disease, which can include coronary heart disease (CAD), rheumatic heart disease, congenital heart disease, cardiomyopathy, tumors of the heart, vascular tumors, heart valve disease, disorders of the lining of the heart, stroke, aortic aneurysm, peripheral arterial disease, deep venous thrombosis (DVT), or pulmonary embolism.

In some cases, the health state is a metabolic disease or disorder, which can include acid-base imbalance, metabolic brain diseases, disorders of calcium metabolism, DNA repair-deficiency disorders, glucose metabolism disorders, hyperlactatemia, iron metabolism disorders, lipid metabolism disorders, malabsorption syndromes, metabolic syndrome X, inborn error of metabolism, mitochondrial diseases, phosphorus metabolism disorders, porphyrias, proteostasis deficiencies, metabolic skin diseases, wasting syndrome, or water-electrolyte imbalance.

In some cases, the health state is an autoimmune disease or disorder, which can include achalasia, Addison's disease, adult Still's disease, agammaglobulinemia, alopecia areata, amyloidosis, ankylosing spondylitis, anti-GBM/anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, autoimmune urticaria, axonal & neuronal neuropathy (AMAN), Baló disease, Behcet's disease, benign mucosal pemphigoid, bullous pemphigoid, Castleman disease (CD), celiac disease, Chagas disease, chronic inflammatory demyelinating polyneuropathy (CIDP), chronic recurrent multifocal osteomyelitis (CRMO), Churg-Strauss Syndrome (CSS) or Eosinophilic Granulomatosis (EGPA), cicatricial pemphigoid, Cogan's syndrome, cold agglutinin disease, congenital heart block, coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hidradenitis Suppurativa (HS) (Acne Inversa), hypogammalglobulinemia, IgA nephropathy, IgG4-related sclerosing disease, immune thrombocytopenic purpura (ITP), inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, lichen planus, lichen sclerosus, ligneous conjunctivitis, linear IgA disease (LAD), lupus, Lyme disease, Meniere's disease, microscopic polyangiitis (MPA), mixed connective tissue disease (MCTD), Mooren's ulcer, Mucha-Habermann disease, multifocal motor neuropathy (MMN) or MMNCB, multiple sclerosis, myasthenia gravis, myositis, narcolepsy, neonatal lupus, neuromyelitis optica, neutropenia, ocular cicatricial pemphigoid, pptic neuritis, palindromic rheumatism (PR), PANDAS, paraneoplastic cerebellar degeneration (PCD), paroxysmal nocturnal hemoglobinuria (PNH), parry Romberg syndrome, pars planitis (peripheral uveitis), Parsonage-Turner syndrome, pemphigus, peripheral neuropathy, perivenous encephalomyelitis, pernicious anemia (PA), POEMS syndrome, polyarteritis nodosa, polyglandular syndromes type I, II, III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjögren's syndrome, sperm & testicular autoimmunity, stiff person syndrome (SPS), subacute bacterial endocarditis (SBE), Susac's syndrome, sympathetic ophthalmia (SO), Takayasu's arteritis, temporal arteritis/giant cell arteritis, thrombocytopenic purpura (TTP), Tolosa-Hunt syndrome (THS), transverse myelitis, type 1 diabetes, ulcerative colitis (UC), undifferentiated connective tissue disease (UCTD), uveitis, vasculitis, vitiligo, or Vogt-Koyanagi-Harada Disease.

C. Developing a Classification Signature

Figure 2:
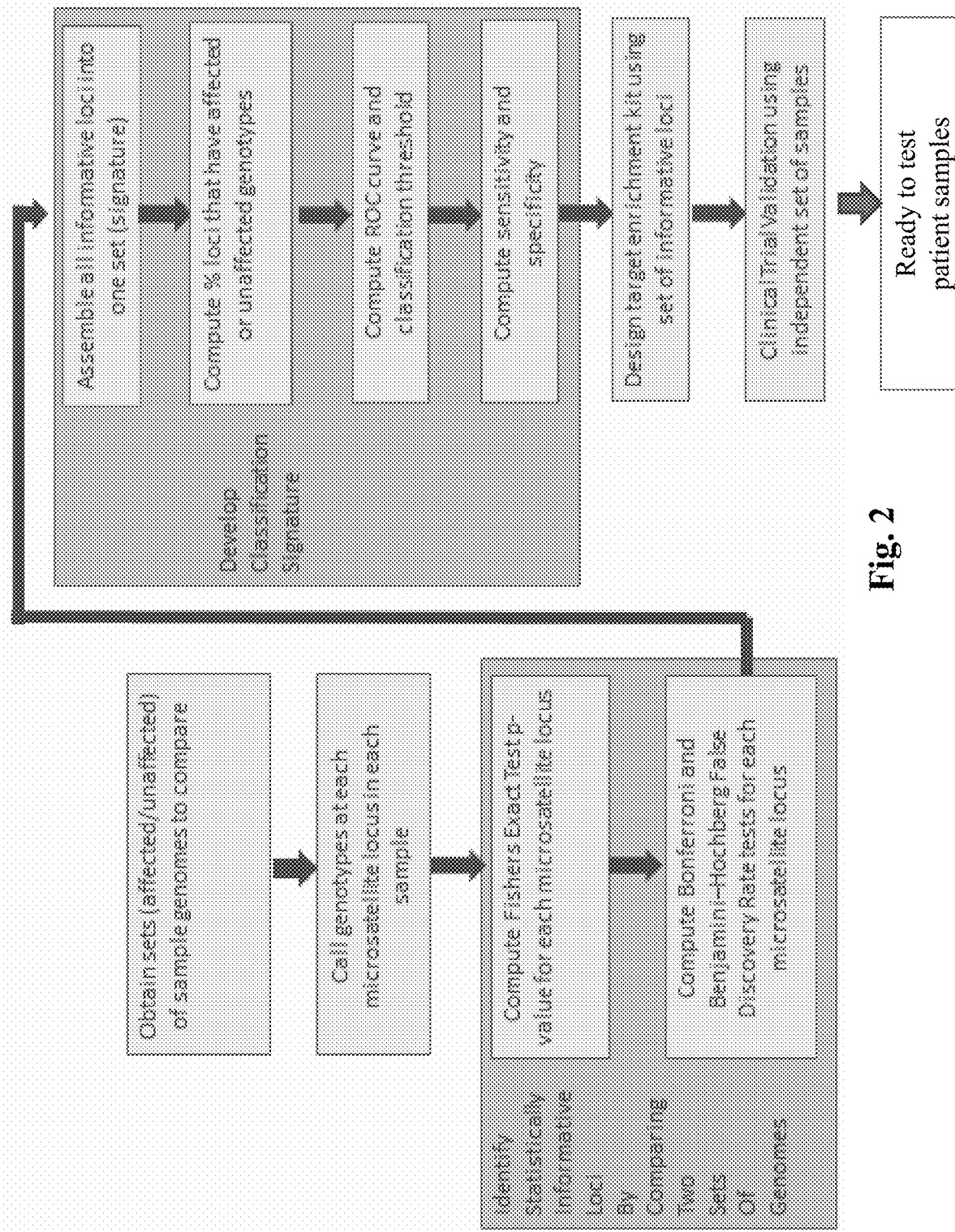
FIG. 2 illustrates an example of a development process using computer-implemented methods for identifying informative microsatellite loci and generating a classifier for a condition.
Figure 3:
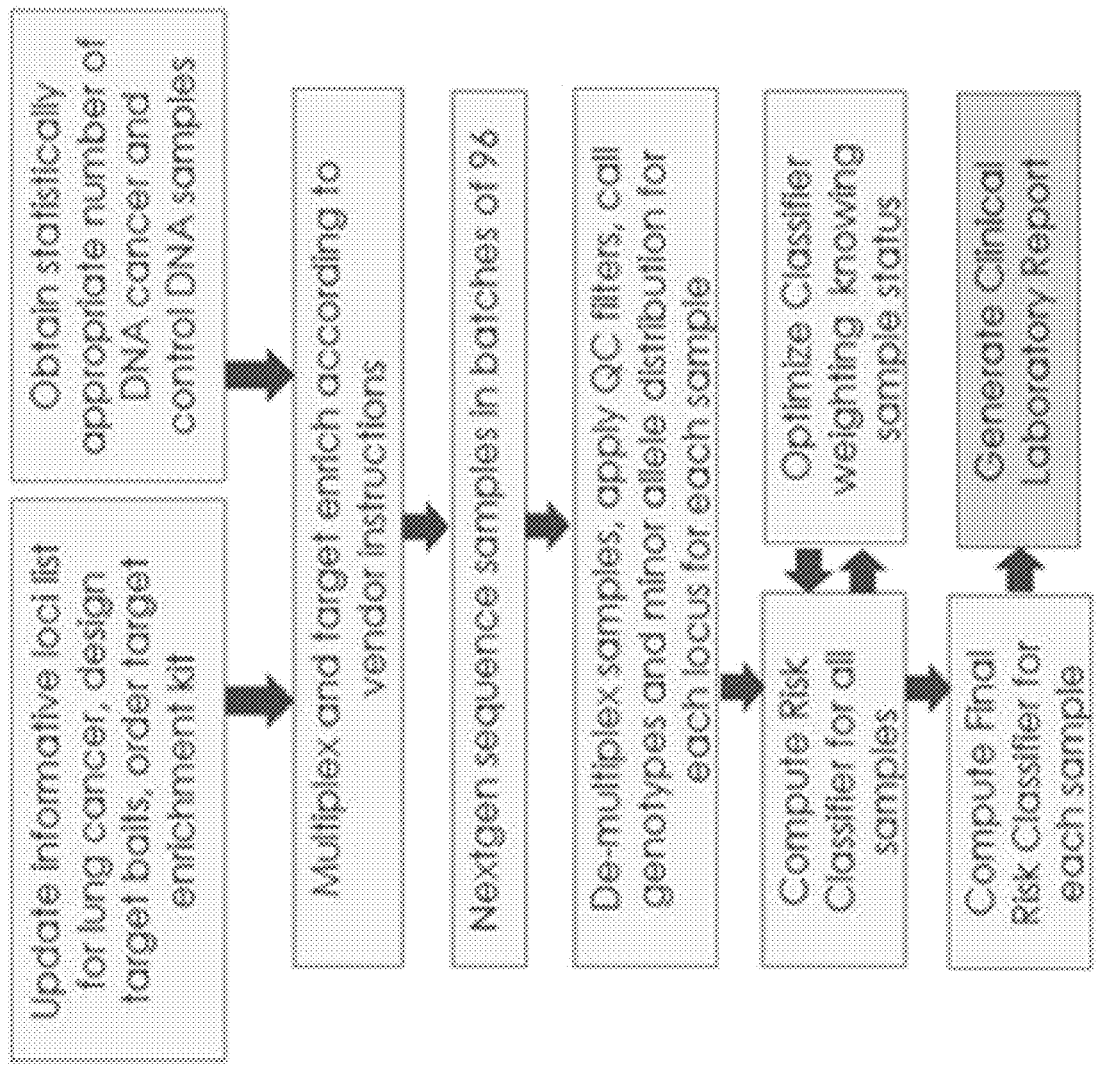
FIG. 3 illustrates an example of a validation process for a lung cancer assay.

The present disclosure provides computer-implemented methods for generating a classifier for a condition from a sample from a subject (see e.g., FIG. 2 and FIG. 3). A list of informative microsatellite loci list can be generated by statistically analyzing samples obtained or derived from a first group of subjects with a condition and/or samples obtained or derived from a second group of subjects without a condition (e.g., a cancer such as lung cancer). The DNA from both groups of samples can be sequenced on a multiplex platform. In some cases, targeted sequencing is performed with an enrichment for certain targets. The sequencing results can then be analyzed for quality and mapped to reveal difference between the cancer sample and the control or reference. This difference can then be analyzed using computer-implemented methods to generate a classifier. The classifier can be further optimized and validated with additional samples obtained or derived from subjects with the condition and/or samples obtained or derived from subjects without the condition. In some aspects, a list of informative genetic markers other than microsatellite can be generated by these methods for developing a classification signature.

Figure 24:
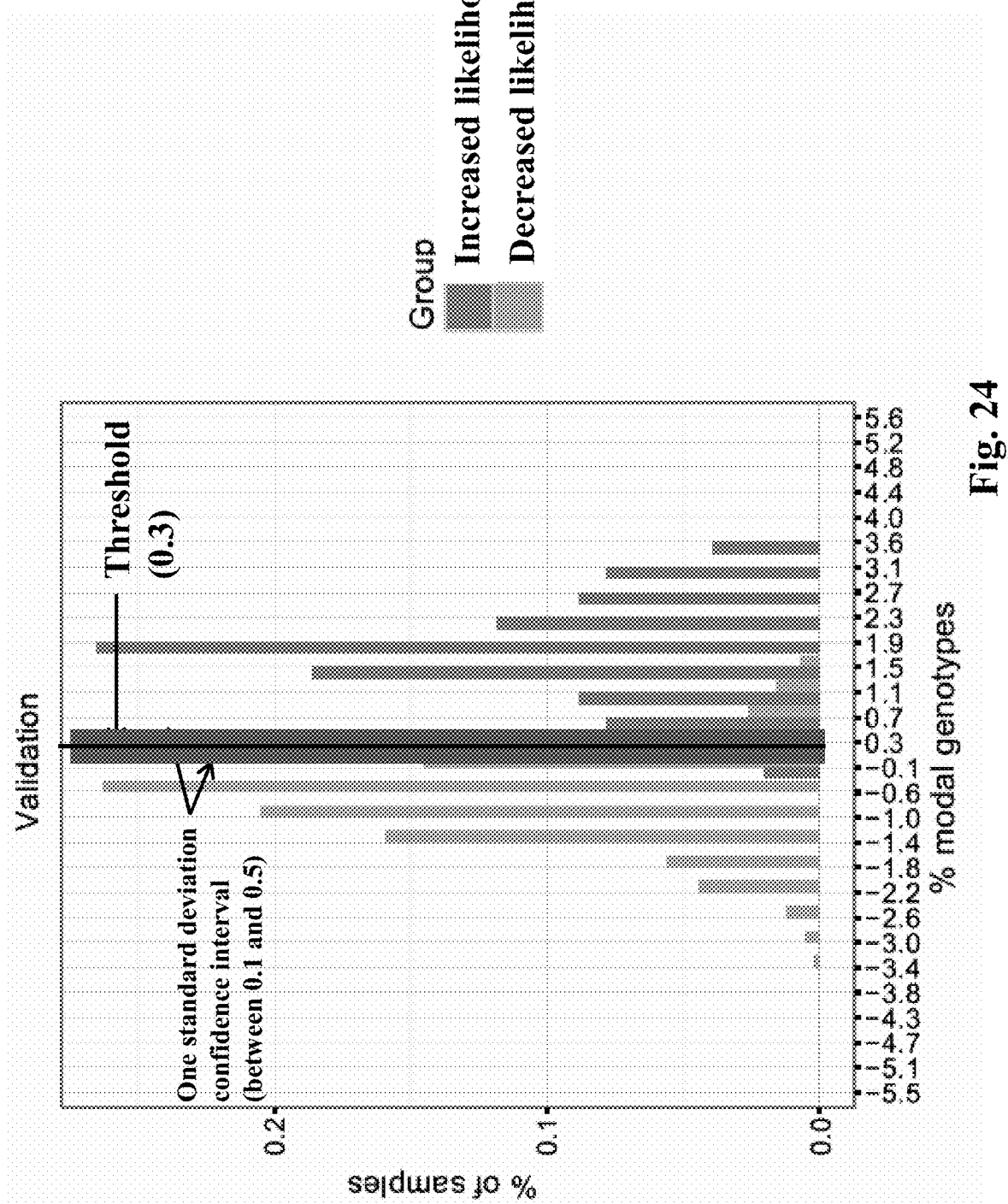
FIG. 24 illustrates a threshold with a 1 standard deviation confidence interval. A classifier that is outside the interval indicates the subject with either the condition (above 0.5) or without the condition (below 0.1). The value of the classifier that is further away from the threshold carries stronger indication.

The condition can be indicative of a presence or absence of a health state in a subject. In some cases, the condition is indicative of an increased or decreased likelihood of development of a health state in a subject. In some instances, the condition can indicative an increased or decreased likelihood of a subject benefitting from a treatment, or an increased or decreased likelihood of a subject having an increased risk for adverse effects as a result of a treatment (the classifier for the condition can serve as a companion diagnostic for a therapeutic agent). In some cases, the condition can be indicative of responsiveness to treatment for a health state in a subject. In some instances, the condition is indicative of the prognosis of a health state in a subject. In some cases, the classifier can be a value, e.g., a number. For example, the value can be indicative of an increased or decreased likelihood (e.g., a probability value between 0 and 1). The value, e.g., number of the classifier can be compared to a threshold value, e.g., number. In some instances, a distance of a classifier value from the threshold can be indicative of increased confidence or probability of having or not having the condition being true. In some cases, a call is made when a classifier value is about 0.5, 1, 1.5, 2, 2.5, 3, or more than 3 standard deviations from a threshold value (FIG. 24).

The computer-implemented methods for generating the classifier can perform processing, combining, statistical evaluation, or further analysis of results, or any combination thereof. The computer-implemented methods can comprise a supervised or unsupervised learning methods, including support vector machine (SVM), neural network, random forests, clustering algorithm (or software module), gradient boosting, linear regression, logistic regression, and/or decision trees. Supervised learning algorithms can be algorithms that rely on the use of a set of labeled, paired training data examples to infer the relationship between an input data and output data. Unsupervised learning algorithms can be algorithms used to draw inferences from training data sets to output data. Unsupervised learning algorithms can comprise cluster analysis, which can be used for exploratory data analysis to find hidden patterns or groupings in process data. An example of an unsupervised learning method is principal component analysis. Principal component analysis can comprise reducing the dimensionality of a set of one or more variables. The dimensionality of a given set of variables can be at least 1, 5, 10, 50, 100, 200, 300, 400, 500, 600, 700, 800, 900, 1000, 1100, 1200 1300, 1400, 1500, 1600, 1700, 1800, or greater than 1800. The dimensionality of a given set of variables can be at most 1800, 1600, 1500, 1400, 1300, 1200, 1100, 1000, 900, 800, 700, 600, 500, 400, 300, 200, 100, 50, 10, or less than 10.

The computer-implemented methods can comprise performing statistical techniques. In some instances, statistical techniques can comprise linear regression, classification, resampling methods, subset selection, shrinkage, dimension reduction, nonlinear models, tree-based methods, support vector machines, unsupervised learning, or any combination thereof.

A linear regression can be a method to predict a target variable by fitting the best linear relationship between a dependent and independent variable. The best fit can correspond to a least-squares approach, such that the sum of all distances between a shape and actual observations at each point is minimized. Linear regression can comprise simple linear regression and multiple linear regression. A simple linear regression can use a single independent variable to predict a dependent variable. A multiple linear regression can use more than one independent variable to predict a dependent variable by fitting a best linear relationship.

A classification can be a data mining technique that assigns categories to a collection of data in order to achieve accurate predictions and analysis. Classification techniques can comprise logistic regression and discriminant analysis. Logistic regression can be used when a dependent variable is dichotomous (binary). Logistic regression can be used to discover and describe a relationship between one dependent binary variable and one or more nominal, ordinal, interval, or ratio-level independent variables. A resampling can be a method comprising drawing repeated samples from original data samples. In some cases, a re-sampling may not involve a utilization of generic distribution tables in order to compute approximate probability values. A resampling can generate a unique sampling distribution on a basis of actual data. In some cases, a resampling can use experimental methods, rather than analytical methods, to generate a unique sampling distribution. Resampling techniques can comprise bootstrapping and cross-validation. Bootstrapping can be performed by sampling with replacement from original data, and take "not chosen" data points as test cases. Cross validation can be performed by split training data into a plurality of parts.

A subset selection can identify a subset of predictors related to a response. A subset selection can comprise best-subset selection, forward stepwise selection, backward stepwise selection, hybrid method, or any combination thereof. In some instances, shrinkage fits a model involving all predictors, but estimated coefficients are shrunken towards zero relative to the least squares estimates. This shrinkage can reduce variance. A shrinkage can comprise ridge regression and a lasso. A dimension reduction can reduce a problem of estimating n+1 coefficients to a simpler problem of m+1 coefficients, where m<n. It can be attained by computing n different linear combinations, or projections, of variables. Then these n projections can then be used as predictors to fit a linear regression model, e.g., by least squares. Dimension reduction can comprise principal component regression and partial least squares. A principal component regression can be used to derive a low dimensional set of features from a large set of variables. A principal component used in a principal component regression can capture the most variance in data using linear combinations of data in subsequently orthogonal directions. The partial least squares can be used as a supervised alternative to principal component regression because partial least squares can make use of a response variable in order to identify new features.

A nonlinear regression can be a form of regression analysis in which observational data are modeled by a function which is a nonlinear combination of model parameters and depends on one or more independent variables. A nonlinear regression can comprise a step function, piecewise function, spline, generalized additive model, or any combination thereof.

Tree-based methods can be used for both regression and classification problems. Regression and classification problems can involve stratifying or segmenting the predictor space into a number of simple regions. Tree-based methods can comprise bagging, boosting, random forest, or any combination thereof. Bagging can decrease a variance of prediction by generating additional data for training from the original dataset using combinations with repetitions to produce multistep of the same carnality/size as original data. Boosting can calculate an output using several different models and then average a result using a weighted average approach. A random forest algorithm can draw random bootstrap samples of a training set. Support vector machines can be used for classification techniques. Support vector machines can comprise finding a hyperplane that best separates two classes of points with the maximum margin. Support vector machines can constrain an optimization problem such that a margin is maximized subject to a constraint that it perfectly classifies data.

Unsupervised methods can be methods to draw inferences from datasets comprising input data without labeled responses. Unsupervised methods can comprise clustering, principal component analysis, k-Mean clustering, hierarchical clustering, or any combination thereof 1. Genetic Algorithm In some aspects, the computer-implemented methods for generating the classifier comprise use of a genetic algorithm. The method can comprise generating an initial population of subsets of microsatellite loci associated or correlated with the condition (informative loci) by identifying the microsatellite loci from the samples with the condition that are different from the microsatellite loci from the samples without the condition. The genetic algorithm can be used to determine a classification signature based on the informative loci. The genetic algorithm can select the subsets of most informative microsatellite loci to include in a final classifier. The genetic algorithm can assign weights to each subset. The weighting can be combined with other weighting schemes, e.g., proportionality to relative risk of each microsatellite loci. Each subset of microsatellites can be iteratively ranked based on association or correlation of the subset with the condition. The subsets of the initial population of microsatellite loci can then be optimized by comparing the initial population with additional samples obtained or derived from subjects with the condition and/or subjects without the condition. In some cases, an initial population of about 100 subsets is used in the optimization. In some cases, an initial population of at least 100, 200, 300, 400, or 500 subsets is used in the optimization. In some instances, the optimization comprises at least one cycle of comparing the about 100 subsets with the additional samples. In some instances, the optimization comprises a plurality of cycles of comparing the about 100 subsets with the additional samples. Each subset can comprise at least 1, 2, 3, 4, 5, 6, 7, 8, 9, 10, 15, 20, 25, 30, 35, 40, 45, 50, 60, 70, 80, 90, or 100 microsatellites.

An iterative ranking can be performed upon completion of each cycle. In some cases, the iterative ranking comprises performing a statistical analysis of the subsets for receiver operating characteristic (ROC) analysis for accuracy, sensitivity, and specificity in determining the presence or absence of the condition in the additional samples. A pre-determined number (e.g., 10) of the worst performing or lowest ranked subsets in indicating the presence or absence of the condition can be identified and discarded. To maintain a constant number of subsets before initiation of each cycle of optimization, new subsets can be added to the population of subsets. In some cases, 1, 2, 3, 4, 5, 6, 7, 8, 9, 10, or more than 10 of the new subsets are generated from randomly splitting and recombining 2 randomly chosen subsets from the previous cycle of optimization. In some instances, 1, 2, 3, 4, 5, 6, 7, 8, 9, 10, or more than 10 of the new subsets are chosen randomly from previous cycle of optimization. In some instances of the 10 new subsets being added, 3 are generated from randomly splitting and recombining 2 randomly chosen subsets from the previous cycle of optimization, and 7 are chosen randomly from subsets of previous cycle of optimization. In some instances of the 10 new subsets being added, 4 are generated from randomly splitting and recombining 2 randomly chosen subsets from the previous cycle of optimization, and 6 are chosen randomly from subsets of previous cycle of optimization. In some instances of the 10 new subsets being added, 5 are generated from randomly splitting and recombining 2 randomly chosen subsets from the previous cycle of optimization, and 5 are chosen randomly from subsets of previous cycle of optimization. In some instances of the 10 new subsets being added, 6 are generated from randomly splitting and recombining 2 randomly chosen subsets from the previous cycle of optimization, and 4 are chosen randomly from subsets of previous cycle of optimization. In some instances of the 10 new subsets being added, 6 are generated from randomly splitting and recombining 2 randomly chosen subsets from the previous cycle of optimization, and 4 are chosen randomly from subsets of previous cycle of optimization. In some instances of the 10 new subsets being added, 7 are generated from randomly splitting and recombining 2 randomly chosen subsets from the previous cycle of optimization, and 3 are chosen randomly from subsets of previous cycle of optimization. Duplicates of new subsets can be included in the cycle of optimization. In some cases, duplicates of new subsets are not included in the cycle of optimization.

In some cases, the number of subsets being discarded at the end of each cycle of optimization is the same number of subsets being added to the subsets prior to each cycle of optimization. In some cases, 5 lowest ranked subsets are being discarded at the end of each cycle of optimization, while 5 new subsets are being added prior to each cycle of optimization. In some cases, 10 lowest ranked subsets are being discarded at the end of each cycle of optimization, while 10 new subsets are being added prior to each cycle of optimization. In some cases, 20 lowest ranked subsets are being discarded at the end of each cycle of optimization, while 20 new subsets are being added prior to each cycle of optimization. In some cases, 50 lowest ranked subsets are being discarded at the end of each cycle of optimization, while 50 new subsets are being added prior to each cycle of optimization.

In some aspects, the computer-implemented methods for generating the classifier comprise determining statistically unweighted subsets of microsatellites. In some aspects, the computer-implemented methods for generating the classifier comprise determining statistically weighted subsets of microsatellites. In some cases, the weight subsets are weighted by relative risk, risk ratio, or odds ratio. The classifier can be unweighted or weighted. In some cases, the classifier generated by the aforementioned computer-implemented methods can be based on genetic markers other than microsatellite. In some cases, the classifier can be based on other genomic information, e.g., single nucleotide polymorphism (SNPs) or genetic aberrations, e.g., copy number aberrations, indels, etc. In some cases, the classifier can be based on the identity of a gene in which a microsatellite is located.

Upon completion of the cycles of optimization, the computer-implemented method can comprise determining the microsatellites associated or correlated with the condition with optimized accuracy, sensitivity, and specificity. In some aspects, the computer-implemented methods can be validated with additional sets of samples comprising samples with the condition, samples without the condition, or a combination thereof (see e.g., FIG. 3). Validation can comprise using at least 10, 20, 30, 50, 100, or 1000 samples from subject with a condition, e.g., cancer (the samples can be a non-tumor (germline) samples or tumor samples) and at least 10, 20, 30, 50, 100 or 1000 samples from subjects without the condition, e.g., cancer, e.g., lung cancer.

The optimized and validated computer-implemented methods can generate a classifier for a condition when analyzing a sample from a subject. The condition can be indicative of a presence or absence of a health state in the subject. In some cases, the condition is indicative of an increased or decreased likelihood of development of a health state in a subject. In some instances, the condition can indicate an increased or decreased likelihood of a subject benefitting from a treatment, or an increased or decreased likelihood of a subject having an increased risk for adverse effects as a result of a treatment. In some cases, the condition can be indicative of responsiveness to a treatment for a health state of a subject. In some instances, the condition is indicative of the prognosis of a health state in a subject.

The condition can indicate a presence or absence of a cancer. In some cases, the condition is indicative of an increased or decreased likelihood of development of the cancer. In some instances, the condition indicates an increased or decreased likelihood of a subject benefitting from a treatment, or increased or decreased likelihood of a subject having an increased risk for adverse effects as a result of a treatment (the classifier can be a companion diagnostic for a cancer treatment). In some cases, the condition can be indicative of responsiveness to treatment for the cancer. The treatment can be surgery, chemotherapy, radiation, targeted treatments with drugs (e.g., afatinib, gefinib, bevacizumab, crizotinib, or ceritinib), or immunotherapy (e.g., treatments with monoclonal antibodies, checkpoint inhibitors, therapeutic vaccines, or adoptive T-cell transfer). In some instances, the condition is indicative of the prognosis of the cancer. In some cases, the cancer is lung cancer, including non-small cell lung cancer (e.g., lung adenocarcinoma (LUAD), lung squamous cell carcinoma (LUSC), and large cell carcinoma), small cell lung cancer (SCLC), or lung carcinoid tumor.

The classifier can include microsatellite loci from any chromosome, e.g., chromosome 1, 2, 3, 4, 5, 6, 7, 8, 9, 10, 11, 12, 13, 14, 15, 16, 17, 18, 19, 20, 21, 22, X, or Y. In some cases, the classifier contains no microsatellite loci from an X chromosome and/or a Y chromosome.

III. Generating a Weighted Classifier for a Condition

The present disclosure provides methods of weighting microsatellite loci that have been identified to associate or correlate with a condition. Also, the present disclosure provides methods of weighting genetic markers other than microsatellite loci that have been identified to associate or correlate with a condition. Weights or weighting can refer to the relative importance or prevalence of each individual microsatellite locus statistically contributing to the association or correlation to the condition. For example, high weights can be assigned to the microsatellite loci that both only appear and appear with higher frequency in the samples obtained from subjects with the condition. In some cases, weights are assigned based on risk ratio, odds ratio, or relative risk. Examples of numeric components that are part of the determination of weights include sensitivity, specificity, negative predictive value, positive predictive values, odds ratio, hazard ratio, or any combination thereof. In some cases, a cutoff (e.g., threshold) is imposed on the numeric components that are used to calculate the weights. Samples with numeric classifiers that fall below the cutoff can be excluded from the weight calculation. The weights can be calculated based on a combination of linear, non-linear, algebraic, trigonometric, statistical learning, Bayesian, regression, or correlative means of calculation. A weighting scheme using values (e.g., relative risks), or a regression approach, associated with a microsatellite or a set of microsatellites can be used to generate a classifier. The weighted classifier can be evaluated to determine whether weighting improves classifier sensitivity or specificity. A regression analysis (e.g., standard regression analysis) can be used to compute optimal weights for each locus in order to maximize the sensitivity and specificity (e.g., a sum of sensitivity and specificity).

In some cases, the weight assigned to each microsatellite is a predetermined value, where the predetermined value dictates the sample size or the strength of association or correlation between the condition and the microsatellite loci. In certain instances, the weight assigned to each microsatellite comprises relative risk, risk ratio, or odds ratio. In some instances, the predetermined value of the weight determines the numerical ranges of sensitivity, specificity, or a combination thereof (e.g., a sum). In some instances, the calculation and assigning of the weight comprises decision-making models implemented by a computer via models, such as support vector machines, decision trees, random forests, neural networks or deep learning neural network (e.g., Artificial Neural Network, Recurrent Neural Network, Convolutional Neural Network, Perception, Feed Forward, Radial Basis Network, Deep Feed Forward, Recurrent Neural Network, Long/Short Term Memory, Gated Recurrent Unit, Auto Encoder (AE), Variation AE, Denoising AE, Sparse AE, Markov Chain, Hopfield Network, Boltzmann Machine, Restricted BM, Deep Belief Network, Deep Convolutional Network, Deconvolutional Network, Deep Convolutional Inverse Graphics Network, Generative Adversarial Network, Liquid State Machine, Extreme Learning Machine, Each State Network, Deep Residual Network, Kohonen Network, Support Vector Machine, and Neural Turing Machine.)

In some instances, the weights assigned to the microsatellite loci are used as part of the calculation for the classifier as described herein. In such instances, microsatellite loci with larger weights can contribute more toward the value of the classifier than microsatellite loci with a smaller weight. In some cases, the calculation of the classifier comprises the use of only the optimal weights. Optimal weights can comprise weights that are at least or greater than predetermined thresholds.

The condition as determined by the weighted classifier can be indicative of a presence or absence of a health state in a subject. In some cases, the condition as determined by the weighted classifier is indicative of an increased or decreased likelihood of development of a health state in a subject. In some instances, the condition as determined by the weighted classifier indicates an increased or decreased likelihood of a subject benefitting from a treatment, or an increased or decreased likelihood of a subject having an increased risk for adverse effects as a result of a treatment. In some instances, the condition as determined by the weighted classifier is indicative of responsiveness to treatment for a health state of a subject. In other instances, the condition as determined by the weighted classifier can be indicative of the prognosis of a health state in a subject. In some cases, the health state is cancer. In some cases, the cancer is lung cancer, e.g., non-small cell lung cancer (e.g., lung adenocarcinoma (LUAD), lung squamous cell carcinoma (LUSC), and large cell carcinoma), small cell lung cancer (NSLC), or lung carcinoid tumor.

A classifier can also be determined based on a minor allele distribution, e.g., of microsatellites. In some cases, the classifier can be determined by calculating a weighted combination of the informative microsatellite loci and the minor allele distribution. Minor allele frequency can be an additional weighted parameter for a classifier. Minor allele frequency can be an indicator of overall genomic stability. A classifier based on minor allele frequency can be statistically evaluated (e.g., by regression analysis) to determine whether addition of the minor allele frequency to the classifier improves the classifier.

IV. Pan-Condition (e.g., Cancer) Risk Assay

Figure 4:
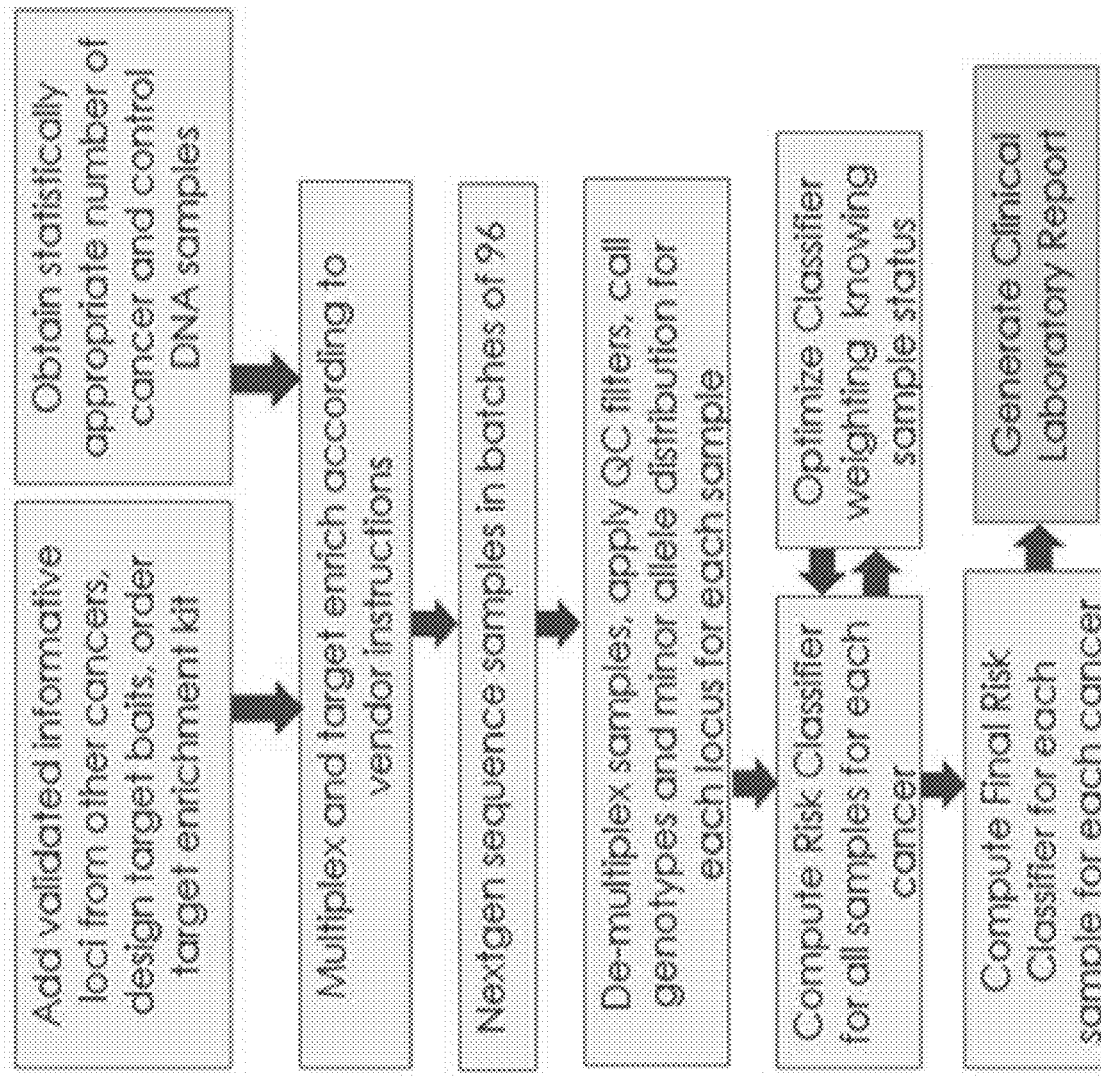
FIG. 4 illustrates an example of validating a pan-cancer assay.

The present disclosure provides computer-implemented methods for generating a pan-condition (e.g., cancer) classifier (see e.g., FIG. 2 and FIG. 4). An informative microsatellite loci list can be generated from statistically analyzing samples of various condition (e.g., cancer) types and healthy reference sequences. The DNA from both groups of samples can be sequenced on a multiplex platform. In some cases, the sequencing is targeted with an additional enrichment, using, e.g., bait sets. The sequencing results are then analyzed for quality and mapped to reveal difference between the condition (e.g., cancer) sample and the reference. This difference can be analyzed to the computer-implemented methods to generate a pan-condition (e.g., cancer) classifier. The pan-condition (e.g., cancer) classifier can be further optimized and validated with additional samples of various types of condition, e.g., cancer.

The pan-condition (e.g., pan-cancer) classifier for a condition or a plurality of conditions can indicate a presence or absence of at least one health state of plurality of health states in a subject, an increased or decreased likelihood of development of at least one health state of plurality of health states in a subject, an increased or decreased likelihood of a subject benefitting from a treatment for at least one health state of the plurality of health states, an increased or decreased likelihood of a subject having an increased risk for adverse effects from a treatment for at least one health state of the plurality of health states, responsiveness of a subject to a treatment for at least one health state of the plurality of health states, or a combination thereof. The plurality of health states can be any combination of health states disclosed herein.

In some cases, the pan-cancer conditions can indicate presence or absence of multiple types of cancer in the subject. In some instances, the pan-cancer conditions can be indicative of an increased or decreased likelihood of development of multiple types of cancers in the subjects, In certain cases, the multiple types of cancers are cancers that frequently arise together in the same subject. In alternative cases, the multiple types of cancers are cancers that arise independently. In some instances, the pan-cancer conditions can indicate that the subject is likely, or is not likely, to benefit from a treatment, or the subject is likely, or not likely, to be at increased risk for adverse effects as a result of a treatment (the pan-cancer classifier can be a companion diagnostic for a therapeutic product). In some instances, the pan-cancer conditions can indicate responsiveness to treatment for the cancer in a subject. In other instances, the pan-cancer conditions can be indicative of the prognosis of the cancer in a subject. A subject as described herein can be either symptomatic or asymptomatic for cancer. In some cases, additional examinations (e.g., physical exams, analysis of circulating or cell-free cancer biomarkers, imaging (e.g., computerized tomography (CT), bone scan, magnetic resonance imaging (MRI), positron emission tomography (PET), ultrasound, and X-ray), biopsy, genetic screening, gene or protein expression levels, etc) can be used in based on a pan-cancer classifier for the subject.

The computer-implemented methods for generating the pan-condition (e.g., pan-cancer) classifier can comprise performing processing, combining, statistical evaluation, or further analysis of results, or any combination thereof. In some aspects, the computer-implemented methods for generating the pan-condition (e.g., cancer) classifier comprise first generating a population of subsets of microsatellite loci associated or correlated with plurality types of condition (e.g., cancer) by identifying the microsatellite loci from the samples obtained or derived from subjects with the plurality types of condition (e.g., cancer) that are different from the microsatellite loci from the samples obtained or derived from subjects without the plurality types of condition (e.g., cancer). The sequences of the microsatellite can be first obtained by any sequencing methods.

The microsatellite loci that are associated or correlated to the plurality types of condition (e.g., cancer) can be identified with one or more statistical tests such as t-test, Z-test, ANOVA, regression analysis, Mann-Whitney-Wilcoxon, Chi-squared test, correlation, Fisher's exact test, Bonferroni correction, and Benjamini-Hochberg test.

Statistical tests can yield a receiver operating characteristic (ROC) curve, where the area under the ROC curve is referred to as the area under the curve (AUC). AUC can determine the accuracy of identifying microsatellite loci associated or correlated to the plurality of types of condition (e.g., cancer). A greater AUC can be indicative of higher accuracy of the association or correlation. ROC curves can determine the rates of sensitivity (e.g., true positives) and specificity (e.g., true negatives) for the association or correlation of the microsatellite loci to the plurality of types of condition (e.g., cancer). The statistically significant association or correlation of the microsatellite loci to the plurality types of condition (e.g., cancer) can have a statistical accuracy of at least about 70%, 80%, 85%, 90%, 91%, 92%, 93%, 94%, 95%, 96%, 97%, 98%, or 99%. In some cases, the statistically significant association or correlation of the microsatellite loci to the plurality types of condition (e.g., cancer) has a statistical specificity of at least 0.70, 0.80, 0.85, 0.90, 0.91, 0.92, 0.93, 0.94, 0.95, 0.96, 0.97, 0.98, or 0.99 and a statistical sensitivity of at least 0.70, 0.80, 0.85, 0.90, 0.91, 0.92, 0.93, 0.94, 0.95, 0.96, 0.97, 0.98, or 0.99.

In some instances, identifying the microsatellite loci associated or correlated to the plurality types of condition (e.g., cancer) comprises identifying a first set of microsatellite loci from a database comprising nucleic acid sequences of the plurality types of condition (e.g., cancer) and a second set of microsatellite loci from a reference database (e.g., hg19). In some cases, some of the microsatellites are identified to be associated or correlated with multiple types of condition (e.g., cancer). In some cases, some of the microsatellites are identified to be associated or correlated with one type of condition (e.g., cancer).

The plurality of types of cancer can comprise solid or hematologic malignant types of cancer. In some cases, the plurality of types of cancer can be metastatic, relapsed, or refractory. The plurality of types of cancer that are associated or correlated with the identified microsatellite loci can include any number (e.g., about 4 to about 10, about 10 to about 15, about 15 to about 20, or about 4, about 10, about 15, about 20, about 25, about 30, or about 50) of the cancers disclosed herein.

The pan-cancer assay can assay or can test for at least 1, 2, 3, 4, 5, 6, 7, 8, 9, 10, 11, 12, 13, 14, 15, or 16 of the following cancers: breast cancer, ovarian cancer, prostate cancer, lung cancer, Glioblastoma Multiforme, Uterine Corpus Endometrial Carcinoma, Colon Adenocarcinoma, Bladder cancer, Urothelial Carcinoma, Head and Neck Squamous Cell Carcinoma, Cervical Squamous Cell Carcinoma and Endocervical Adenocarcinoma, Stomach Adenocarcinoma, Thyroid Carcinoma, Brain Lower Grade Glioma, Kidney Renal Papillary Cell Carcinoma, and Liver Hepatocellular Carcinoma.

In some cases, the plurality of types of cancer associated or correlated to the difference of the sets of microsatellite loci comprises lung cancer. A lung cancer that can be associated or correlated with the different of the sets of the microsatellite loci includes non-small cell lung cancer (e.g., lung adenocarcinoma (LUAD), lung squamous cell carcinoma (LUSC), and large cell carcinoma), small cell lung cancer (SCLC), and lung carcinoid tumor.

The population of subsets comprising microsatellite loci associated or correlated with plurality of types of condition (e.g., cancer) can comprise at least 1, 2, 3, 4, 5, 6, 7, 8, 9, 10, 15, 20, 25, 30, 35, 40, 45, 50, 60, 70, 80, 90, or 100 microsatellite loci per subset. In some aspects, the population of subsets is iteratively ranked based on association or correlation of the subsets with the plurality types of condition (e.g., cancer).

The subsets of the population of microsatellite loci can then be optimized by comparing the population of subsets with additional samples obtained or derived from subjects with the plurality of types of conditions (e.g., cancer) and/or subjects without the plurality types of condition (e.g., cancer). In some cases, the population of about 100 subsets is used in the optimization. In some cases, the population of at least 100, 200, 300, 400, 500, 1000, 2000, 3000, or 5000 subsets is used in the optimization. In some instances, the optimization comprises at least one cycle of comparing the about 100 identified subsets with the additional samples. In some instances, the optimization comprises a plurality of cycles of comparing the about 100 identified subsets with the additional samples.

An iterative ranking can be performed upon completion of each cycle. In some cases, the iterative ranking comprises performing statistical analysis of the subsets for receiver operating characteristic (ROC) analysis for accuracy, sensitivity, and specificity in determining the presence or absence of the plurality of types of condition (e.g., cancer) in the additional samples. One or more of the worst performing or lowest ranked subsets in indicating the presence or absence of the plurality types of condition (e.g., cancer) can be identified and discarded. To maintain a constant number of subsets before initiation of each cycle of optimization, new subsets may be added to the population of subsets. In some cases, the new subsets are generated from randomly splitting and recombining 2 randomly chosen subsets from the previous cycle of optimization. In some instances, the new subsets are chosen randomly from previous cycle of optimization. In some cases, the number of subsets being discarded at the end of each cycle of optimization is the same number of subsets being added to the subsets prior to each cycle of optimization.

The computer-implemented methods for generating the pan-condition (e.g., pan-cancer) classifier can comprise determining statistically unweighted subsets of microsatellite loci. In some aspects, the computer-implemented methods for generating the pan-condition (e.g., pan-cancer) classifier comprise determining statistically weighted subsets of microsatellite loci. The pan-condition (e.g., pan-cancer) classifier can be unweighted or weighted.

After completion of the cycles of optimization, the computer-implemented methods of generating the pan-condition (e.g., pan-cancer) classifier comprise the microsatellite loci associated or correlated with the condition with optimized accuracy, sensitivity, and specificity. In some aspects, the computer-implemented methods can be validated with additional sets of samples comprising samples obtained or derived from subjects with the plurality of types of condition (e.g., cancer), samples obtained or derived from subjects without the plurality of types of condition (e.g., cancer), or a combination thereof. The optimized and validated computer-implemented methods can generate the pan-condition (e.g., pan-cancer classifier) when analyzing a sample from a subject. The pan-condition (e.g., pan-cancer) can be indicative of a presence or absence of a type of health state (e.g., cancer) in the subject. In certain cases, the pan-condition (e.g., pan-cancer) is indicative of an increased or decreased likelihood of development of a type of health state (e.g., cancer) in the subject. In some cases, the pan-condition (e.g., pan-cancer) can indicate an increase or decrease likelihood of a subject benefitting from a treatment, or an increased or decreased likelihood of a subject having an increased risk for adverse effects as a result of a treatment (the pan-condition, e.g., pan-cancer, classifier can be a companion diagnostic for a therapeutic product). In some instances, the pan-condition (e.g., pan-caner) is indicative of responsiveness to treatment for a type of health state (e.g., cancer) of the subject. In other instances, the pan-condition (e.g., pan-cancer) is indicative of the prognosis of a type of health state (e.g., cancer) in the subject.

A classifier (e.g., set of microsatellites) can be developed for each condition (e.g., cancer) in the pan-condition (e.g., pan-cancer) assay. In some cases, individual microsatellite loci can be pan-condition (e.g., pan-cancer) microsatellite loci.

V. Evaluating Samples from Subjects

Figure 5:
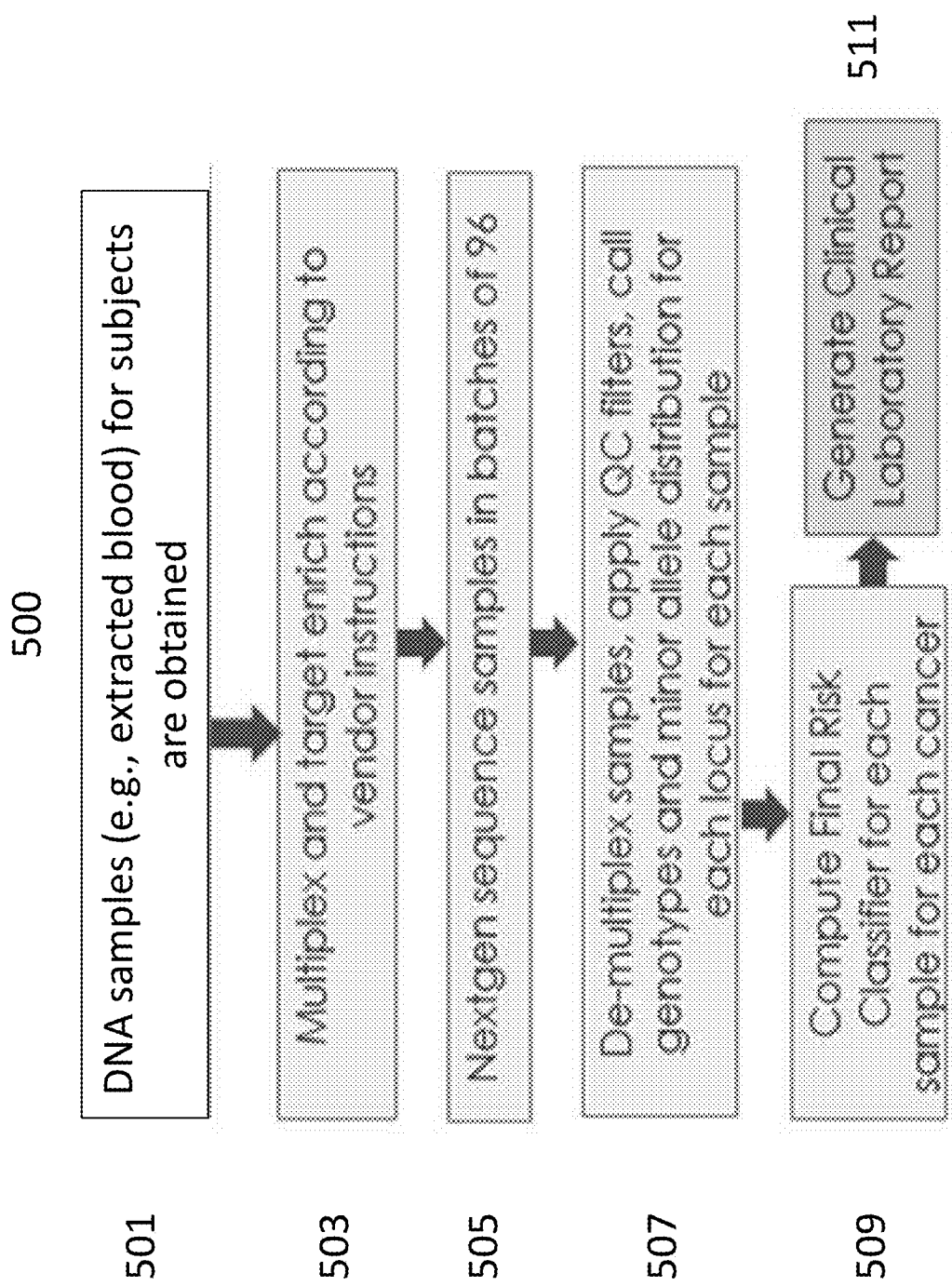
FIG. 5 illustrates an example of a workflow for analysis of patient samples.

Classifiers generated as described herein can be used to analyze subject (e.g., patient) samples. Samples from subjects can be analyzed, e.g., in a Clinical Laboratory Improvements Amendments (CLIA) certified laboratory. In some cases, kits are prepared and samples from subjects are analyzed outside a CLIA laboratory. FIG. 5 illustrates an example of a workflow (500) for a subject (e.g., patient) sample analysis pipeline in, e.g., a CLIA certified lab; the workflow can be used for processing samples for a multiplexed pan-cancer assay. Samples, e.g., samples from blood, urine, cerebrospinal fluid, seminal fluid, saliva, sputum, stool, lymph fluid, tissue (e,g, thyroid, skin, heart, lung, kidney, breast, pancreas, liver, muscle, smooth muscle, bladder, gall bladder, colon, intestine, brain, esophagus, or prostate), or any combination thereof, are obtained from a plurality of subjects (501). Nucleic acid molecules, e.g., genomic DNA, are extracted from the samples. Targets, e.g., microsatellite targets, are enriched by multiplexing (e.g., using baits, e.g., hybridization probes); the enriched targets can be barcoded and amplified (503). A next-generation sequencing assay is performed on the target enriched samples, e.g., in batches of about 4, 8, 12, 24, 96, 128, 384, or 1536 (505). Sequencing data can be de-multiplexed (e.g., using unique sequence tags (e.g., barcodes) added to each individual sample), quality control filters can be applied to raw sequence reads (e.g., Phred quality of greater than Q30), and genotypes are determined (e.g., reads for each locus are aligned to a reference sequence using flanking sequence then the 2 primary alleles (genotype) are computed) and minor allele distributions (e.g., number of minor alleles or fraction of minor alleles relative to major genotypes) are determined for each microsatellite locus of each sample (507) (a minor allele can be supported by at least 1, at least 2, at least 3, or more than 3 sequence reads). A risk classifier (e.g., based on at least 5, 10, 25, 50 or 100 microsatellite loci) for each sample for each cancer is calculated (509) (e.g., genotypes can be determined to be modal or non-modal with respect to most prominent genotypes in healthy populations (e.g., GRCh38) genotype and summed across all loci, and a sample can be classified as at risk or not at risk for a condition depending on where they lie with respect to a cutoff of the fraction of loci that have the cancer or normal genotypes). The risk can be on a quantitative scale or indicated by a categorical assessment. A clinical laboratory report is generated (511) comprising the risk classifiers and provided to a healthcare provider, subject, or insurance provider.

Figure 17:
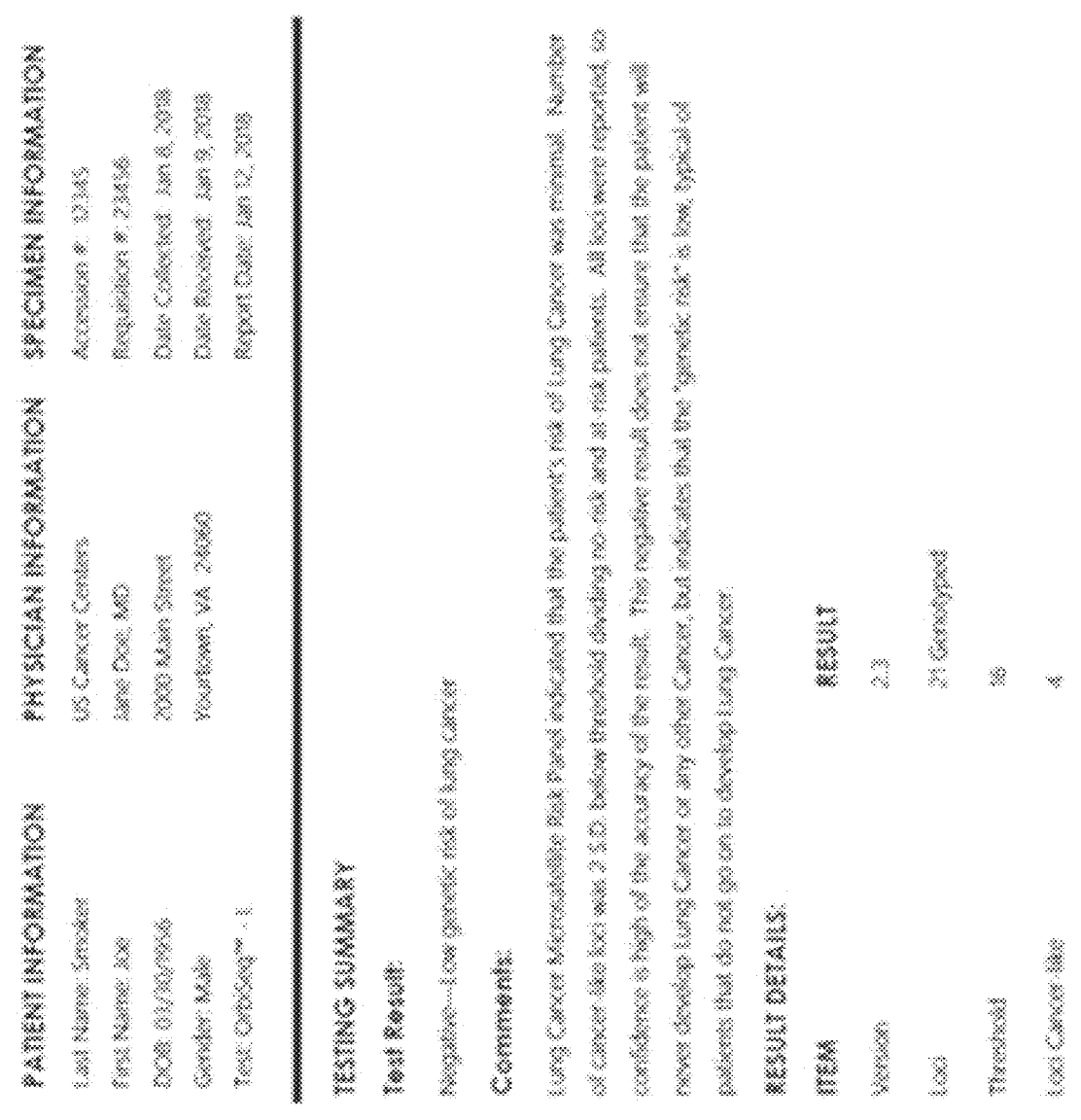

FIG. 17 illustrates an example of a clinical laboratory report. The clinical laboratory report can comprise patient information, specimen information, a testing summary, a test result, comments, and result details. The result details can include the number of microsatellite loci genotyped, one or more risk classifiers for condition, one or more thresholds, and a relative risk (e.g., low risk, high risk, "at risk," "not at risk") for having or acquiring a condition, e.g., lung cancer.

The report can include the number of loci in the sample of the subject having non-modal (predominately cancer) genotypes. The sensitivity and specificity for detection of health state presence determined to be at high risk can be greater than 90%, and absence in those control sample germlines determined to be at "low risk" for lung cancer. The precision of the assay can be greater than 99% as measured by highly conserved loci in reference controls.

In some instances, the condition can be validated or further examined by additional examinations, e.g., physical exams, analysis of circulating or cell-free cancer biomarkers, imaging (e.g., computerized tomography, bone scan, magnetic resonance imaging, positron emission tomography, ultrasound, and X-ray), biopsy, genetic screening, gene expression, or protein expression, etc.

VI. Minor Alleles in Microsatellites

The present disclosure provides computer-implemented methods of determining a genomic age and rate of genomic aging for a subject. Genomic age can be given in a number that is calibrated to years. For example, if a genomic age is approximately equal to a numerical age of a subject, an overall genomic stability can be normal for the genomic age. In some instances, the genomic age can be younger, the same, or older than an actual age for the subject. An older genomic age than an actual age of a subject, or high rate of genomic aging, can suggest genomic instability and susceptibility to develop health states (e.g., diseases) associated with aging, e.g., cancer, cardiovascular diseases, neurological disease, etc. Genomic age and rate of genomic aging can vary among the samples obtained from different tissues (e.g., skin or blood) of the same subject. In some cases, genomic age and rate of genomic aging can indicate one's life style (e.g., nutrition, physical or mental stress) or medical condition. Changes in lifestyle (e.g., stop smoking, alter diet, and exercising) can be recommended to a subject based on the subject's genomic age.

The computer-implemented methods of determining the genomic age and rate of genomic aging can comprise determining a minor allele characteristic in a first sample from the subject and comparing the minor allele characteristic of the first sample to the minor allele characteristic of a reference to yield a first difference of minor allele characteristic. The reference can include distributions of minor allele content across a large population to determine the average genomic age as a function of numerical age, ethnicity, gender, etc. The first difference of the minor allele characteristic between the first sample and the reference can be determined, by the computer-implemented methods, to be the genomic age of the subject. In some aspects, a second sample from the subject is compared to the reference at a time point that is after the comparison of the first sample to the reference to yield a second difference of minor allele characteristic. The changes between the first and second differences can be determined by computer-implemented methods to be a rate of genomic aging of the subject. In some cases, additional rate of genomic aging can be determined by obtaining and comparing later minor allele characteristics to earlier minor allele characteristics.

Minor allele characteristic as described herein can be the number of minor allele at at least one locus. In some aspects, the minor allele characteristic comprises a percentage of SNPs, percentage of expansions, percentage of contractions, ratio of expansions and contractions to SNPs, percentage of heterozygotic loci, percentage of homozygotic loci, and percentage of loci with minor alleles. In some cases, the minor allele characteristic comprises a combination of SNPs and indel variations, microsatellite variations, synonymous SNPs, non-synonymous SNPs, stopgain SNPs, stoploss SNPs, splicing variant (e.g., 2-bp within a splicing junction), frameshift indel, and non-frameshift indel at at least one locus. In some cases, the minor allele characteristic is determined across multiple time points in the same subject.

Minor allele characteristic as determined from the sample from the subject can require at least 1 sequence read from any method of sequencing. In some cases, the minor allele characteristic can be identified in at least 1, 2, 3, 4, 5, 6, 7, 8, 9, 10, 20, 30, 50, or 100 sequence reads from any method of next-generation sequencing. Minor allele characteristic as determined from the sample from the subject can require at least 1, at least 2, at least 3, or more than 3 sequence reads from any method of sequencing.

In some instances, the minor allele characteristic as determined from the sequence of the sample from the subject is compared to a reference sequence. The comparison can yield a difference of minor allele characteristic from the reference sequence comprising different numbers of combination of SNPs and indel variations, microsatellite variations, synonymous SNPs, non-synonymous SNPs, stopgain SNPs, stoploss SNPs, splicing variant (e.g., 2-bp within a splicing junction), frameshift indel, and non-frameshift indel at at least one locus. The difference of minor allele characteristic between the sample and the reference can be determined by the computer-implemented methods to yield a genomic age.

In some cases, a first sequence of a first sample from a subject is compared to a reference sequence to yield a first minor allele characteristic and a first genomic age. In some instances, a second sequence of a second sample from the same subject is compared to the same reference sequence to yield second minor allele characteristic and a second genomic age. Comparison between the first minor allele characteristic with the second minor allele characteristic can determine a rate of genomic aging. In certain instances, multiple minor allele characteristics can be obtained from samples from the same subject at later time points for comparisons to yield multiple rates of genomic aging at different ages of the subject.

The present disclosure provides computer-implemented methods of determining a genomic age for a subject by determining a microsatellite minor allele characteristic in a first sample from a subject. The microsatellite minor allele characteristic can be minor allele comprising microsatellite with different percentage of SNPs, percentage of expansions, percentage of contractions, ratio of expansions and contractions to SNPs, percentage of heterozygotic loci, or percentage of homozygotic loci when compared to a reference sequence. In some cases, the microsatellite minor allele characteristic comprise minor allele comprising microsatellite with different combination of SNPs and indel variations, microsatellite variations, synonymous SNPs, non-synonymous SNPs, stopgain SNPs, stoploss SNPs, splicing variant (e.g., 2-bp within a splicing junction), frameshift indel, or non-frameshift indel at at least one locus when compared to a reference sequence. In some cases, the microsatellite minor allele characteristic is determined across multiple time points in the same subject.

VI. Computer System, Processor, and Memory

The present disclosure provides a computer system configured to implement the methods described in this disclosure. In some instances, disclosed herein is a system comprising: a computer processing device, optionally connected to a computer network; and a software module executed by the computer processing device. In some instances, the system comprises a central processing unit (CPU), memory (e.g., random access memory, flash memory), electronic storage unit, computer program, communication interface to communicate with one or more other systems, and any combination thereof. In some instances, the system is coupled to a computer network, for example, the Internet, intranet, and/or extranet that is in communication with the Internet, a telecommunication, or data network. In some aspects, the system comprises a storage unit to store data and information regarding any aspect of the methods described in this disclosure. Various aspects of the system are a product or article or manufacture.

One feature of a computer program includes a sequence of instructions, executable in the digital processing device's CPU, written to perform a specified task. In some aspects, computer-readable instructions are implemented as program modules, such as functions, features, Application Programming Interfaces (APIs), data structures, and the like, that perform particular tasks or implement particular abstract data types. In various embodiments, a computer program can be written in various versions of various languages.

The functionality of the computer-readable instructions are combined or distributed as desired in various environments. In some instances, a computer program comprises one sequence of instructions or a plurality of sequences of instructions. A computer program can be provided from one location. A computer program can be provided from a plurality of locations. In some aspects, a computer program includes one or more software modules. In some aspects, a computer program includes, in part or in whole, one or more web applications, one or more mobile applications, one or more standalone applications, one or more web browser plug-ins, extensions, add-ins, or add-ons, or combinations thereof.

Computer Systems

Figure 18:
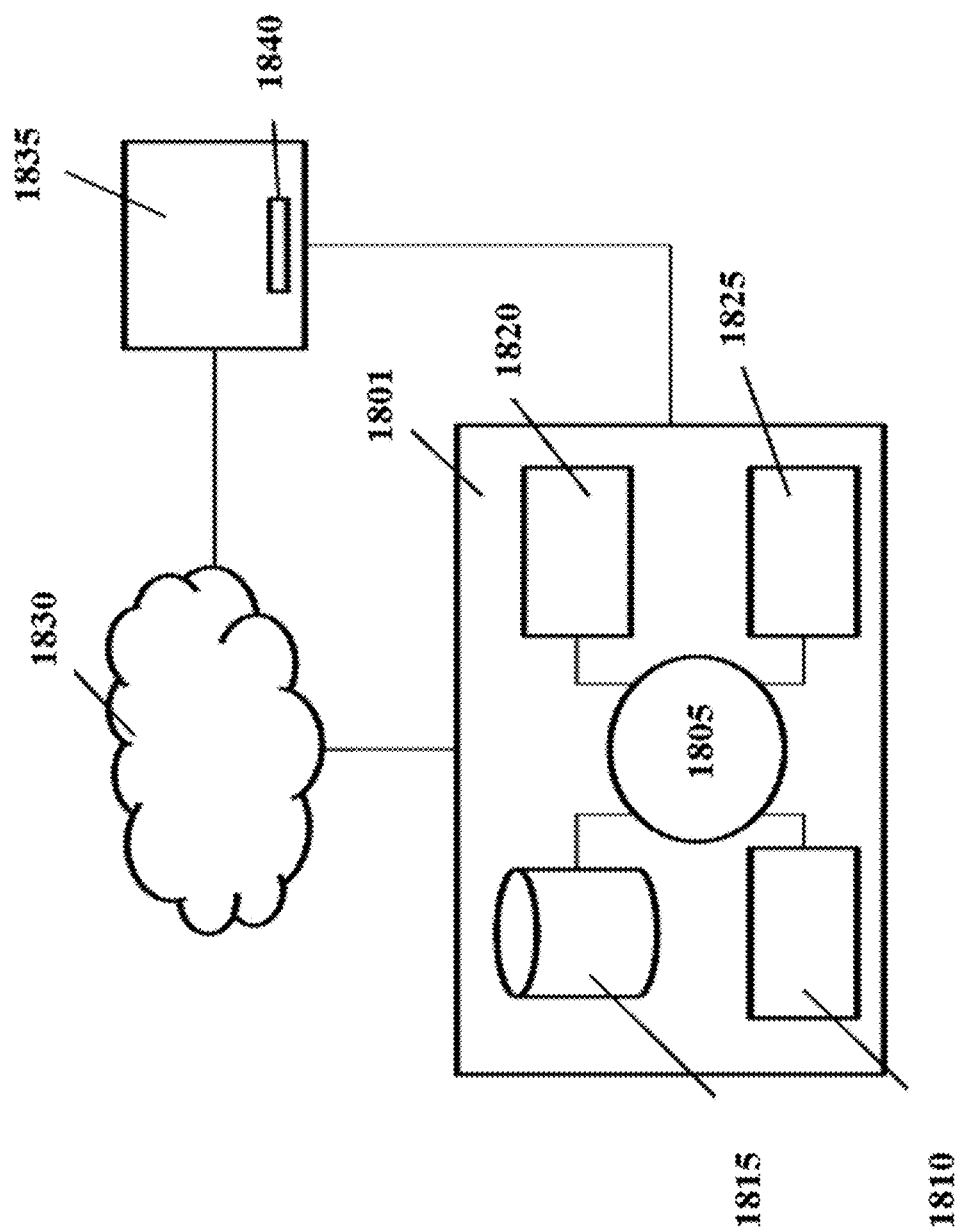
FIG. 18 illustrates a computer system that is programmed or otherwise configured to implement methods provided herein.

The present disclosure provides computer systems that are programmed to implement methods of the disclosure. FIG. 18 shows a computer system (1801) that can be programmed or otherwise configured to execute methods described herein. The computer system (1801) can regulate various aspects of the present disclosure, including inputting nucleic acid position information, transferring imputed information into datasets, and generating a trained algorithm with the datasets. The computer system (1801) can be a user electronic device or a remote computer system. The electronic device can be a mobile electronic device.

The computer system (1801) includes a central processing unit (CPU, also "processor" and "computer processor" herein) (1805), which can be a single core or multi core processor, either through sequential processing or parallel processing. The computer system (1801) also includes a memory unit or device (1810) (e.g., random-access memory, read-only memory, flash memory), a storage unit (1815) (e.g., hard disk), a communication interface (1820) (e.g., network adapter) for communicating with one or more other systems, and peripheral devices (1825), either external or internal or both, such as a printer, monitor, USB drive and/or CD-ROM drive. The memory (1810), storage unit (1815), interface (1820) and peripheral devices (1825) are in communication with the CPU (1805) through a communication bus (solid lines), such as a motherboard. The storage unit (1815) can be a data storage unit (or data repository) for storing data. The computer system (1801) can be operatively coupled to a computer network ("network") (1830) with the aid of the communication interface (1820). The network (1830) can be the Internet, an internet and/or extranet, or an intranet and/or extranet that is in communication with the Internet. The network (1830) in some cases is a telecommunication and/or data network. The network (1830) can include one or more computer servers, which can enable a peer-to-peer network that supports distributed computing. The network (1830), in some cases with the aid of the computer system (1801), can implement a client-server structure, which can enable devices coupled to the computer system (1801) to behave as a client or a server.

The CPU (1805) can execute a sequence of machine-readable instructions, which can be incorporated in a program or software. The instructions can be stored in memory (1810). The instructions can be directed to the CPU (1805), which can subsequently program or otherwise configure the CPU (1805) to implement methods of the present disclosure. Examples of operations performed by the CPU (1805) can include fetch, decode, execute, and writeback.

The CPU (1805) can be part of a circuit, such as an integrated circuit. One or more other components of the system (1801) can be included in the circuit. In some embodiments, the circuit is an application specific integrated circuit (ASIC).

The storage unit (1815) can store files, such as drivers, libraries and saved programs. The storage unit (1815) can store user data, e.g., user preferences and user programs. The computer system (1801) in some cases can include one or more additional data storage units that are external to the computer system (1801), such as located on a remote server that is in communication with the computer system (1801) through an intranet or the Internet.

The computer system (1801) can communicate with one or more remote computer systems through the network (1830). For instance, the computer system (1801) can communicate with a remote computer system or user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system (1801) via the network (1830).

Methods as described herein can be implemented by way of machine (e.g., computer processor) executable code stored on an electronic storage location of the computer system (1801), for example, in memory (1810) or a data storage unit (1815). The machine-executable or machine readable code can be provided in the form of software. During use, the code can be executed by the processor (1805). In some cases, the code can be retrieved from the storage unit (1815) and stored in memory (1810) for ready access by the processor (1805). In some situations, the storage unit (1815) can be precluded, and machine-executable instructions are stored in memory (1810).

The code can be pre-compiled and configured for use with a machine having a processor adapted to execute the code, or it can be compiled during runtime. The code can be supplied in a programming language that can be selected to enable the code to execute in a pre-compiled or as compiled fashion.

Aspects of the systems and methods provided herein, such as the computer system (1801), can be incorporated in programming. Various aspects of the technology can be thought of as "products" or "articles of manufacture" typically in the form of machine (or processor) executable code and/or associated data that is carried on or embodied in a type of machine readable medium. Machine-executable code can be stored on a storage unit, such as a hard disk, or in memory (e.g., read-only memory, random-access memory, flash memory). "Storage" type media can include any or all of the tangible memory of the computers, processors or the like, or associated modules thereof, including various semiconductor memories, tape drives, disk drives and the like, which can provide non-transitory storage at any time for the software programming. All or portions of the software can at times be communicated through the Internet or various other telecommunication networks. Such communications, for example, can enable loading of the software from one computer or processor into another, for example, from a management server or host computer into the computer platform of an application server. Thus, another type of media that can bear the software elements includes optical, electrical and electromagnetic waves, such as used across physical interfaces between local devices, through wired and optical landline networks and over various air-links. The physical elements that carry such waves, such as wired or wireless links, optical links or the like, also can be considered as media bearing the software. As used herein, unless restricted to non-transitory, tangible "storage" media, terms such as computer or machine "readable medium" refer to any medium that participates in providing instructions to a processor for execution.

A. Electronic Device

In some aspects, the platforms, media, methods, and applications described herein include an electronic device, a processor, or use of the same (also referred to as a digital processing device). In further aspects, the electronic device includes one or more hardware central processing units (CPU) that carry out the device's functions. In still further aspects, the electronic device further comprises an operating system configured to perform executable instructions. In some aspects, the electronic device is optionally connected a computer network. In further aspects, the electronic device is optionally connected to the Internet such that it accesses the World Wide Web. In still further aspects, the electronic device is optionally connected to a cloud computing infrastructure. In some aspects, the electronic device is optionally connected to an intranet. In some aspects, the electronic device is optionally connected to a data storage device. In accordance with the description herein, suitable electronic devices include, by way of non-limiting examples, server computers, desktop computers, laptop computers, notebook computers, sub-notebook computers, netbook computers, net pad computers, set-top computers, handheld computers, Internet appliances, mobile smartphones, tablet computers, personal digital assistants, video game consoles, and vehicles. In various embodiments, many smartphones are suitable for use in the system described herein. In various embodiments, select televisions, video players, and digital music players with optional computer network connectivity are suitable for use in the system described herein. Suitable tablet computers include those with booklet, slate, and convertible configurations.

In some aspects, the electronic device includes an operating system configured to perform executable instructions. The operating system is, for example, software, including programs and data, which manages the device's hardware and provides services for execution of applications. In various embodiments, suitable server operating systems include, by way of non-limiting examples, FreeBSD, OpenBSD, NetBSD®, Linux, Ubuntu Linux, Apple® Mac OS X Server °, Oracle® Solaris®, Windows Server®, and Novell® NetWare®. In various embodiments, suitable personal computer operating systems include, by way of non-limiting examples, Microsoft® Windows®, Apple® Mac OS X®, UNIX®, and UNIX-like operating systems such as GNU/Linux®. In some aspects, the operating system is provided by cloud computing. In various embodiments, suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some aspects, the device includes a storage and/or memory device. The storage and/or memory device is one or more physical apparatuses used to store data or programs on a temporary or permanent basis. In some aspects, the device is volatile memory and requires power to maintain stored information. In some aspects, the device is non-volatile memory and retains stored information when the electronic device is not powered. In further aspects, the non-volatile memory comprises flash memory. In some aspects, the non-volatile memory comprises dynamic random-access memory (DRAM). In some aspects, the non-volatile memory comprises ferroelectric random-access memory (FRAM). In some aspects, the non-volatile memory comprises phase-change random access memory (PRAM). In some aspects, the non-volatile memory comprises magnetoresistive random-access memory (MRAM). In some aspects, the device is a storage device including, by way of non-limiting examples, CD-ROMs, DVDs, flash memory devices, magnetic disk drives, magnetic tapes drives, optical disk drives, and cloud computing-based storage. In further aspects, the storage and/or memory device is a combination of devices such as those disclosed herein.

In some aspects, the electronic device includes a display to send visual information to a subject. In some aspects, the display is a cathode ray tube (CRT). In some aspects, the display is a liquid crystal display (LCD). In further aspects, the display is a thin film transistor liquid crystal display (TFT-LCD). In some aspects, the display is an organic light emitting diode (OLED) display. In various further aspects, on OLED display is a passive-matrix OLED (PMOLED) or active-matrix OLED (AMOLED) display. In some aspects, the display is a plasma display. In some aspects, the display is E-paper or E ink. In some aspects, the display is a video projector. In still further aspects, the display is a combination of devices such as those disclosed herein.

In some aspects, the electronic device includes an input device to receive information from a subject. In some aspects, the input device is a keyboard. In some aspects, the input device is a pointing device including, by way of non-limiting examples, a mouse, trackball, trackpad, joystick, game controller, or stylus. In some aspects, the input device is a touch screen or a multi-touch screen. In some aspects, the input device is a microphone to capture voice or other sound input. In some aspects, the input device is a video camera or other sensor to capture motion or visual input. In further aspects, the input device is a Kinect, Leap Motion, or the like. In still further aspects, the input device is a combination of devices such as those disclosed herein.

B. Non-Transitory Computer-Readable Storage Medium

In some aspects, the platforms, media, methods and applications described herein include one or more non-transitory computer-readable storage media encoded with a program including instructions executable by the operating system of an optionally networked digital processing device. In further aspects, a computer-readable storage medium is a tangible component of an electronic device. In still further aspects, a computer-readable storage medium is optionally removable from an electronic device. In some aspects, a computer-readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

C. Computer Program

In some aspects, the platforms, media, methods, and applications described herein include at least one computer program, or use of the same. A computer program includes a sequence of instructions, executable in the electronic device's CPU, written to perform a specified task. Computer-readable instructions can be implemented as program modules, such as functions, objects, Application Programming Interfaces (APIs), data structures, and the like, that perform particular tasks or implement particular abstract data types. In various embodiments, a computer program can be written in various versions of various languages.

The functionality of the computer-readable instructions can be combined or distributed as desired in various environments. In some aspects, a computer program comprises one sequence of instructions. In some aspects, a computer program comprises a plurality of sequences of instructions. In some aspects, a computer program is provided from one location. In some aspects, a computer program is provided from a plurality of locations. In various aspects, a computer program includes one or more software modules. In various aspects, a computer program includes, in part or in whole, one or more web applications, one or more mobile applications, one or more standalone applications, one or more web browser plug-ins, extensions, add-ins, or add-ons, or combinations thereof.

D. Web Application

In some aspects, a computer program includes a web application. In various embodiments, a web application, in various aspects, utilizes one or more software frameworks and one or more database systems. In some aspects, a web application is created upon a software framework such as Microsoft® .NET or Ruby on Rails (RoR). In some aspects, a web application utilizes one or more database systems including, by way of non-limiting examples, relational, non-relational, object oriented, associative, and XML database systems. In further aspects, suitable relational database systems include, by way of non-limiting examples, Microsoft® SQL Server, mySQL™, and Oracle®. In various embodiments, a web application, in various aspects, is written in one or more versions of one or more languages. A web application can be written in one or more markup languages, presentation definition languages, client-side scripting languages, server-side coding languages, database query languages, or combinations thereof. In some aspects, a web application is written to some extent in a markup language such as Hypertext Markup Language (HTML), Extensible Hypertext Markup Language (XHTML), or eXtensible Markup Language (XML). In some aspects, a web application is written to some extent in a presentation definition language such as Cascading Style Sheets (CSS). In some aspects, a web application is written to some extent in a client-side scripting language such as Asynchronous Javascript and XML (AJAX), Flash® Actionscript, Javascript, or Silverlight®. In some aspects, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some aspects, a web application is written to some extent in a database query language such as Structured Query Language (SQL). In some aspects, a web application integrates enterprise server products such as IBM® Lotus Domino®. In some aspects, a web application includes a media player element. In various further aspects, a media player element utilizes one or more of many suitable multimedia technologies including, by way of non-limiting examples, Adobe® Flash®, HTML 5, Apple® QuickTime®, Microsoft® Silverlight®, Java™, and Unity®.

E. Mobile Application

In some aspects, a computer program includes a mobile application provided to a mobile electronic device. In some aspects, the mobile application is provided to a mobile electronic device at the time it is manufactured. In some aspects, the mobile application is provided to a mobile electronic device via the computer network described herein.

In various embodiments, a mobile application is created by various techniques using hardware, languages, and development environments. In various embodiments, mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

In various embodiments, several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

F. Standalone Application

In some aspects, a computer program includes a standalone application, which is a program that is run as an independent computer process, not an add-on to an existing process, e.g., not a plug-in. In various embodiments, standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some aspects, a computer program includes one or more executable compiled applications.

G. Software Modules

In some aspects, the platforms, media, methods, and applications described herein include software, server, and/or database modules, or use of the same. In various embodiments, software modules are created by various techniques using machines, software, and languages. The software modules disclosed herein can be implemented in a multitude of ways. In various aspects, a software module comprises a file, a section of code, a programming object, a programming structure, or combinations thereof. In further various aspects, a software module comprises a plurality of files, a plurality of sections of code, a plurality of programming objects, a plurality of programming structures, or combinations thereof. In various aspects, the one or more software modules comprise, by way of non-limiting examples, a web application, a mobile application, and a standalone application. In some aspects, software modules are in one computer program or application. In some aspects, software modules are in more than one computer program or application. In some aspects, software modules are hosted on one machine. In some aspects, software modules are hosted on more than one machine. In further aspects, software modules are hosted on cloud computing platforms. In some aspects, software modules are hosted on one or more machines in one location. In some aspects, software modules are hosted on one or more machines in more than one location.

H. Databases

In some aspects, the platforms, systems, media, and methods disclosed herein include one or more databases, or use of the same. In various embodiments, many databases are suitable for storage and retrieval of barcode, route, parcel, subject, or network information. In various aspects, suitable databases include, by way of non-limiting examples, relational databases, non-relational databases, object-oriented databases, object databases, entity-relationship model databases, associative databases, and XML databases. In some aspects, a database is internet-based. In further aspects, a database is web-based. In still further aspects, a database is cloud computing-based. In some aspects, a database is based on one or more local computer storage devices.

I. Data transmission

The subject matter described herein, including methods and systems provided herein, can be configured to be performed in one or more facilities at one or more locations. Facility locations are not limited by country and include any country or territory. In some instances, one or more steps are performed in a different country than another step of the method. In some instances, one or more steps for obtaining a sample are performed in a different country than one or more steps for detecting the presence or absence of a condition from a sample. In some aspects, one or more method steps involving a computer system are performed in a different country than another step of the methods provided herein. In some aspects, data processing and analyses are performed in a different country or location than one or more steps of the methods described herein. In some aspects, one or more articles, products, or data are transferred from one or more of the facilities to one or more different facilities for analysis or further analysis. An article includes, but is not limited to, one or more components obtained from a subject, e.g., processed cellular material. Processed cellular material includes, but is not limited to, cDNA reverse transcribed from RNA, amplified RNA, amplified cDNA, sequenced DNA, isolated and/or purified RNA, isolated and/or purified DNA, and isolated and/or purified polypeptide. Data includes, but is not limited to, information regarding the stratification of a subject, and any data produced by the methods disclosed herein. In some aspects of the methods and systems described herein, the analysis is performed and a subsequent data transmission step will convey or transmit the results of the analysis.

J. Web Browser Plug-In

In some aspects, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enables customizing the functionality of a software application. For example, plug-ins are commonly used in web browsers to play video, generate interactivity, scan for viruses, and display particular file types. In various embodiments, several web browser plug-ins can be used, including, Adobe® Flash® Player, Microsoft® Silverlight®, and Apple® QuickTime®. In some aspects, the toolbar comprises one or more web browser extensions, add-ins, or add-ons. In some aspects, the toolbar comprises one or more explorer bars, tool bands, or desk bands.

In various embodiments, several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected electronic devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some aspects, the web browser is a mobile web browser. Mobile web browsers (also called microbrowsers, mini-browsers, and wireless browsers) are designed for use on mobile electronic devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

K. Business Methods Utilizing a Computer

The methods described herein can utilize one or more computers. The computer can be used for managing customer and sample information such as sample or customer tracking, database management, analyzing molecular profiling data, analyzing cytological data, storing data, billing, marketing, reporting results, storing results, or a combination thereof. The computer can include a monitor or other graphical interface for displaying data, results, billing information, marketing information (e.g., demographics), customer information, or sample information. The computer can also include means for data or information input. The computer can include a processing unit and fixed or removable media or a combination thereof. The computer can be accessed by a user in physical proximity to the computer, for example via a keyboard and/or mouse, or by a user that does not necessarily have access to the physical computer through a communication medium such as a modem, an internet connection, a telephone connection, or a wired or wireless communication signal carrier wave. In some cases, the computer can be connected to a server or other communication device for relaying information from a user to the computer or from the computer to a user. In some cases, the user can store data or information obtained from the computer through a communication medium on media, such as removable media. It is envisioned that data relating to the methods can be transmitted over such networks or connections for reception and/or review by a party. The receiving party can be but is not limited to an individual, a health care provider or a health care manager. In one instance, a computer-readable medium includes a medium suitable for transmission of a result of an analysis of a biological sample. The medium can include a result of a subject, wherein such a result is derived using the methods described herein.

The entity obtaining the sample information can enter it into a database for the purpose of one or more of the following: inventory tracking, assay result tracking, order tracking, customer management, customer service, billing, and sales. Sample information can include, but is not limited to: customer name, unique customer identification, customer associated medical professional, indicated assay or assays, assay results, adequacy status, indicated adequacy tests, medical history of the individual, preliminary diagnosis, suspected diagnosis, sample history, insurance provider, medical provider, third party testing center or any information suitable for storage in a database. Sample history can include but is not limited to: age of the sample, type of sample, method of acquisition, method of storage, or method of transport.

The database can be accessible by a customer, medical professional, insurance provider, or other third party. Database access can take the form of electronic communication such as a computer or telephone. The database can be accessed through an intermediary such as a customer service representative, business representative, consultant, independent testing center, or medical professional. The availability or degree of database access or sample information, such as assay results, can change upon payment of a fee for products and services rendered or to be rendered. The degree of database access or sample information can be restricted to comply with generally accepted or legal requirements for patient or customer confidentiality.

EXAMPLES

The examples provided below are for illustrative purposes only and are not intended to limit the scope of the claims provided herein.

Example 1: Germline Microsatellite Genotypes Differentiate Children with Medulloblastoma (MB)

Introduction

Medulloblastoma (MB) is a common malignant childhood brain tumor. MB can be primarily caused by inherited or spontaneous mutations as the children with MB have yet to undergo a lifetime of environmental exposures and stresses. Extensive genomic characterization has divided MB tumors into at least 4 consensus molecular subgroups: WNT, SHH, Group3, and Group 4, each having distinct transcriptional profiles, copy number alterations, somatic mutations and clinical outcomes. Pediatric brain cancers in general and MB specifically, have 5-10 fold fewer mutations than typically observed in adult solid tumors. Notably uncommon are the most significant tumor initiating genetic mutations such as p53, PTEN, RB, and EGFR. In addition, the incidence of known heritable tumor predisposing mutations can be relatively low. The few known genetic aberrations, such as mutations of PTCH, SMO, and CTNNB1, and amplification of MYC and MYCN, can be individually insufficient to efficiently cause MB in animal models and can require a potentiating background, usually p53 inactivation, which can be found in less than 5% of human tumors. Numerous Genome-wide Association Studies (GWAS) in MB can have focused on single nucleotide variants, while ignoring non-coding regions and repetitive DNA. However, linkage can be shown between germline microsatellite (MS) insertion and deletions (indels) and a number of neurological disorders such as Huntington's disease and Friedreich ataxia; the former caused by a microsatellite variant in the coding sequence and the latter in a non-coding intronic sequence. Furthermore, microsatellite variations can contribute to the genetic background of several cancers. In addition, many cancer-associated genes contain MS loci (e.g., PTEN and NF1), and in some cases, somatic MS indels have been causally implicated in cancer. Based on these findings, a permissive constitutional genetic environment can be created by the cooperation of DNA microsatellite repeat elements affecting the transcriptional and translational landscape of an individual, making them susceptible to tumor formation through modulation of foundational cellular processes.

MSs can include a 1-6 base pair unit repeated in tandem to form an array. Over 600,000 unique MSs exist in the human genome, and they can be embedded in gene introns, exons, and regulatory regions. The length of microsatellite loci can frequently change due to strand slip replication and heterozygote instability, varying between alleles and between individuals. These changes can influence gene expression by inducing Z-DNA and H-DNA folding; altering nucleosome positioning; and changing the spacing of DNA binding sites. Non-coding variations can alter DNA secondary structure and protein/RNA binding of the genes proximate to their locations, resulting in changes in transcriptional and translational activity as well as alternative splicing. For these reasons MSs have been called the "tuning knobs" of gene expression. Within exons, microsatellite loci containing repeated elements of 3 or 6 base pairs can cause amino acid gain or loss by staying in frame with codon triplets; other non-modulo-3 lengths can cause frameshift mutations. Genes harboring MSs can contribute disproportionately to nervous system disorders. This particular vulnerability to the expansion of tandem repeats, especially the CAG motif, can indicate an importance in neurodevelopment. In fact, repetitive elements can play a role in neurological diseases; poly-glutamate repeats in particular can play a role in Huntington's disease, spinocerebellar ataxia, and spinobulbar muscular atrophy. Similarly, bioinformatics studies indicate that many genes hosting tandem repeats can have a neural function.

The development of microsatellite genotyping algorithms and advances in genome sequencing have allowed the identification of germline microsatellite genotypes that can distinguish healthy from affected individuals with different types of cancers (breast, colon, glioma, etc.) Described in the instant example is a set of microsatellite genotypes able to differentiate children with MB from healthy individuals based upon their germline DNA.

Methods

Patent Samples

Germline DNA WES and WGS from medulloblastoma (MB) patients were downloaded from the following datasets: phs000504, phs000409, EGAD00001000122, EGAD00001000275, EGAD00001000816, and Waszak, S. M, et. Al (Spectrum and prevalence of genetic predisposition in medulloblastoma: a retrospective genetic study and prospective validation in a clinical trial cohort. The Lancet Oncology, Volume 19, Issue 6, 785-798, which is incorporated by reference herein in its entirety). Additionally, WES from 6 MB patients' blood DNA were newly generated using the TruSeq exome target enrichment kit and Illumina Sequencer HiSeq 2500. Germline DNA WES and WGS from healthy controls were downloaded from 1000 Genomes. Germline DNA WES from one hundred healthy children was provided by Hopp Children's Cancer Center at the NCT Heidelberg, Heidelberg, Germany.

Sequence Mapping and Coverage

WES and WGS reads were mapped to the human GRCh38/hg38 reference genome using Bowtie2. Overall, the coverage for the 120 MB germline samples was 31× (31.0±18.2). Coverage for the samples in the control group was 13×(13.4±7.8).

Microsatellite List Generation

A list of microsatellites in version GRCh38/hg38 of the human reference genome was generated with a custom Perl script 'searchTandemRepeats.pl' using default parameters. This script can be used in microsatellite studies and is freely available online. Briefly, the 'searchTandemRepeats.pl' script first searched for pure repetitive stretches: no impurities allowed. Imperfect repeats and compound repeats were then handled using a "mergeGap" parameter with a default value of 10 base pairs. Essentially, impurities that interrupted stretches of pure repeat sequence were tolerated unless they exceeded 10 base pairs. Likewise, repeats closer than 10 base pairs were considered compound. The result was that repeats in the CAGm database were highly pure and components of compound repeats were also highly pure. The initial list generated with this script included 1,671,121 microsatellites. To mitigate the likelihood of improper read mapping among microsatellites, all subsets of microsatellites possessing the same repeat motif between five base pair long 3' and 5' flanking regions were removed. For example, the microsatellites 'GCTGC(A)$_{34}$CTTAG' and 'GCTGC(A)$_{15}$CTTAG' were preemptively removed from the initial list of microsatellites. Microsatellites can be embedded in larger repetitive motifs. The filtered list included 625,195 unique microsatellites in the human genome.

Microsatellite Genotyping

The program Repeatseq was used to determine the genotype of microsatellites in next-generation sequencing reads. Repeatseq uses Bayesian model selection guided by an empirically derived error model. The error model incorporated sequence and read properties: unit, length, and base quality. Repeatseq operated on three input files: a reference genome, a file containing reads aligned to the human reference genome (.bam file), and a list of known microsatellites (in accordance with methods and systems disclosed herein). The output was a variant call format (.vcf) file listing the genotype for each microsatellite locus consisting of the two alleles with most supporting reads. An advantage of Repeatseq over other microsatellite genotyping programs was that it realigned each read to the reference genome prior to array length detection. Repeatseq can be used in studies of microsatellites and is freely available.

The capabilities of Repeatseq were extended for detection of somatic microsatellite variability: e.g., minor alleles. Minor alleles can be distinct from the primary alleles of the genotype; they can be somatically acquired in normal tissues as one ages. Minor alleles were used as an indication of microsatellite mutability. Briefly, detection of minor alleles was enabled with two steps that build on the Repeatseq output. First, output of the realigned reads was enabled in the call to Repeatseq. Second, realigned reads are cleared of all primary alleles of the genotype. Among the remaining reads, those array lengths supported by at least three reads were counted as minor alleles. However, when comparing minor alleles in different samples an alternative approach was used. Specifically, array lengths supported by at least 20% of the total read depth are counted as minor alleles.

Statistics

A power calculation was conducted based on previous observations of microsatellite genotype distributions for other cancers and controls to select the size of the training sets, while assuring there were sufficient samples in a test set for validation. A conservative Type I error probability associated with the test of this null hypothesis of 0.01 was chosen as part of the validation. The response within each subject group can be shown to be normally distributed with a standard deviation of 1. For a true difference in the experimental and control means of 2, the null hypothesis that the population means of the experimental and control groups were equal with probability (power) greater than 0.99 for a study with 120 experimental subjects and 426 control subjects was rejected. Thus, the training set was predicted to be adequately powered with the number of samples available.

Figure 9:
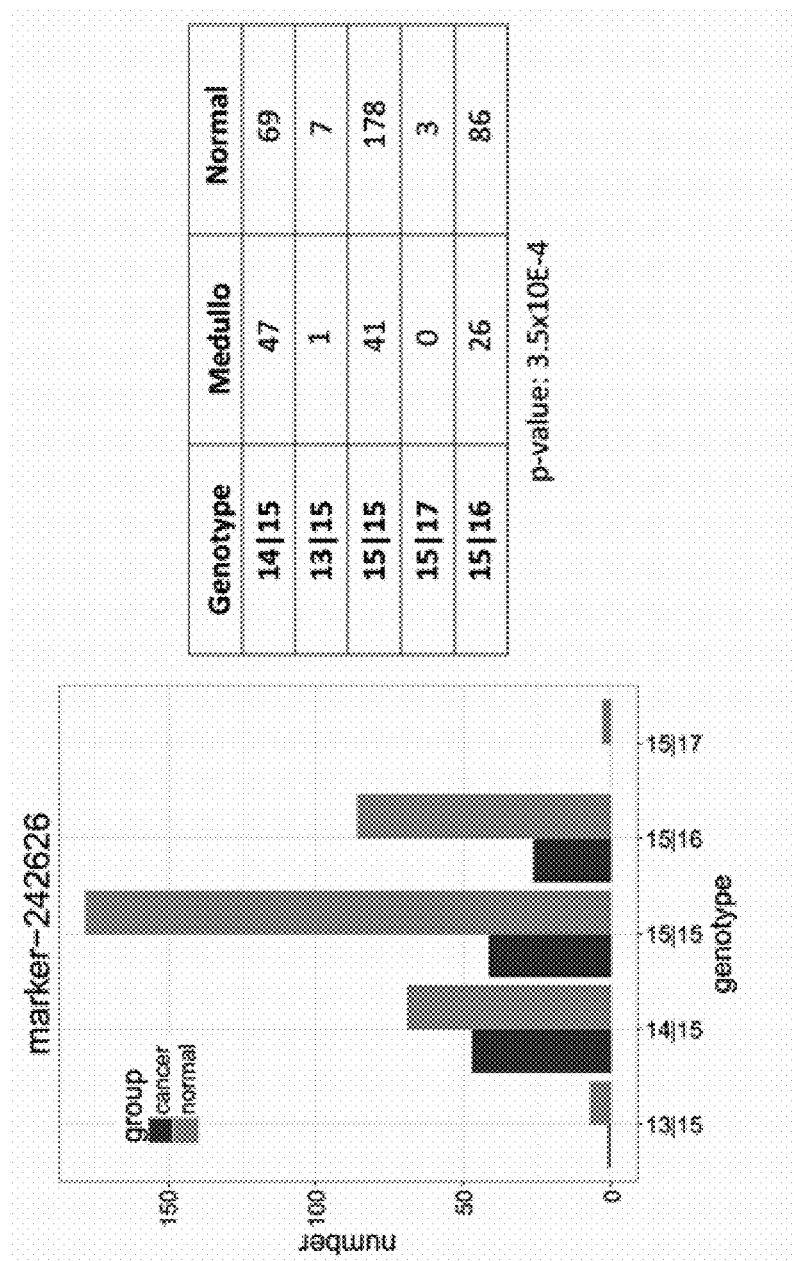
FIG. 9 illustrates an example of the genotype distribution and contingency table used in a study described herein. Distribution of genotypes for microsatellite marker 242626 on chromosome 1, base pair 153645035. The p-value for this example is $3.5e^{-4}$. The right table is the contingency table for the same microsatellite marker.

For each microsatellite, the distribution of genotypes differed in the germline DNA from two groups of samples in the training dataset: 120 MB and 425 healthy controls. In each case, statistical differences were quantified using a generalized Fisher's exact test. Briefly, for each microsatellite, a contingency table was populated with genotype counts for the two groups: MB and normal (FIG. 9). Then, p-values for each contingency table were calculated using the fisher test function in R. The Benjamini-Hochberg multiple testing correction (n=43,457 tested microsatellites) was applied to control the false discovery rate.

Microsatellite Filtering to Control for Age, Ethnicity and Sequencing Protocol

This study was designed to identify germline microsatellite variations specific to MB; specifically, statistically significant microsatellites were identified in 120 MB samples and 425 healthy controls. However, these samples were not matched for age or sequencing protocol; further, they were only partially matched for ethnicity. Thus, this approach can have a risk of identifying microsatellites with age, sequencing, and ethnic bias rather than disease status alone. To mitigate this risk, microsatellites were identified with potential bias—for age, sequencing, or ethnicity—and excluded them from subsequent analysis.

Figure 10:
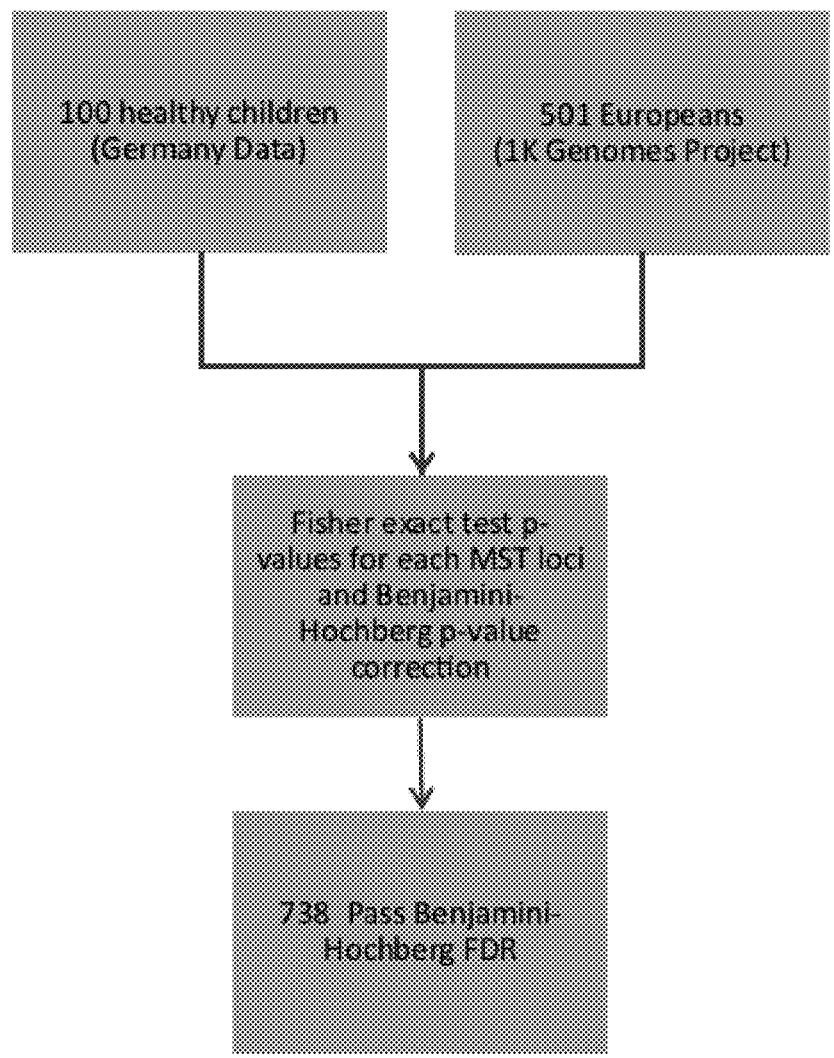
FIG. 10 illustrates a summary of a workflow used to identify MSs sensitive to age.

Controlling for age: To identify microsatellites whose genotypes vary non-randomly with age, 100 healthy European children and 501 European adults from the 1,000 genome project were compared. Fisher's exact test identified 738 (out of 29,061) statistically significant microsatellites: Benjamin-Hochberg correction (p-value<0.05) (FIG. 10).

Figure 11:
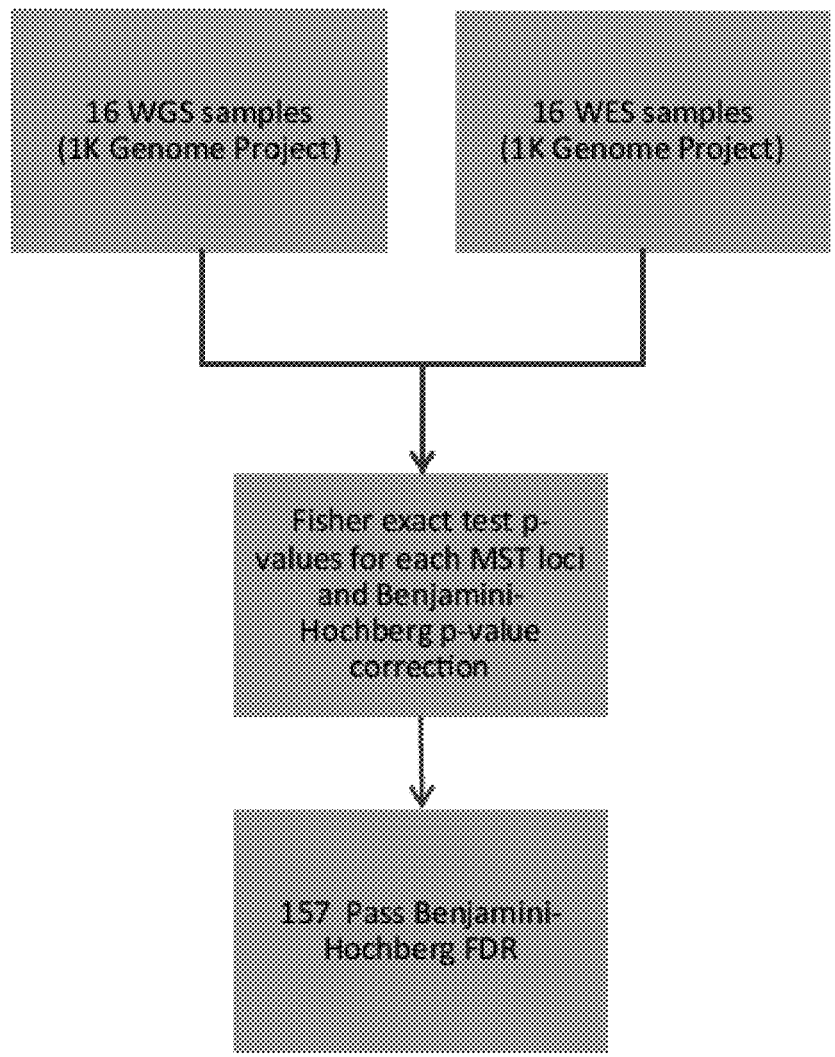
FIG. 11 illustrates a summary of a workflow used to identify MSs sensitive to sequencing technology.

Controlling for sequencing protocol: To identify microsatellites that vary based upon DNA sequencing protocol (WGS vs. WES), genotypes from paired WGS and WES experiments in 16 individuals in the 1,000 genomes project were compared. The distribution of genotypes for 37,511 microsatellites were tested for statistical difference (Fisher's exact test); 157 were found to differ using Benjamin-Hochberg false discovery correction (p-value<0.05) (FIG. 11). This was likely due to the fact that microsatellites were prone to read mapping errors, particularly when they harbor large insertions or deletions. Thus, the 157 identified microsatellites may be particularly prone to mapping errors or reside in highly variable regions of the genome; they were excluded from subsequent analysis. In addition, 37,775 identified microsatellite calls were absent in 134 WGS samples. Consequently, these 37,775 were unusable for microsatellite based assays of risk, diagnosis, or prognosis; they were excluded from subsequent analysis (FIG. 11).

Figure 12:
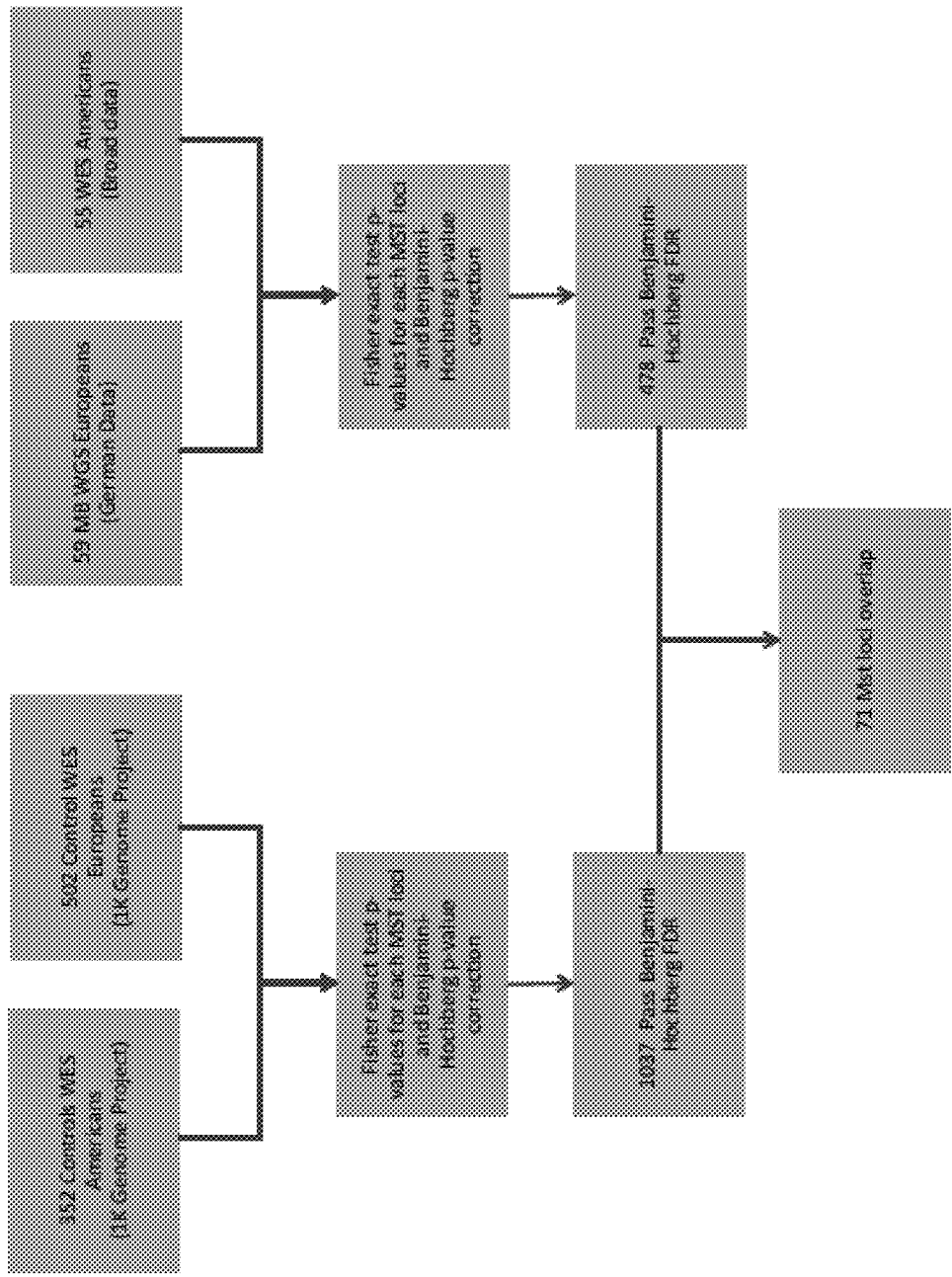
FIG. 12 illustrates a summary of a workflow used to identify MSs sensitive to ethnicity.

Controlling for ethnicity: To identify DNA microsatellites that vary according to ethnicity, the distribution of genotypes in 352 American samples and 502 European samples, all coming from the 1,000 genome project, were compared and analyzed. In total, 184,981 statistical tests were performed, with 1,037 microsatellites revealed to be significantly different using Benjamini-Hochberg false discovery correction (p-value<0.05). Further, the distribution of microsatellite genotypes in a group of 59 predominately European MB samples and 55 predominately American MB samples were examined. Here, 13,899 tests were made with 478 microsatellites found to differ after Benjamini-Hochberg false discovery correction (p-value<0.05). 71 microsatellites were identified that were present in both lists, which were excluded from further analysis (FIG. 12).

The unique microsatellites from the 3 steps above number 38,653; all were removed from further analysis.

Metric to Score Samples and ROC Analysis

Figure 13:
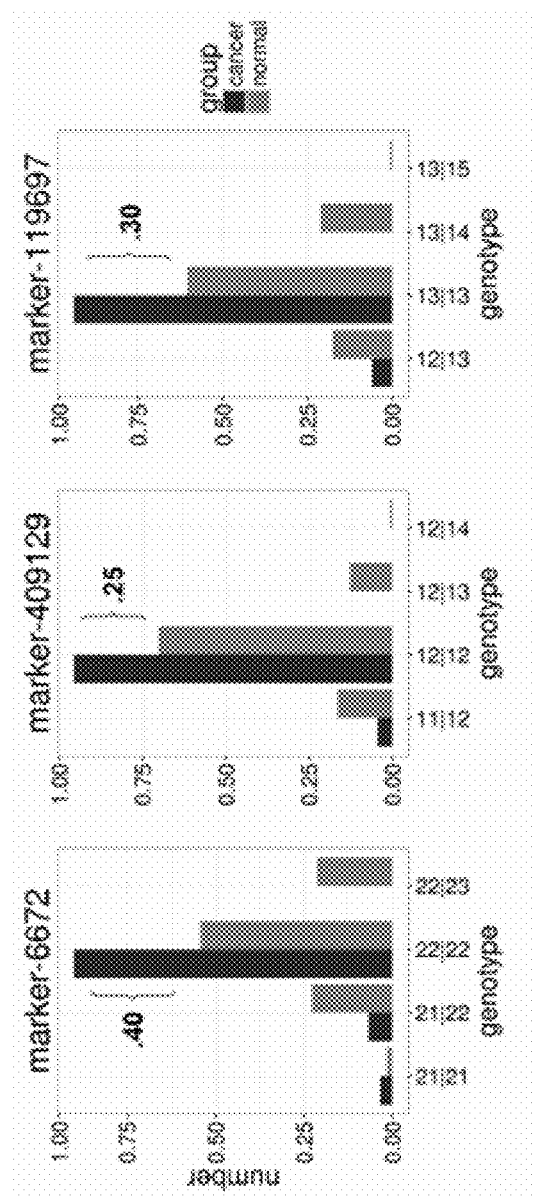
FIG. 13 illustrates an example of a metric used to assign scores to samples. Consider a hypothetical sample with genotypes 22122, 12112, and 13113 respectively for the markers above. To apply a metric to this sample, sum the differences in frequency of each genotype in the MB and healthy groups: the result is a score of 0.95. In other words, for each genotype subtract its frequency in the normal group from the frequency in the MB group; then sum the differences. Consequently, healthy control individuals predominately have negative scores while affected individuals have positive ones

Metric to score samples: A metric to score samples was designed based on their unique distribution of microsatellite genotypes. Essentially, the metric was a weighted sum of the genotypes belonging to each sample: weights stemmed from the difference in frequency for each genotype in the MB and healthy groups. A visual summary of the metric is provided in FIG. 13.

ROC analysis: receiver operating characteristic (ROC) analysis was used to design a classification scheme capable of differentiating samples with MB from healthy controls. Briefly, the area under the ROC curve (AUC) was used as a measure of how well scores in the two groups differentiate the two groups. Then, a cutoff was selected for all future classification. Here, the cutoff was a single score that minimizes sensitivity and simultaneously maximizes specificity; it was identified using the Youden index. ROC analysis, AUC calculation, and Youden index optimization were performed using a freely available R package: ROCR.

Subset of Microsatellites (Genetic Algorithm)

Genetic algorithms can be a class of biologically inspired algorithms. Briefly, a genetic algorithm was used to identify the most informative subset of markers—from the set of 139—using a 2-step iterative process. First, the algorithm was initialized with random subsets of the 139 microsatellite markers; next, the top preforming subsets were continuously recombined, reassessed, and re-ranked. Three hyperparameters (e.g., parameters set before the iterative algorithm began) were used to control the maximum population size, the size of each subset, performance of each subset, and diversity of the subsets in the population. Details of each step and hyperparameters are provided below.

Initialization: Each subset in the initial population consisted of markers chosen at random from the full complement of 139. Hyperparameters control the initial population size and the size of each subset. Once populated, the initial subsets were ranked based on a performance metric described below.

Optimization: Each optimization cycle began by placing 10 new subsets in the population; among these, 7 were generated by recombining 2 members (chosen at random) of the existing population and 3 were generated randomly. To recombine 2 subsets, each was split; then, two fragments (one from each subset) were rejoined. The split point and fragments were chosen randomly. The 3 random subsets were generated in initialization and help to maintain the diversity of the population. Once the new subsets were generated, the population was re-ranked based on a performance metric. Finally, the 10 worst performing subsets were discarded to maintain population size.

Hyperparameters: A population size of 100 subsets was initialized and used throughout the algorithm. The minimum and maximum size of subsets was set to 8 and 64 markers, respectively. Duplicate markers were not allowed in subsets. The performance of each subset was determined by ROC analysis using 120 MB samples and the 425 healthy controls, e.g., the same training samples used throughout this study. The sum of sensitivity and specificity dictated performance of each subset and was used to perform ranking of the population in each generation of the genetic algorithm.

Robustness: The parameters of the genetic algorithm were chosen for computational feasibility. However, the outcome of the genetic algorithm was insensitive to the choice of hyperparameters. In addition, the details of the optimization cycle (such as the number of new subsets in each cycle) did not affect the results of the genetic algorithm.

Validation

Figure 7A:
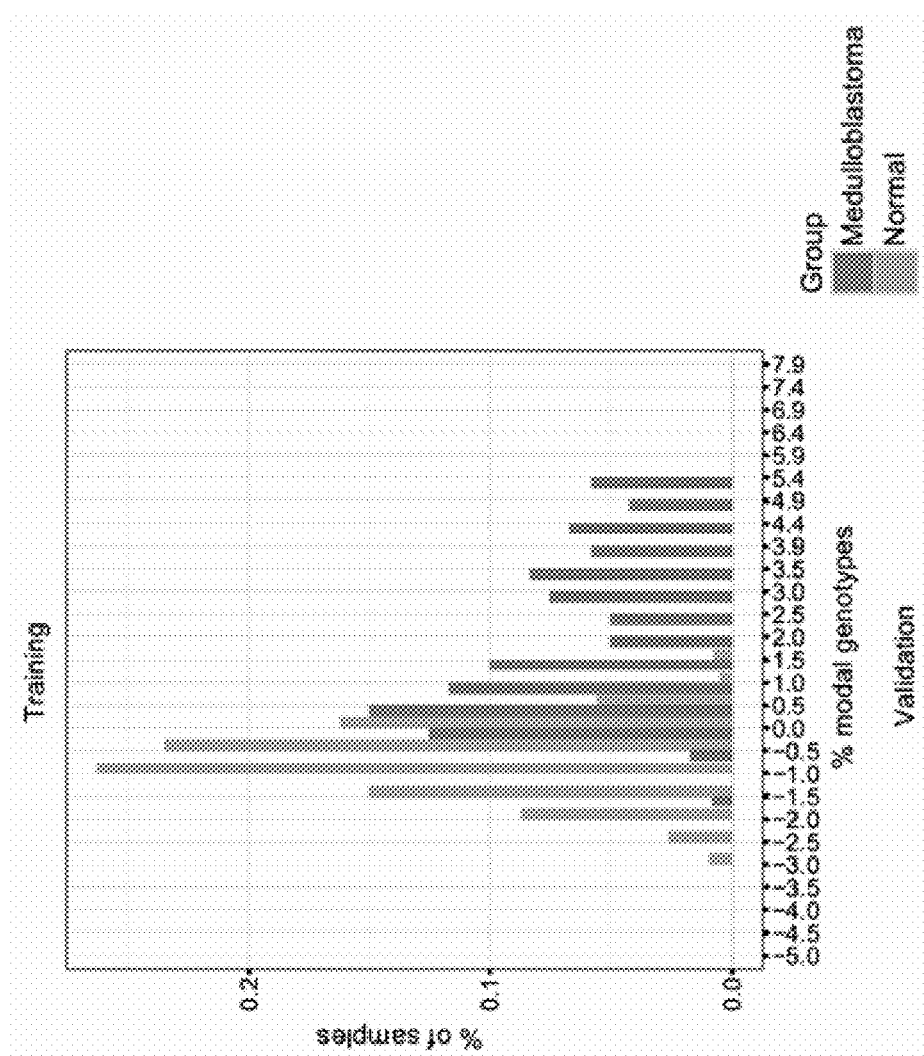
FIGS. 7A-7D illustrate an example of validation and training data.

Samples used: to assure that the study would be more than sufficiently powered, 102 experimental subjects and 428 control subjects in the validation study were chosen. Using the subject (MB) and control distributions found when analyzing the training set (FIG. 7A), the response within each subject group was normally distributed, with a standard deviation of 1.1. For the true difference in the experimental and control means of 4.4, rejection was made based on the null hypothesis that the population means of the experimental and control groups were equal with probability (power) greater than 0.99 for a Type I error probability of 0.01 with this sized sample and control validation sets. All control samples used in training and validation were subjected to whole exome sequencing. For MB, the collection included both whole exome and whole genome samples. Whole genome sequencing samples were exclusively used for validation.

Procedure: Each validation sample was scored with the same metric used for the training samples. The cutoff (identified in training) was used to predict which of the 530 validation samples had MB and which were healthy controls. MB was predicted for validation samples above the cutoff. Predictions were compared to the known identity of the 102 MB samples and 428 healthy controls. Sensitivity and specificity of these predictions were comparable to training.

Microsatellite Mutability

In order to test whether individuals with MB were more prone to microsatellite variation, the total number of alleles genotyped for each microsatellite (allelic load) was used as a measure of its mutability, and this metric was compared across disease and control cohorts. Alleles were defined such that the counts made were robust to two sources of error: (a) the potential effects of PCR artifacts were mitigated by requiring that each allele is supported by at least 2 reads; and (b) to normalize for differences in read coverage across samples each allele was required to be supported by at least 20% of the total number of reads mapped to the microsatellite. Alleles were only counted for microsatellites with mapped reads present in at least 20 percent of the samples. Then, a Fishers exact test was performed to establish statistical significance between MB patients and healthy individuals. This process was repeated 50 times with an average p-value of 0.077.

The integrity of mismatch repair mechanisms in medulloblastoma germline was also assessed using two additional lines of evidence: (a) homozygote and heterozygote genotypes tallied over all (71,192 total) microsatellites in MB and control samples; and (b) a comparison of median microsatellite array lengths over all microsatellites (71,192 total) in MB and control samples. For the former analysis, aberrant mismatch repair can be expected to increase the count of heterozygote genotypes; however, the difference in case and control samples was not statistically significant. Medulloblastoma samples together had 299,802 heterozygous genotypes and 2,596,324 homozygous genotypes; control samples had 283,037 heterozygous genotypes and 2,449,046 homozygous genotypes. For the latter analysis, aberrant mismatch repair can be expected to lead to the accumulation of longer or shorter median microsatellite array lengths in medulloblastoma samples compared to controls; again, the results were not statistically significant. Medulloblastoma samples had shorter median array length for 1,031 microsatellites and longer median array length for 907 microsatellites; the remaining 69,254 microsatellites had no difference in median array length.

Downstream Analysis

Genes associated with the 139 microsatellites loci whose genotypes were significantly different between MB subjects and controls were used for functional analysis. In total, 124 genes were included in the analysis, excluding the microsatellites located in intergenic regions. Pathway analysis was performed using Ingenuity Pathway Analysis (QIAGEN Inc.) Mutations and co-occurrence were analyzed using PedcBioPortal. Protein-protein interaction (PPI) network construction was conducted with STRING with a minimum interaction score of 0.7 (high confidence) and no more than five molecules in the first shell. This setting generated a hub with 129 nodes and 49 edges resulting in a network with a PPI enrichment p-value of 0.0007.

Results

Identification of Medulloblastoma Microsatellite Informative Loci

Figure 6:
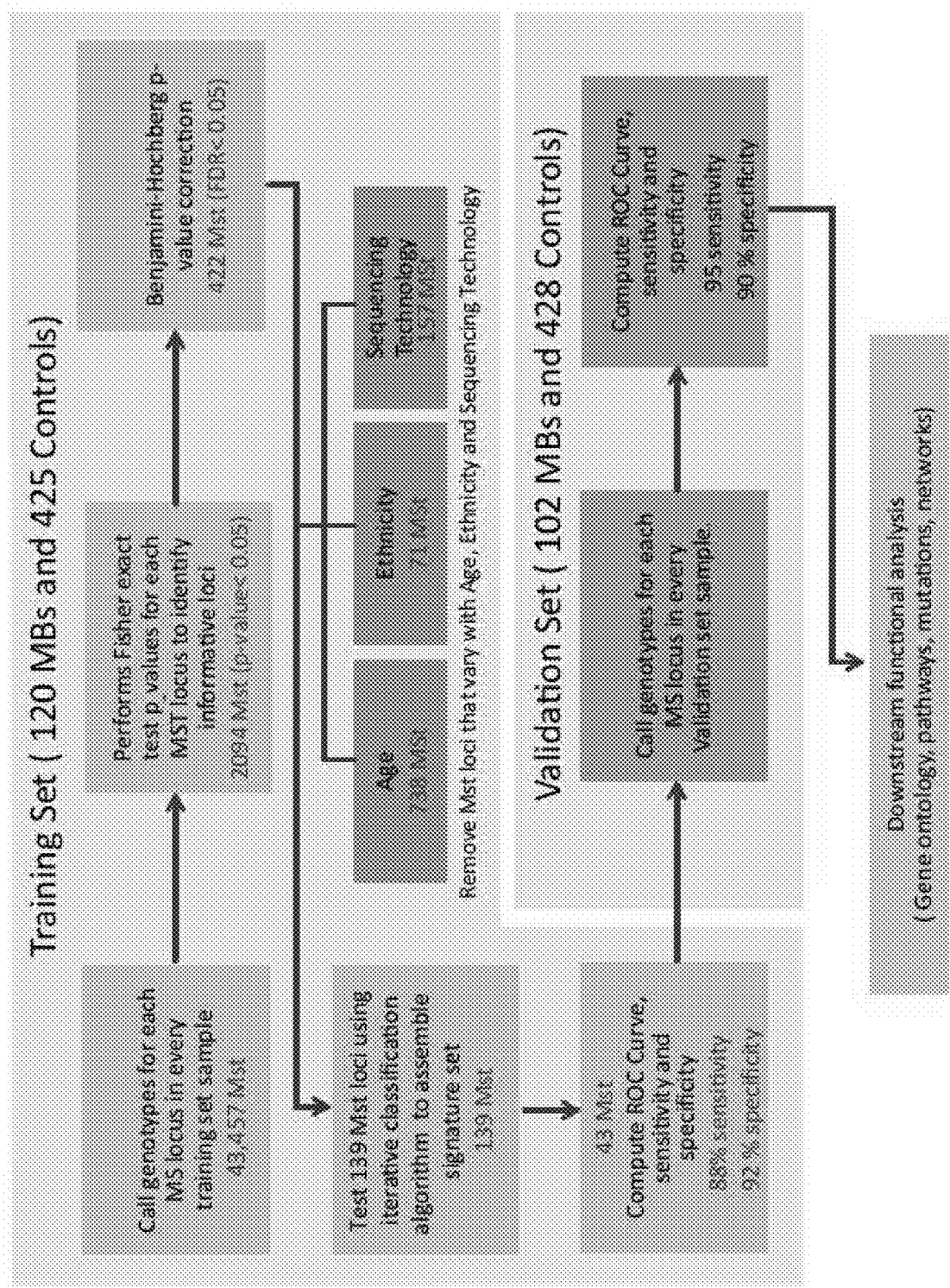
FIG. 6 illustrates a schematic representation of an approach used for the identification and validation of medulloblastoma (MB) associated MSs. The approach comprises 3 stages: Computational identification of informative MSs loci using the training set, validation of the microsatellite markers in an independent validation cohort, and downstream analysis of the genes associated with those MSs. The first stage includes a filter to eliminate MSs that vary with age, ethnicity, and sequencing technology.

Single nucleotide mutations can be characterized in MB genome-wide analyses. Here, the impact of microsatellite variations in medulloblastoma predisposition were studied. For this purpose, a computational workflow was developed to identify germline microsatellites whose genotypes differ between children with medulloblastoma and control subjects while correcting for those that vary with age, ethnicity, and DNA sequencing protocol (FIG. 6). A metric was also developed to score each sample based on its unique collection of microsatellite genotypes. This approach was applied to germline DNA sequencing data from 222 children with medulloblastoma and 853 healthy control subjects. The data was divided into 2 groups, both containing affected and healthy subjects, the first for training containing 120 medulloblastoma patients and 425 control individuals, and the second for validation having 102 medulloblastoma patients and 428 controls individuals. In the first phase of analysis, using the training set, 43,457 different microsatellites present in both the 120 medulloblastoma samples and the 425 healthy controls were genotyped. For each of these microsatellites, a generalized Fisher's exact test was used to assess the statistical difference in genotype distribution between the two groups for each microsatellite. 2,094 microsatellites were identified with a p-value<0.05. After Benjamini-Hochberg multiple testing correction ($\alpha$=0.05), 422 passed false discovery. Three additional steps were performed to remove microsatellites that vary with age, ethnicity, and DNA sequencing protocol (FIG. 6, FIG. 10, FIG. 11, and FIG. 12). In total, 283 microsatellites were removed from the list of 422 resulting in a reduced list of 139 (FIG. 19). In summary, this approach identified 139 microsatellites from germline DNA whose genotypes were significantly different between medulloblastoma subjects and healthy controls.

Medulloblastoma Microsatellite Classifier Set

Figure 7B:
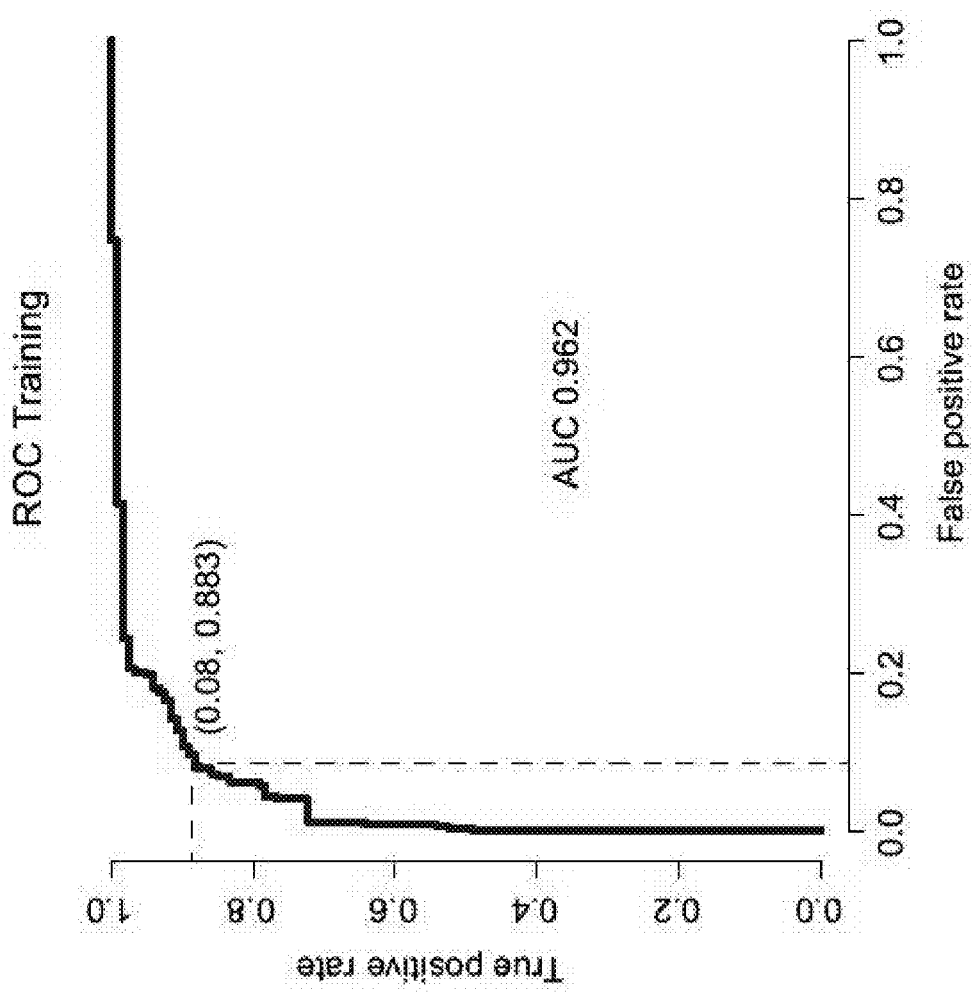
Figure 14:
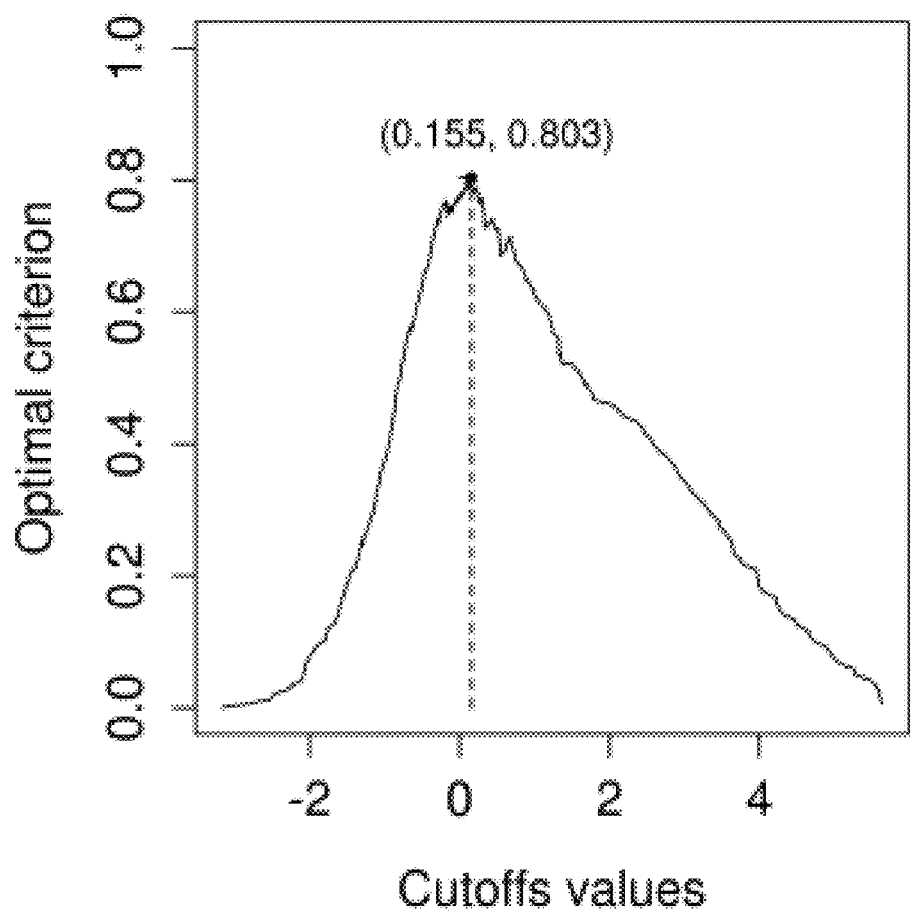
FIG. 14 illustrates a Youden index to determine the criteria for differentiating MB and healthy samples. The Youden index was used to determine the cutoff for the ROC curve in the training set. The optimal criterion for the list of 43 markers is 0.155. The same criteria were used to calculate the specificity and sensitivity of the validation cohort.
Figure 15:
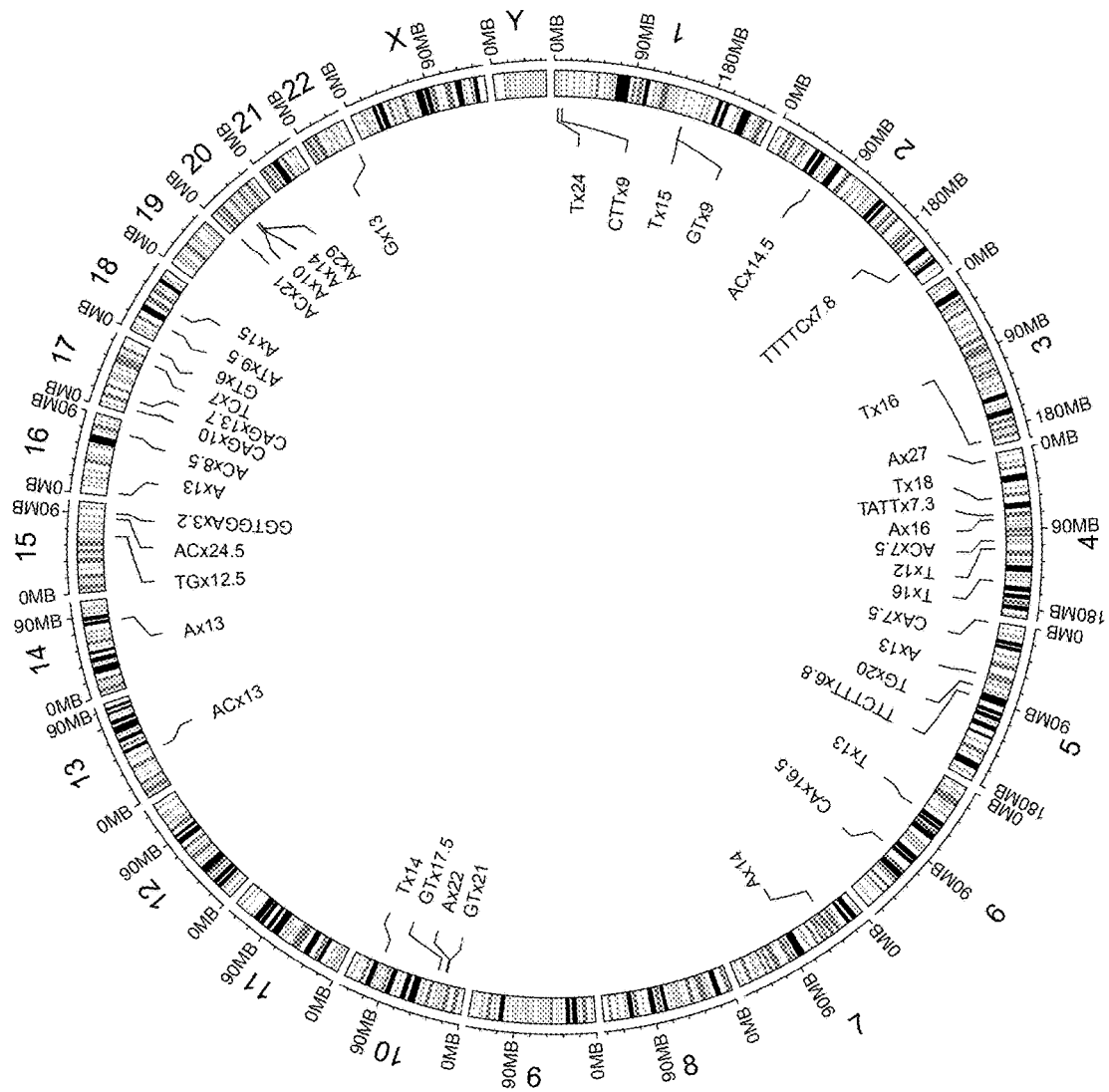
FIG. 15 illustrates a circos plot that indicates the chromosomal locations of 43 informative loci for MB.

In order to identify a subset of microsatellites with the best performance in distinguishing medulloblastoma samples and healthy controls, the set of 139 microsatellites was used to train a medulloblastoma classifier. First, a metric was designed to score each medulloblastoma and control sample based on the genotypes of the 139 microsatellites (see Methods and FIG. 13 for details). Next, a receiver operating characteristic (ROC) was generated and used to determine the ability of the sample scores to serve as a binary classifier for medulloblastoma. A subset optimization strategy based upon a genetic algorithm method was used to identify the best subset of discriminating markers using a 2 step iterative process. First, subsets were generated randomly from the complete list and ranked by their F-measure. Second, the top performing subsets were continuously mixed, reassessed, and re-ranked. The algorithm converged in 87 cycles to reveal a subset of 43 microsatellites with an F-measure of 0.90 and an Area Under the Curve (AUC) of 0.962 (FIG. 7, FIG. 20). The Youden's index was determined, which indicated that the optimal cutoff score for differentiating medulloblastoma samples from healthy controls was 0.155 (FIG. 14). The sensitivity when applied to the training set was 0.88 with a specificity of 0.92 (FIG. 7B). The chromosomal location of these 43 markers in the human genome is shown in FIG. 15. Thus, a set of 43 microsatellites was identified and whose genotype distributions were able to distinguish medulloblastoma patients from healthy controls with 88% sensitivity and 92% specificity.

Figure 7C:
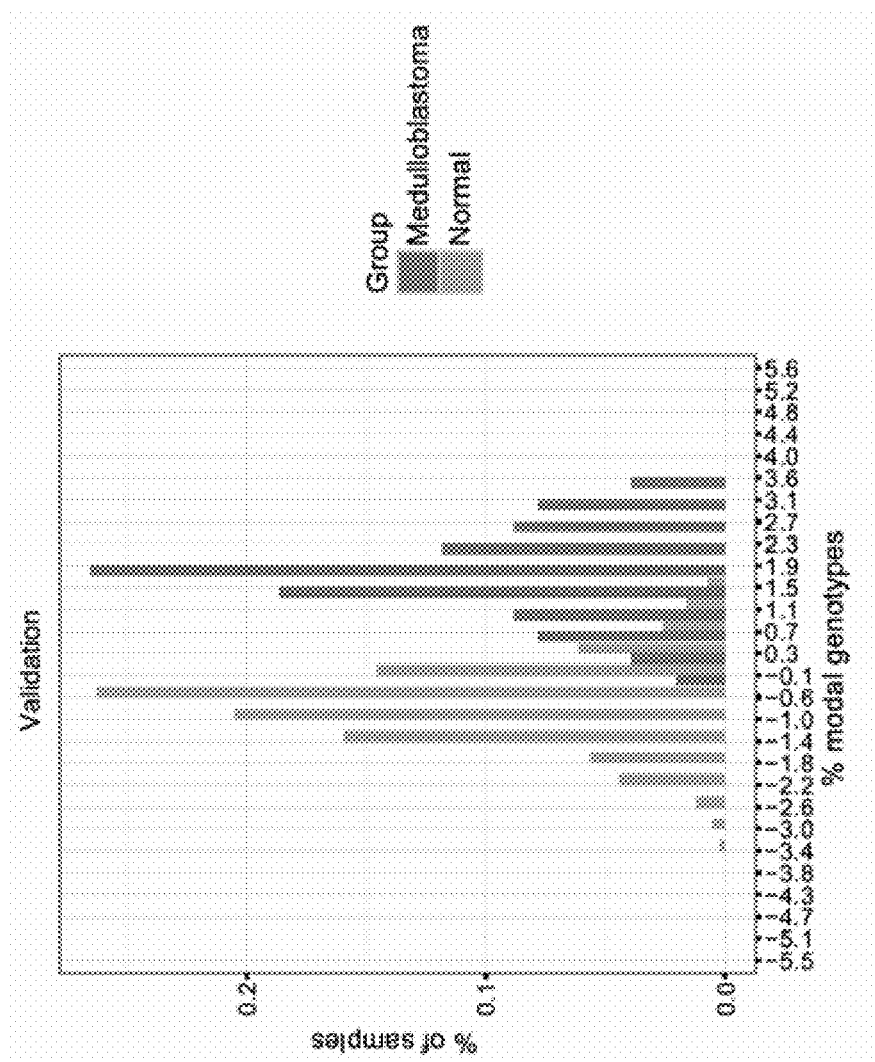
Figure 7D:
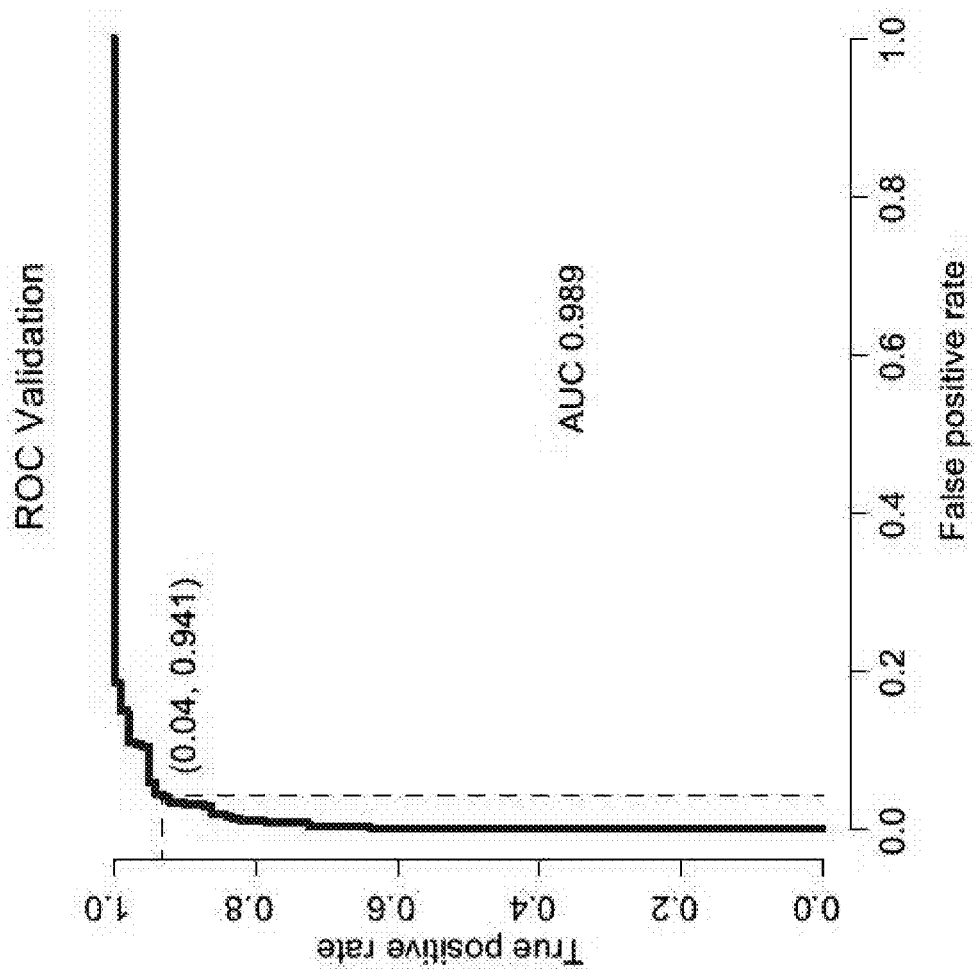

An independent cohort of germline DNA from medulloblastoma patients and healthy controls were used to validate the previous results. For the validation study, 102 experimental subjects and 428 control subjects were included, and used the subject (medulloblastoma) and control distributions found when analyzing the training set (FIG. 7), to assure that the study would be more than sufficiently powered. In the training set, the response within each subject group was normally distributed, with a standard deviation of 1.1. For the true difference in the experimental and control means of 4.4, it was found that rejection can be made for the null hypothesis that the population means of the experimental and control groups were equal with probability (power) greater than 0.99 for a Type I error probability of 0.01 with this sized sample and control sets. The optimal cutoff (0.155) was applied to the independent validation sample set, and it was found that the classifier was able to distinguish cases from controls with a sensitivity of 0.95 and specificity of 0.90 (FIG. 7C and FIG. 7D). In summary, a set of 43 MSs whose genotype distributions were identified and validated to be able to distinguish MB patients from healthy controls using germline DNA with high sensitivity and specificity.

Medulloblastoma Informative Microsatellite Loci Mutability

In the germline, rates of indels in MSs are significantly higher than rates of single nucleotide substitutions elsewhere in the genome, $10^{-4}$ to $10^{-3}$ compared with $10^{-8}$ per locus per generation respectively. However, mutation rates also vary for different MSs based on the length of the repeat, their repetitive motif, and influence on DNA folding. It was hypothesized that the differences found for the 139 MSs (FIG. 20) whose genotypes were non-randomly associated with MB can be the result of increased microsatellite genotype variation inherent in the individual with MB. In order to test whether individuals with MB were more prone to microsatellite variation, the total number of alleles genotyped for each microsatellite (allelic load) was used as a measure of its mutability, and this metric was compared across disease and control cohorts. There was no significant differences in the number of genotyped alleles between healthy and MB individuals, supporting the conclusion that there was not a general microsatellite instability in MB patients. The predictive capability was investigated for relating to a characteristic of the informative microsatellites themselves, by ranking all of the MSs by allelic load to determine whether the 139 markers reside among the most mutable loci analyzed. It was found that while they were among the more mutable MSs, they did not comprise the most mutable sites. Additionally, the number of homozygote and heterozygote genotypes and the microsatellite array lengths were compared as a potential source of variability in MB. In both cases, there was no statistically significant difference between MB and control germline DNA. These results and data indicate that the association of those 139 MSs with MB was a consequence of those individual microsatellites' genotypes rather than simply being a result of constitutional hypermutability.

Role of the Informative MST Associated Genes

Figure 8A:
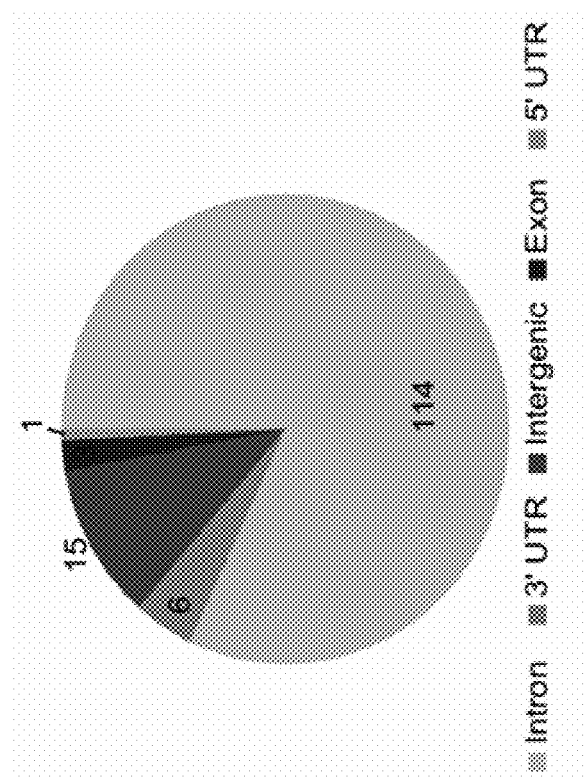
FIG. 8A illustrates a pie chart displaying the genomic locations of the 139 MSs informative loci for MB.
Figure 8B:
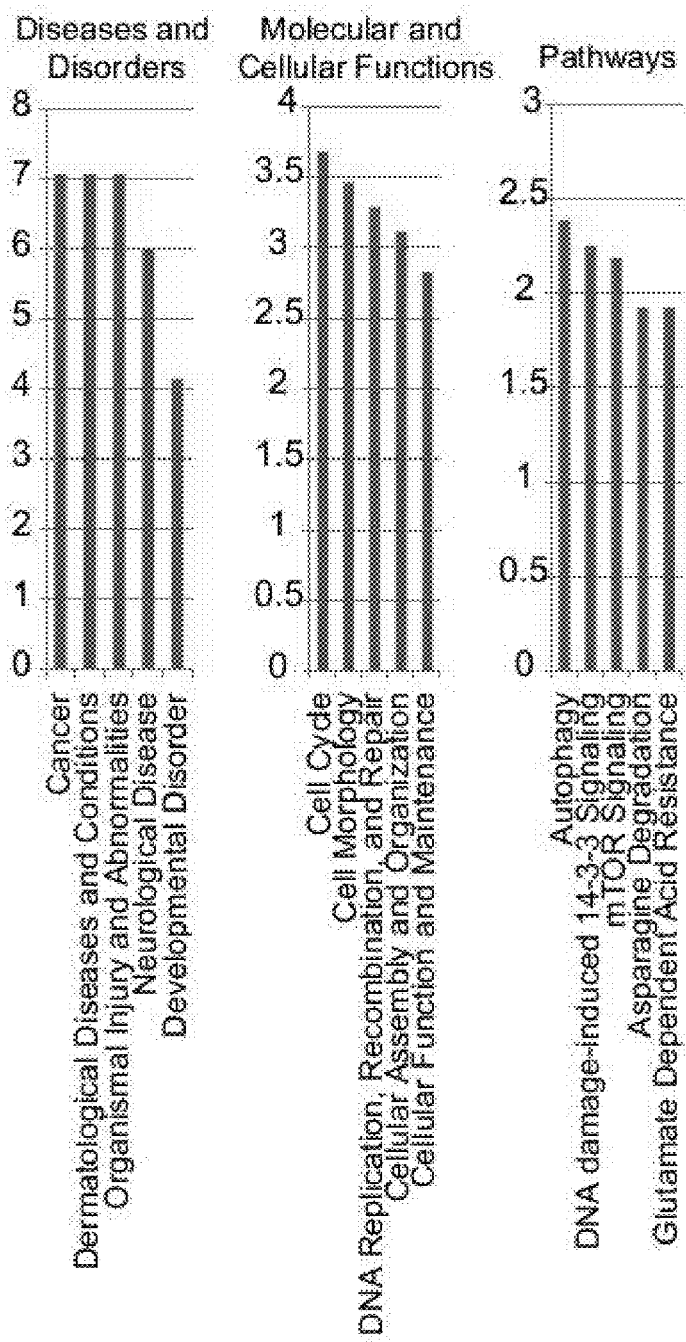
FIG. 8B illustrates Gene Ontology analysis of informative medulloblastoma MS loci.

Of the 139 MS loci whose genotypes were different between MB and control samples, 114 were located in intronic regions, 15 in intergenic regions, 6 in 3'UTRs, 3 in exonic regions, and 1 in a 5'UTR (FIG. 8A). To understand the potential mechanistic roles of these genes, an Ingenuity Pathway Analysis® was conducted to analyze the 124 genes associated with informative MS loci (excluding MSs located in intergenic regions). The analysis revealed statistically significant associations with cancer and molecular cellular functions such as cell cycle, DNA replication, recombination and repair, and cellular growth and proliferation, indicating a relationship to cancer biology (FIG. 8B and FIG. 21). The occurrence of mutations in these 124 genes associated with informative MSs was examined in 4 MB cohorts available in cBioportal. In spite of the known low mutation rate in MB tumors, on average 17% of the MB cancer samples contained mutations in at least one of these 124 genes (FIG. 22) compared to 4.5% of neuroblastoma tumors. An analysis of mutations co-occurrence, using the Sick Kids 2016 dataset within cBioportal, indicated that 135 out of all possible (9,591=139*(139-1)/2) microsatellite pairs were found to significantly co-occur (p-value<0.05). Two patients were found with co-occurrence of mutations in 20 and 10 MB informative MS loci, respectively (FIG. 23).

Figure 8C:
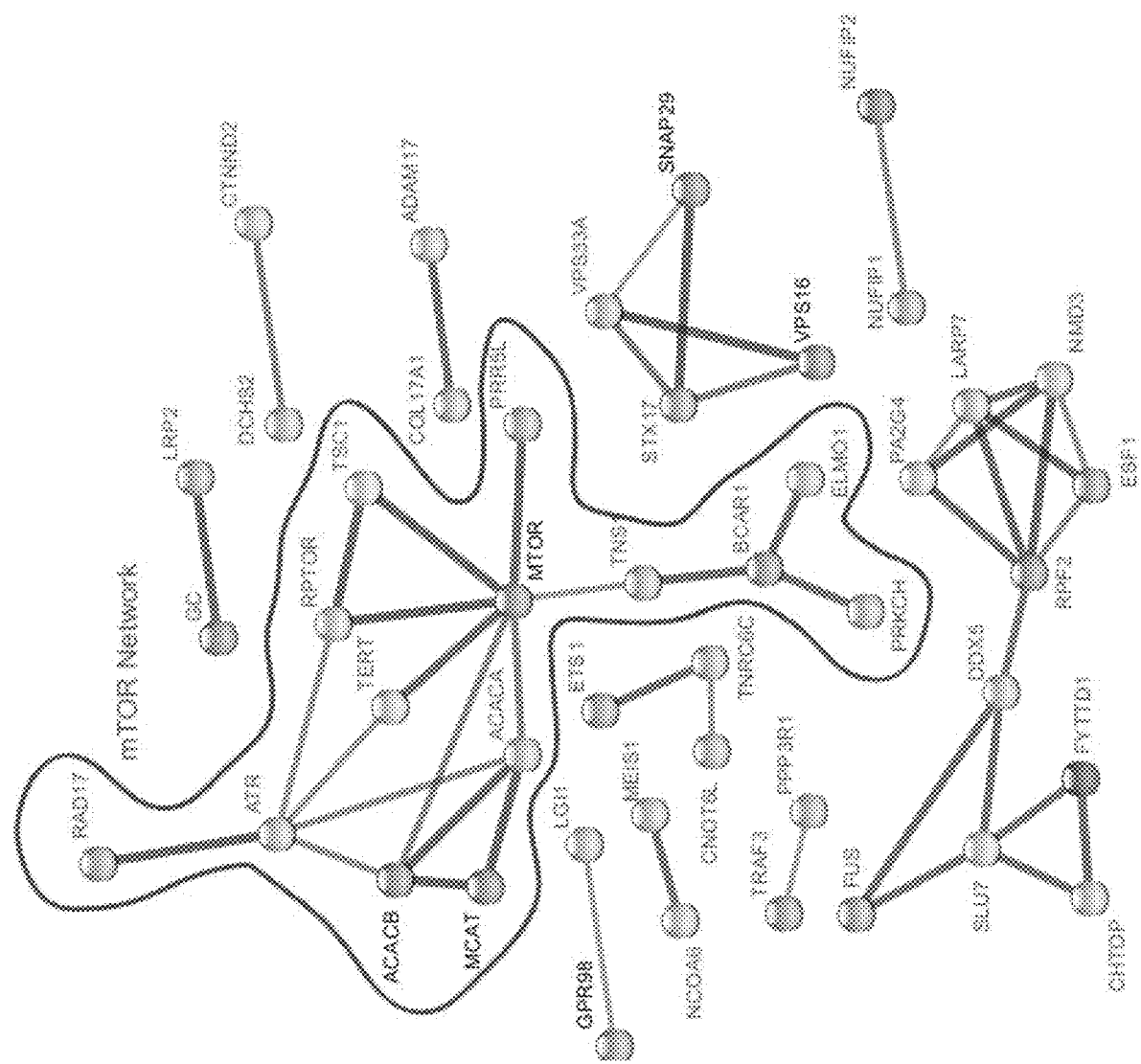
FIG. 8C illustrates a Protein-protein interaction (PPI) network of the 124 genes associated with the informative MS loci. The PPI contains 129 nodes and 49 edges resulting in a network with an enrichment p-value of 0.0007.

A protein-protein interaction (PPI) network comprised of the 124 genes associated with the informative MS loci (FIG. 8C) was found to contain 129 nodes and 49 edges, resulting in a network with a PPI enrichment p-value of 0.0007. Despite the low number of proteins used as input, a significant hub related to mTOR, a prominent pathway (PI3K/AKT/mTOR) in MB tumors.

Figure 16:
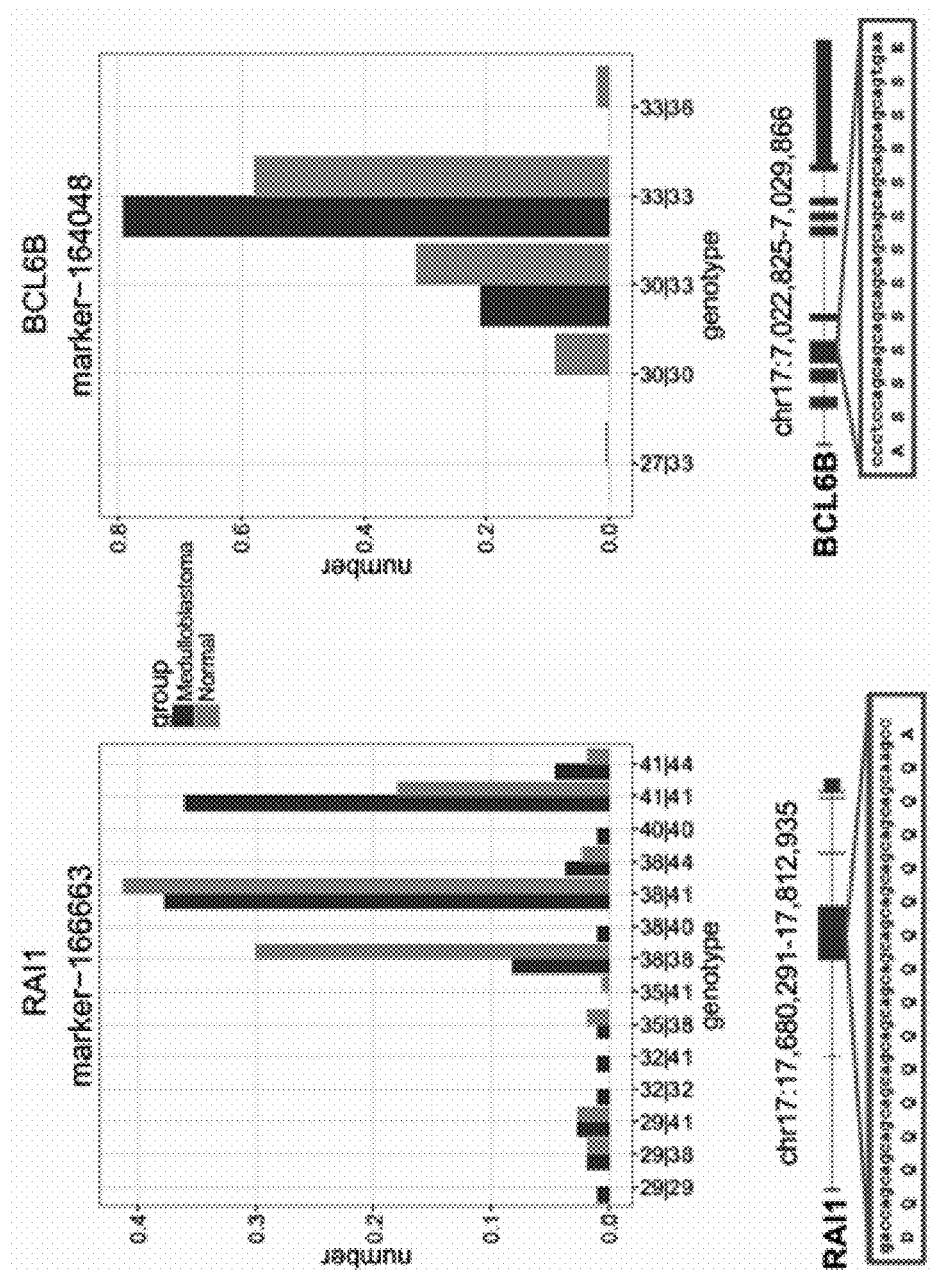
FIG. 16 illustrates a distribution of genotypes for the microsatellite markers 166663 (exonic microsatellite located in RAI gene) and 164048 (exonic microsatellite located in BLC6B gene). The addition of one CAG triplet can change protein structure impairing its function, similar to a missense mutation.

Three informative microsatellite loci were located in protein coding sequences (FIG. 8A); all of them were trinucleotide repeats (RAI1 BCL6B, TNS1). Variation of trinucleotide repeats was recognized as a cause of neurological and neuromuscular diseases such as Huntington's disease, spinocerebellar ataxia, and Fragile X Syndrome. Two of these genes (RAI1 BCL6B) were transcription factors located in the short arm of the chromosome 17, the deletion of which was a recurrent alteration in the most common subgroups of MB tumors. The BCL6B gene had been implicated in colon, gastric and hepatic cancer and the major genotype in MB tumors is 33/33 while in control is 30/33 (FIG. 16); in this reading frame, the codon CAG translated to serine. RAI1 (Retinoid acid-induced protein) encodes for a nuclear protein with unknown function whose haploinsufficiency causes Smith-Magenis syndrome. The two major genotypes for RAI' in MB tumors were 38/41 and 41/41, while in control they were 38/38 and 38/41 (FIG. 16). Apart from inducing changes in the RAI' protein structure, short polyglutamine expansions were also thought to modulate transcription factor activity. The RAI' protein is highly expressed in cerebellum, the region where MB tumors arise.

In this study, a set of 139 MSs was identified to possess genotypes that were differing between MB patients and healthy controls. A subset of 43 MSs was able to differentiate MB individuals from controls based upon their germline DNA, with a sensitivity and specificity of 0.95 and 0.90, respectively.

This study identified 3 sets of microsatellites: (a) 43 microsatellites that together differentiated medulloblastoma samples and healthy controls; (b) 139 microsatellites that had genotypes that statistically differed between medulloblastoma samples and healthy controls; and (c) 422 microsatellites identified in initial screen. Microsatellites in all three sets passed false discovery. The set of microsatellites identified in the initial screen (c) contained 283 sensitive to age, ethnicity, and/or DNA sequencing; consequently, none were used in subsequent analysis. Some of the microsatellites with ethnic bias also can have a role in medulloblastoma. The prevalence of many diseases—medulloblastoma included—can show ethnic differences. Thus, a re-examination of the 283 microsatellites can be feasible once more is known about the genetic mechanisms that cause medulloblastoma.

Further, the relationship between the group of 139 microsatellites (b) and its subset of 43 microsatellites (a) was investigated: the latter distinguished Medulloblastoma samples from healthy controls, while the former did not. Mutations in the set of 43 microsatellites can have a greater impact on gene expression; or, the genes harboring those microsatellites can have a greater effect on disease onset. This can be supported by the presence of two coding microsatellites in the set of 43; in both cases, mutations can have a direct impact on protein primary structure with potential impacts on secondary structure and function. In addition, the set of 43 microsatellites had a greater proportion embedded in 5' and 3' UTR regions; it can be that MSs in these regions more strongly affected gene expression/translation. These indications can be determined with expression studies of these genes harboring informative microsatellites in tumor tissue.

These results indicate that polyglutamine microsatellites imbedded in the BCL6B and RAI' genes can play a role in medulloblastoma. Only 181 polyglutamine microsatellites (out of 627,174) were present in the complete list of screened microsatellites. Thus, chance alone may not explain the presence of 2 in the final list 43 informative microsatellites; using computer simulation it was estimated that the chances of this occurring randomly to be approximately 1 in 1,000,000. Second, polyglutamine microsatellites can play a role in diseases such as spinal and bulbar muscular atrophy, Huntington's disease, and various spinocerebellar ataxias. Moreover, both the BCL6B and RAI' genes can be associated with diseases; the former with Lymphoma and the latter with Smith-Magenis syndrome. Polyglutamine diseases can be characterized by insoluble protein aggregates: something not seen in some cancers. On the other hand, polyglutamine expansions can confer both gain and loss of functions depending upon the affected protein.

This study demonstrated two overall conclusions. First, the microsatellites identified—particularly the set of 139 and subset of 43—can play a role in medulloblastoma etiology. Effects of microsatellite array length variations included effects on DNA secondary structure, nucleosome positioning, and DNA binding sites. Three of the microsatellites identified affected protein primary sequence. Microsatellites can assist in differentiating individuals with medulloblastoma from healthy controls; the classification scheme demonstrated high sensitivity and specificity of 0.95 and 0.90, respectively.

The treatment for medulloblastoma can leave survivors with lifelong burdens including hearing loss, cognitive deficits, endocrinopathies, and a heightened risk of stroke and secondary malignancies. Identification of a population at risk for the development of medulloblastoma can make possible early detection strategies allowing for less invasive, more localized means of tumor control. However, an effective way to improve the lives of these children can be to prevent their tumors from forming. The recent advances in immunotherapy including cancer vaccines create the potential to immunize an individual against tumor specific antigens. Such a strategy can require the selection of individuals appropriate for such an intervention.

Example 2: Informative Microsatellite Marker Identification

Samples of nucleic acid sequences of both subjects with a condition (first group) and healthy controls (second group) are obtained from public domain databases. Microsatellite loci are identified in both groups. Microsatellites are compared to reveal a difference in the microsatellite loci that only found in the first group and are specifically associated or correlated with the condition. Statistical analysis and modeling are applied to these different microsatellites for their association or correlation to the condition. In some instances, the microsatellites are statistically weighted. After a set of microsatellites have been identified to be strongly linked to the condition, these microsatellites are assembled into a training algorithm to further optimize the accuracy, sensitivity, and specificity of these microsatellites linking to the condition. The microsatellites during training can be randomly recombined to generate additional combinations of microsatellites. Upon completion of the training, the algorithm can be validated with additional independent sets of samples.

For example, nucleic acid sequences of cancer patients and corresponding healthy controls are downloaded from The Cancer Genome Atlas (TCGA) and Thousand Genomes Project respectively. Microsatellite loci are identified in both groups. Comparison of the microsatellite between the two groups reveal a population of microsatellite loci that are only found in the cancer patient group and are specifically associated or correlated with a type of cancer. These microsatellites linked to the type of cancer are then subjected to the training algorithm to enhance the accuracy, sensitivity, and specificity of these microsatellites in being linked to cancer. Upon completion of the training, the algorithm is validated with additional sets of samples that either harbor cancer or are from heathy controls. After validation, the algorithm is ready for application with patient samples.

Example 3: Risk Assessment in a Patient

A serum sample is isolated from a subject during routine health check-up. DNA is extracted from the serum sample and sequenced. The sequencing data is processed and analyzed to yield a set of microsatellites that is unique to the subject. This set of microsatellites is then analyzed using computer-implemented methods that are designed to determine risks to developing cancer based on the comparison between the subject's microsatellites and microsatellites from pan-cancer databases. Each of the identified informative microsatellites is assigned a weight, ranging between 0 to 1. The weights are generated based on accuracy, sensitivity, and specificity of the identified microsatellites. A sum of the weights is then determined and used to create a classifier for a likelihood of developing one type of cancer. The pan-cancer classifier then compiles and reports a plurality of classifiers for a plurality of likelihood of developing a plurality of cancer for risk assessment for the subject. The pan-cancer classifier provides a risk assessment of the likelihood of the subject developing cancer, e.g., breast cancer, lung cancer, prostate cancer, cervical cancer, Glioblastoma Multiforme, Uterine Corpus Endometrial Carcinoma, Colon Adenocarcinoma, Bladder, Urothelial Carcinoma, Head and Neck Squamous Cell Carcinoma, Cervical Squamous Cell Carcinoma and Endocervical Adenocarcinoma, Stomach Adenocarcinoma, Thyroid Carcinoma, Brain Lower Grade Glioma, Kidney Renal Papillary Cell Carcinoma, and Liver Hepatocellular Carcinoma.

The subject is notified of the risk assessment by a laboratory report (FIG. 5 and FIG. 17). Information of the patient, healthcare professional, and the serum sample is listed along with the testing summary. The summary reveals that while the subject is currently cancer free, there are several identified microsatellites in the subject's genome that increase the subject's likelihood of developing lung cancer. A classifier of likelihood of developing lung cancer comprises a numerical output and is compared to a threshold for the likelihood of developing lung cancer. The threshold value for likelihood of developing lung cancer is 0.3, with 1 standard deviation range of 0.1 and 0.5 (FIG. 24). The classifier of likelihood of developing lung cancer for the subject is 2.3, which indicates that the subject is highly likely of developing cancer in the future. Accordingly, additional clinical attention is given to the subject's lungs and respiratory systems. More routine imaging of the lungs is recommended to be conducted periodically. The subject is also advised not to start smoking and to avoid prolonged exposure to certain environments with known aerosolized carcinogens. Further, the summary provides an outline on the parameters of the risk assessments, e.g., the types of statistical methods and thresholds that are utilized and the number of microsatellite loci that are analyzed.

Example 4: Measuring Genomic Age Using Minor Alleles

Samples of DNA from primary skin fibroblasts are obtained from a subject at age of 17 and again at age of 30. DNA-seq libraries are constructed and subsequently sequenced with a next-generation sequencing platform and mapped to hg19. An enrichment can be carried out to enrich for the hotspots where minor alleles tend to arise in a population. Minor alleles with a minimum of 5 reads are independently confirmed with Sanger sequencing. The true positive minor alleles are analyzed and weighted. Examples of locations where minor allele emerges includes upstream or downstream of a gene, exonic region, intergenic region, region spanning intron and exon, 3'UTR, and 5'UTR. The minor allele can be nonsynonymous variants, synonymous variants, frameshift indels, non-frameshift indels, stopgain, stoploss, or a combination thereof.

The minor alleles obtained from the comparison between the sample obtained at age of 17 and the hg19 reference sequence is analyzed by computer-implemented methods to reveal a genomic age. Increased number of minor alleles or the loci of the minor alleles can contribute to a genomic age that is more senescent than the subject's real age and physical fitness. The samples obtained at age 17 and age 30 from the same subject can be compared to each other to reveal additional accumulation or shift in patterns of minor alleles within the same subject. Comparison of the minor alleles between age 17 and age 30 reveals that the subject has a slight increase in the total number of minor alleles. This increase is analyzed by computer-implemented methods to reveal an accelerated rate of genomic aging in the subject. Accordingly, the subject is advised to adopt a certain life style that emphasizes a balance in nutrition and a reduction in mental stress.

While preferred aspects of the present examples have been shown and described herein, it will be obvious to those skilled in the art that such aspects are provided by way of example only. Numerous variations, changes, and substitutions will now occur to those skilled in the art without departing from the disclosure. It should be understood that various alternatives to the aspects of the disclosure described herein can be employed in practicing the disclosure. It is intended that the following claims define the scope of the disclosure and that methods and structures within the scope of these claims and their equivalents be covered thereby.

What is claimed is:

1. A method for treating a cancer in a subject identified with an optimized classifier for the cancer, the method comprising:
   (a) training in a machine learning model by a computer, wherein the training comprises:
      (i) weighting an initial population of microsatellite loci as indicators of the cancer;
      (ii) obtaining subsets of the initial population of microsatellite loci, wherein a number of microsatellite loci in each of the subsets is an order of magnitude lower than a number of microsatellite loci in the initial population of microsatellite loci;
      (iii) performing a plurality of optimization cycles, wherein an optimization cycle of the plurality of optimization cycles comprises:
         (1) generating a first new subset of microsatellite loci by a process comprising:
            (A) randomly selecting microsatellite loci from a first combination of the subsets from (a) (ii) and combining the microsatellite loci to produce the first new subset, wherein the first new subset is distinct from any subset in the subsets from (a)(ii); and
            (B) performing a first receiving operating characteristic (ROC) analysis with (1) the microsatellite loci from the first new subset, (2) microsatellite loci obtained from a first portion of the reference subjects with the cancer, and (3) microsatellite loci obtained from a second portion of the reference subjects without the cancer;
         (2) generating a second new subset of microsatellite loci by a process comprising:
            (A) randomly selecting microsatellite loci from a second combination of the subsets from (a)(ii) to produce second new subset, wherein the second new subset is distinct from any subset in the subsets from (a)(ii); and
            (B) performing a second ROC analysis with (1) the microsatellite loci from the second new subset, (2) microsatellite loci obtained from a second portion of the reference subjects with the cancer, and (3) microsatellite loci obtained from a second portion of the reference subjects without cancer;
         (3) adding the first new subset and the second new subset to the initial population of the microsatellite loci when no previous optimization cycle has been performed, or adding the first new subset and the second new subset to subsets from the previous optimization cycle to generate a plurality of updated subsets of the initial population of the microsatellite loci;
         (4) for an updated subset of the plurality of updated subsets in (a)(iii)(3), determining a sum of a sensitivity and a specificity for the cancer from results of the first ROC analysis performed in (a)(iii)(1)(B) and the second ROC analysis performed in (a)(iii)(2)(B), wherein a higher sum indicates a higher probability of the cancer; and
         (5) weighting the updated subset using the sum of the sensitivity and the specificity, wherein a higher weight indicates a higher probability of the cancer; and
      (iv) comparing the weighted subset to a threshold weight, thereby identifying the weighted subset above the threshold weight as an indicator of the cancer;
   (b) determining that a subject has the cancer or is likely to develop the cancer with at accuracy of at least 95%, wherein a sample obtained from the subject comprises one or more microsatellite loci from the weighted subset in (a)(iv); and
   (c) treating the cancer in the subject, wherein the treating comprises performing surgery or delivering chemotherapy, radiation, cancer-targeted drug therapy, or an immune therapy treatment to the subject.

2. The method of claim 1, further comprising comparing microsatellite loci in a first set of samples from subjects with cancer and microsatellite loci in a second set of samples from subjects without cancer, thereby identifying the initial population of microsatellite alleles.

3. The method of claim 1, wherein the plurality of updated subsets comprises at least 100 subsets.

4. The method of claim 1, wherein a minimum number of microsatellite loci in a subset of the subsets selected from the initial population of microsatellite loci is 8 microsatellite loci.

5. The method of claim 1, wherein a maximum number of microsatellite loci in a subset of the subsets selected from the initial population microsatellite loci is 64 microsatellite loci.

6. The method of claim 1, wherein duplicate microsatellite loci are not allowed in a subset of the plurality of updated subsets of microsatellite loci.

7. The method of claim 1, wherein the first new subset or the second new subset comprises between 10 and 20 microsatellite loci.

8. The method of claim 1, further comprising discarding 10 subsets of the subsets selected from the initial population of microsatellite loci in an optimization cycle based at least in part on having a lowest sum in the optimization cycle.

9. The method of claim 1, wherein the threshold weight indicates an increased or decreased likelihood of developing the cancer in a subject.

10. The method of claim 1, wherein the cancer-targeted drug therapy comprises one or more of afatinab, gefinib, bevacizumab, crizotinib, and ceritinib.

11. The method of claim 1, wherein the one or more immunotherapy treatments comprise treatments with monoclonal antibodies, checkpoint inhibitors, therapeutic vaccines, or adoptive T-cell transfer.

12. A computer system configured to construct an optimized classifier for cancer, comprising:
  a memory comprising computer-executable instructions; and
  one or more processors, wherein when the one or more processors execute the computer-executable instructions, the one or more processors cause the system to:
  (a) train in a machine learning model by a computer, wherein the training comprises:
    (i) weighting an initial population of microsatellite loci as indicators of the cancer;
    (ii) obtaining subsets of the initial population of microsatellite loci, wherein a number of microsatellite loci in each of the subsets is an order of magnitude lower than a number of microsatellite loci in the initial population of microsatellite loci;
    (iii) performing a plurality of optimization cycles, wherein an optimization cycle of the plurality of optimization cycles comprises:
      (1) generating a first new subset of microsatellite loci by a process comprising:
        (A) randomly selecting microsatellite loci from a first combination of the subsets from (a)(ii) and combining the microsatellite loci to produce the first new subset, wherein the first new subset is distinct from any subset in the subsets from (a)(ii); and
        (B) performing a first receiving operating characteristic (ROC) analysis with (1) the microsatellite loci from the first new subset, (2) microsatellite loci obtained from a first portion of the reference subjects with the cancer, and (3) microsatellite loci obtained from a second portion of the reference subjects without the cancer;
      (2) generating a second new subset of microsatellite loci by a process comprising:
        (A) randomly selecting microsatellite loci from a second combination of the subsets from (a)(ii) to produce second new subset, wherein the second new subset is distinct from any subset in the subsets from (a)(ii); and
        (B) performing a second ROC analysis with (1) the microsatellite loci from the second new subset, (2) microsatellite loci obtained from a second portion of the reference subjects with the cancer, and (3) microsatellite loci obtained from a second portion of the reference subjects without cancer;
      (3) adding the first new subset and the second new subset to the initial population of the microsatellite loci when no previous optimization cycle has been performed, or adding the first new subset and the second new subset to subsets from the previous optimization cycle to generate a plurality of updated subsets of the initial population of the microsatellite loci;
      (4) for an updated subset of the plurality of updated subsets in (a)(iii)(3), determining a sum of a sensitivity and a specificity for the cancer from results of the first ROC analysis performed in (a)(iii)(1)(B) and the second ROC analysis performed in (a)(iii)(2)(B), wherein a higher sum indicates a higher probability of the cancer; and
      (5) weighting the updated subset using the sum of the sensitivity and the specificity, wherein a higher weight indicates a higher probability of the cancer; and
    (iv) comparing the weighted subset to a threshold weight, thereby identifying the weighted subset above the threshold weight as an indicator of the cancer;
  (b) determining that a subject has the cancer or is likely to develop the cancer with at accuracy of at least 95%, wherein a sample obtained from the subject comprises one or more microsatellite loci from the weighted subset in (a)(iv); and
  (c) treating the cancer in the subject, wherein the treating comprises performing surgery or delivering chemotherapy, radiation, cancer-targeted drug therapy, or an immune therapy treatment to the subject.

13. The computer system of claim 12, wherein the one or more processors are further configured to cause the system to compare microsatellite loci in a first set of samples from subjects with cancer and microsatellite loci in a second set of samples from subjects without cancer, thereby identifying the initial population of microsatellite alleles.

14. The computer system of claim 12, wherein the plurality of updated subsets comprises at least 100 subsets.

15. The computer system of claim 12, wherein duplicate microsatellite loci are not allowed in a subset of the plurality of updated subsets of microsatellite loci.

16. The system of claim 12, wherein the cancer-targeted drug therapy comprises one or more of afatinab, gefinib, bevacizumab, crizotinib, and ceritinib.

17. The system of claim 12, wherein the one or more immunotherapy treatments comprise treatments with monoclonal antibodies, checkpoint inhibitors, therapeutic vaccines, or adoptive T-cell transfer.

18. A non-transitory computer-readable medium comprising instructions that, when executed by a processor of a processing system, cause the processing system to perform a method of constructing an optimized classifier for cancer, the method comprising;
  (a) training in a machine learning model by a computer, wherein the training comprises:
    (i) weighting an initial population of microsatellite loci as indicators of the cancer;
    (ii) obtaining subsets of the initial population of microsatellite loci, wherein a number of microsatellite loci in each of the subsets is an order of magnitude lower than a number of microsatellite loci in the initial population of microsatellite loci;
    (iii) performing a plurality of optimization cycles, wherein an optimization cycle of the plurality of optimization cycles comprises:
      (1) generating a first new subset of microsatellite loci by a process comprising:
        (A) randomly selecting microsatellite loci from a first combination of the subsets from (a)(ii) and combining the microsatellite loci to produce the first new subset, wherein the first new subset is distinct from any subset in the subsets from (a)(ii); and (B) performing a first receiving operating characteristic (ROC) analysis with (1) the microsatellite loci from the first new subset, (2) microsatellite loci obtained from a first portion of the reference subjects with the cancer, and (3) microsatellite loci obtained from a second portion of the reference subjects without the cancer;

(2) generating a second new subset of microsatellite loci by a process comprising:

(A) randomly selecting microsatellite loci from a second combination of the subsets from (a)(ii) to produce second new subset, wherein the second new subset is distinct from any subset in the subsets from (a)(ii); and (B) performing a second ROC analysis with (1) the microsatellite loci from the second new subset, (2) microsatellite loci obtained from a second portion of the reference subjects with the cancer, and (3) microsatellite loci obtained from a second portion of the reference subjects without cancer;

(3) adding the first new subset and the second new subset to the initial population of the microsatellite loci when no previous optimization cycle has been performed, or adding the first new subset and the second new subset to subsets from the previous optimization cycle to generate a plurality of updated subsets of the initial population of the microsatellite loci;

(4) for an updated subset of the plurality of updated subsets in (a)(iii)(3), determining a sum of a sensitivity and a specificity for the cancer from results of the first ROC analysis performed in (a)(iii)(1)(B) and the second ROC analysis performed in (a)(iii)(2)(B), wherein a higher sum indicates a higher probability of the cancer; and (5) weighting the updated subset using the sum of the sensitivity and the specificity, wherein a higher weight indicates a higher probability of the cancer; and (iv) comparing the weighted subset to a threshold weight, thereby identifying the weighted subset above the threshold weight as an indicator of the cancer;

(b) determining that a subject has the cancer or is likely to develop the cancer with accuracy of at least 95%, wherein a sample obtained from the subject comprises one or more microsatellite loci from the weighted subset in (a)(iv); and (c) treating the cancer in the subject, wherein the treating comprises performing surgery or delivering chemotherapy, radiation, cancer-targeted drug therapy, or an immune therapy treatment to the subject.

19. The non-transitory computer-readable medium of claim 18, wherein:

the cancer-targeted drug therapy comprises administration of one or more of afatinab, gefinib, bevacizumab, crizotinib, and ceritinib.

20. The non-transitory computer-readable medium of claim 18, wherein the one or more immunotherapy treatments comprise treatments with monoclonal antibodies, checkpoint inhibitors, therapeutic vaccines, or adoptive T-cell transfer.

* * * * *